US008076445B2

(12) United States Patent
Shane Porzio et al.

(10) Patent No.: US 8,076,445 B2
(45) Date of Patent: *Dec. 13, 2011

(54) OLIGOCARBODIIMIDES FOR THE FORMATION OF CROSSLINKED LATEX FILMS

(76) Inventors: Robert Shane Porzio, Charlotte, NC (US); Karl Häberle, Speyer (DE); Jacob Wildeson, Chamberburg, PA (US); Martin Jung, Mannheim (DE); Norbert Willenbacher, Kirchheimbolanden (DE); Lars Börger, Mannheim (DE)

( * ) Notice: Subject to any disclaimer, the term of this patent is extended or adjusted under 35 U.S.C. 154(b) by 753 days.

This patent is subject to a terminal disclaimer.

(21) Appl. No.: 10/372,150

(22) Filed: Feb. 21, 2003

(65) Prior Publication Data
US 2003/0220462 A1  Nov. 27, 2003

Related U.S. Application Data

(63) Continuation-in-part of application No. 10/169,070, filed as application No. PCT/EP01/00057 on Jan. 5, 2001, now Pat. No. 7,049,001.

(30) Foreign Application Priority Data

Jan. 11, 2000  (DE) .................................. 100 00 656

(51) Int. Cl.
*C08G 18/00* (2006.01)
(52) U.S. Cl. ............. 528/44; 524/589; 524/591; 528/67
(58) Field of Classification Search .................... 528/44, 528/67; 524/589, 591
See application file for complete search history.

(56) References Cited

U.S. PATENT DOCUMENTS

| 3,502,722 | A |   | 3/1970 | Neumann ...................... 560/334 |
| 4,328,138 | A | * | 5/1982 | Lin et al. ......................... 525/451 |
| 4,910,339 | A |   | 3/1990 | Henning et al. .............. 564/252 |
| 5,115,072 | A | * | 5/1992 | Nava et al. ....................... 528/67 |
| 5,276,096 | A | * | 1/1994 | Serdiuk et al. ................. 525/123 |
| 5,866,715 | A |   | 2/1999 | Tsai .............................. 560/302 |
| 5,905,113 | A | * | 5/1999 | Licht et al. ..................... 524/591 |
| 6,121,406 | A |   | 9/2000 | Imashiro et al. .............. 528/170 |
| 6,194,500 | B1 |   | 2/2001 | Imashiro et al. .............. 524/195 |
| 6,235,384 | B1 | * | 5/2001 | Voss et al. ...................... 428/341 |
| 6,395,824 | B1 | * | 5/2002 | Beutler et al. ................. 524/591 |
| 6,552,119 | B1 | * | 4/2003 | Licht et al. ..................... 524/589 |
| 6,599,975 | B1 | * | 7/2003 | Licht et al. ..................... 524/591 |
| 6,610,784 | B1 | * | 8/2003 | Overbeek et al. ............. 525/178 |
| 6,616,797 | B1 | * | 9/2003 | Licht et al. ................. 156/324.4 |
| 6,730,807 | B1 | * | 5/2004 | Haberle et al. ................ 562/439 |
| 6,774,172 | B1 | * | 8/2004 | Nakamura .................... 524/507 |

FOREIGN PATENT DOCUMENTS

| DE | 1130594 |   | 5/1962 |
| DE | 1156401 |   | 3/1970 |
| DE | 3720860 A1 |   | 1/1989 |
| DE | 19521500 |   | 6/1996 |
| DE | 19821668 |   | 11/1999 |
| DE | WO00/11060 | * | 3/2000 |
| DE | 19954006 |   | 5/2001 |
| EP | 198343 |   | 3/1990 |
| EP | 686626 |   | 12/1995 |
| EP | 0950674 | * | 10/1999 |
| EP | 952146 |   | 10/1999 |
| EP | 962490 |   | 12/1999 |
| GB | 1083410 |   | 7/1960 |
| GB | 851936 |   | 10/1960 |
| WO | WO 9906460 | * | 2/1999 |

OTHER PUBLICATIONS

Derwent Accession No. 2000-014370, abstract for DE19821668, Nov. 18, 1999.
"Carbodiimide Chemistry: Recent Advances", A. Williams et al., Chem. Rev. 1981, 81,pp. 589-636.
"The Application of Carbodiimide Chemistry to Coatings", J.W. Taylor et al., ACS Symposium Series 663, 1997, pp. 137-163.
A study on the chemistry of alkylcarbodiimide ethylmethacrylates as reactive for acrylic and vinyl ester-based latexes, J.W. Taylor et al., Progress in Organic Coatings 35, 1999, pp. 215-221.
"Synthesis, Characterization, and Stability of Carbodiimide Groups in Carbodiimide-Functionalized Latex Dispersions and Films", H. Pham et al., J. Polymer Science: Part A: Polymer Chemistry, vol. 38, 2000, pp. 855-869.
"Polymer Interdiffusion vs Cross-Linking in Carboxylic Acid-Carbodiimide Latex Films", H. Pham et al., Macromolecules 32, 1999, pp. 7692-7695.
"Film Formation from Blends of Carbodiimide and Carboxylic Acid-Functional Latex", H. Pham et al., ACS Symposium Series 790, 2001, pp. 88-102.
"Mechanism of the reaction of carbodiimides with carboxylic acids", A.H.M. Schotman, Recl. Trav. Chim. Pays-Bas 110, 1991, pp. 319-324.
"Recent developments in crosslinking technology for coating resins", M. Ooka et al., Progress in Organic Coatings 23, 1994, pp. 325-338.

(Continued)

*Primary Examiner* — Patricia Hightower
*Assistant Examiner* — Gregory Listvoyb
(74) *Attorney, Agent, or Firm* — Cantor Colburn LLP

(57) ABSTRACT

A composition comprising a carbodiimide and a polymer, wherein the carbodiimide comprises a reaction product of a) at least one of an aliphatic $C_4$ to $C_{20}$ polyisocyanate and an araliphatic $C_4$ to $C_{20}$ polyisocyanate, b) at least one of a hydroxy carboxylic acid and a hydroxy carboxylic salt, c) optionally, a further compound carrying groups able to react with isocyanate groups in an addition reaction, d) optionally, at least one other isocyanate, and the carbodiimide units being derived essentially exclusively from the isocyanate groups of component a), and the polymer comprises a reaction product of an ethylenically unsaturated carboxylic acid and at least one of a (meth)acrylate, a vinyl ester of a carboxylic acid, a vinyl aromatic compound, an ethylenically unsaturated nitrile, a vinyl halide, an aliphatic hydrocarbon, and a free-radically polymerizable monomer. Also, a method of applying the composition on and/or in a substrate.

38 Claims, 21 Drawing Sheets

OTHER PUBLICATIONS

"Effect of Crosslinker Reaction Rate on Film Properties for Thermoset Coatings", W. Brown, Journal of Coatings Technology, vol. 72, No. 904, May 2000, pp. 63-70.

"Latices with Intrinsic Crosslink Activity", J.M. Geurts, Ph.D. Thesis, Eindhoven University of Technology, 1997.

International Preliminary Examination Report for International application No. PCT/EP01/00057 dated Jul. 21, 2001.

International Search Report for International application No. PCT/EP01/00057 dated Apr. 20, 2001.

* cited by examiner

Figure 3a
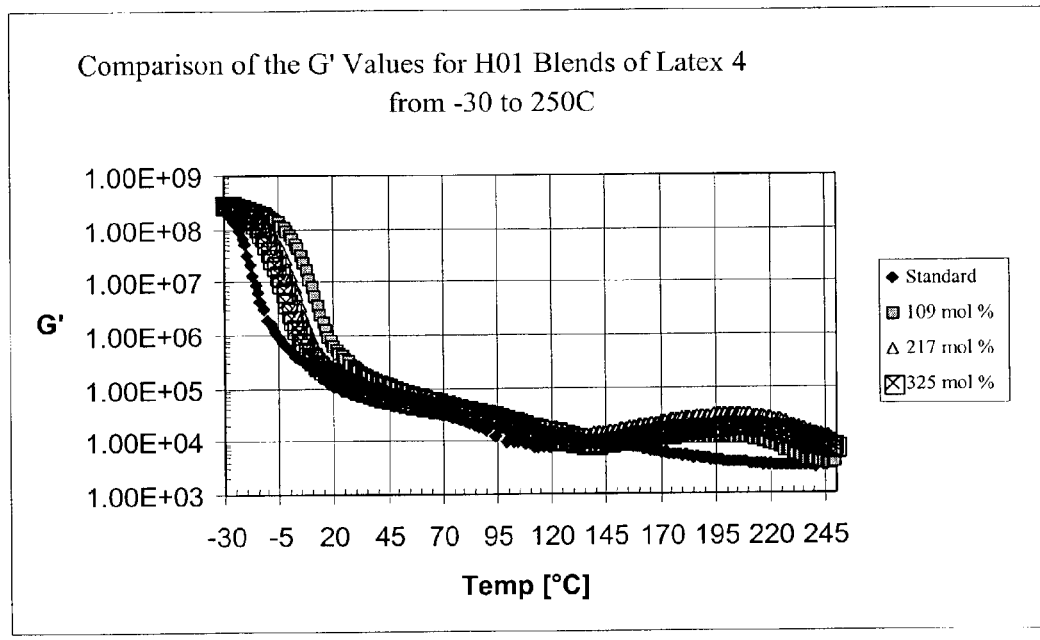
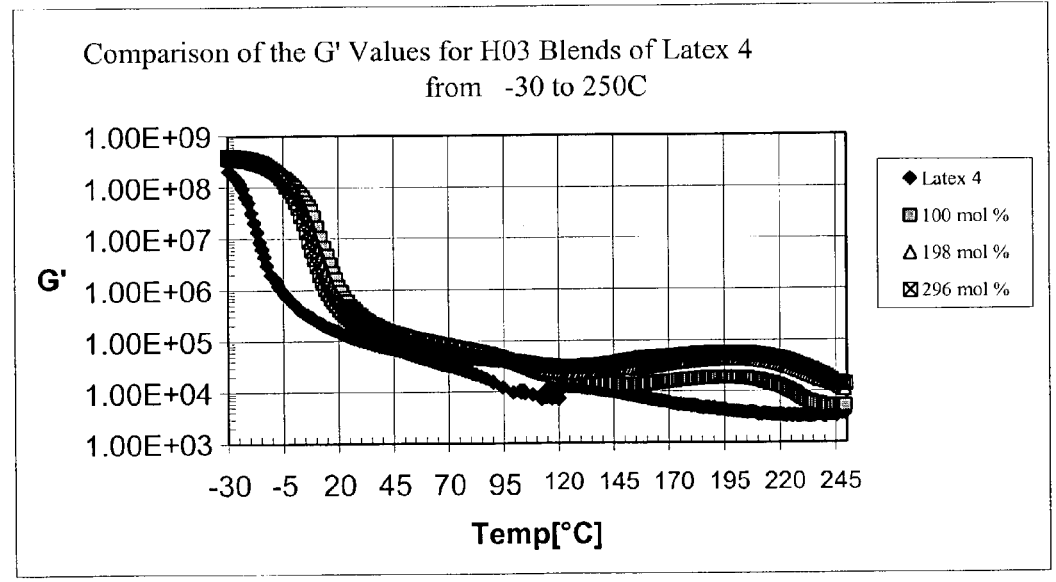
Figure 3b

OLIGOCARBODIIMIDES FOR THE FORMATION OF CROSSLINKED LATEX FILMS

CROSS REFERENCE TO RELATED APPLICATIONS

The present application is a continuation-in-part of U.S. Ser. No. 10/169,070, filed on Jul. 11, 2002, which is a National Stage application of PCT/EP01/00057, filed on Jan. 5, 2001, which claims priority to DE 100 00 656.6, filed on Jan. 11, 2000, all of which are incorporated herein by reference.

BACKGROUND OF THE INVENTION

Organic carbodiimides and their use as additives to aqueous polymer dispersions are known. They are added, for example, to polymer dispersions in order to increase the molecular weight of the polymers. In order to be able to disperse the carbodiimides simply and homogeneously in the dispersion, they are provided with hydrophilic groups.

EP-A-198 343 describes carbodiimides which carry sulfonate groups and also, if desired, polyethylene oxide units.

EP-A-686 626, moreover, discloses carbodiimides in which the hydrophilicity is brought about by ammonium groups, which are introduced by way of dialkylamino alcohols, by sulfonate groups, which are introduced by way of salts of hydroxy-functional alkylsulfonic acids, or by polyethylene oxide radicals.

The abovementioned products, however, have the following disadvantages:

Cationic products, such as carbodiimides hydrophilicized by ammonium groups, are incompatible with the anionically stabilized dispersions that are usually used.

The carbodiimides hydrophilicized with sulfonate groups are difficult to prepare. Owing to the highly lipophobic nature of the starting salts used, the reaction with the hydrophobic isocyanato-containing precursors is extremely difficult, since their mutual solubility is very low.

The dispersions cured using carbodiimides hydrophilicized with polyalkylene oxide radicals possess an undesirable permanent hydrophilicity.

DE-A-19821668 discloses carbodiimides based on 1,3-bis(1-methyl-1-isocyanatoethyl)benzene in which the hydrophilicization is brought about using amino sulfonic acids.

DE-A-19954006, unpublished at the priority date of the present specification, discloses carbodiimides based on aliphatic or aromatic polyisocyanates where the hydrophilicization is brought about using amino carboxylic acids.

During recent years, increasing environmental concerns over the elimination of VOC's (Volatile Organic Content) in consumer products have accelerated the growth in the importance of latex dispersions for the adhesives and coatings markets. The pursuit to replace solvent-based coatings with more environmentally friendly water based ones, however, has rendered the latter with physical and mechanical properties, such as tensile strength, chemical and abrasion resistance, and toughness, that are not as good as solvent-based coatings. In addition, the appearance of applied latex coatings is observed to be significantly duller than solvent borne ones. These inferior properties are due to the reduced film formation of the latex, which is exacerbated by premature crosslinking. In an attempt to remedy these limitations, there has been a continued interest in discovering and introducing novel crosslinking methods for functionalized latex polymers, which do not compete with film formation yet result in tough films.

Many practical applications of polymer dispersions require the post-cross-linking of polymer films after application to the substrate in order to enhance the mechanical properties of the film such as film-cohesion, solvent resistance, scrub resistance etc. On the one hand, the crosslinking reaction should be efficient and fast at ambient conditions. On the other hand, the reaction should be suppressed during storage to provide for a sufficiently long pot-life of the dispersion. Up to now, a variety of cross-linking systems have been described in the literature that are more or less compliant with these contradictory requirements. Functional groups currently used are aziridine, epoxy, isocyanate, keto, acetoacetoxy, and carbodiimide groups. Of course, all these groups necessitate complementary functional groups for cross-linking and there are several strategies to bring these complementary functional groups into the dispersion system:

a) They can simply be incorporated into the same dispersion, i.e. complementary groups coexist within one latex particle. Evidently, a limited pot-life will be the consequence.

b) The complementary groups can be introduced into the water-phase where they would stay un-reacted until they get close to their counter-parts during film-formation.

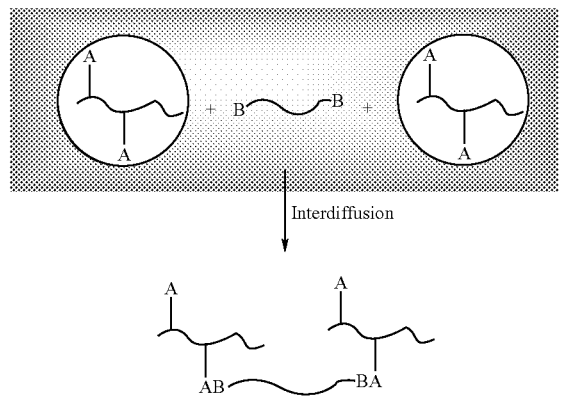

c) Another route would be to synthesize two different latexes bearing the complementary functional groups and blending these latexes before application. The reactive groups would then be separated in the first place and could encounter upon film-formation, after inter-diffusion of the polymer chains.

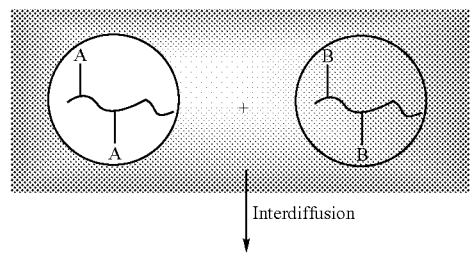

-continued

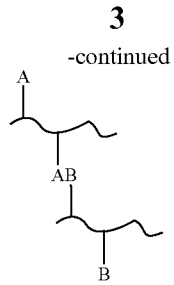

Recently, carbodiimide (CDI) chemistry has attracted interest as a cross-linking system for latex systems. The cross-linking reaction between carbodiimide and carboxylic acid occurs at ambient conditions forming predominantly N-acyl urea products according to the reaction shown below.

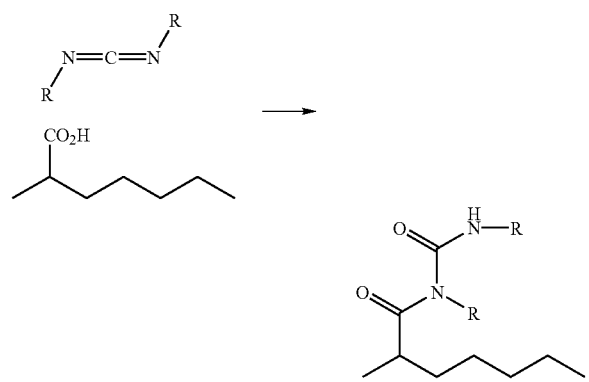

The reaction rate depends both on the structure of the CDI and on the acid. Aliphatic CDIs are reported to be highly reactive; whereas, their aromatic counterparts are less reactive. The reaction rate can be even further decreased by introducing steric hindrance near the CDI group. Finally, it is known that strong acids react at a slower rate with CDIs than weak acids, such as carboxylic acids, do. The resulting cross-linking rate will therefore depend on the interplay of all these parameters. Extra complications come into play by the process of film formation where the competition between polymer inter-diffusion and rate of cross-linking determine the final degree and topology of the polymer cross-links.

According to route b), it is desired that the maximum reaction rate of the cross-linking system to be slower than the rate of film formation in order to get complete property development in terms of hardness, scrub resistance, and solvent resistance.

Among the candidates of latexes with reactive groups, carboxylated latexes continue to be among the most desired for crosslinking films. This choice is due to several reasons: 1) carboxyl groups already cofunction in the surface stabilization of latex particles, and, therefore, do not have to be specially incorporated into the latex, 2) the reactivity of the carboxyl groups is very energetically favored at ambient temperatures, and 3) carboxyl groups can take part in a broad assortment of different crosslinking reactions with a wide variety of a coreactive groups (e.g. ionic crosslinkers). Out of this wide variety of coreactive groups, carbodiimides react with carboxylated functionalized latex coatings to provide the N-acyl urea crosslinks described above.

It would be desirable to obtain a composition from a carboxylated latex crosslinked with a carbodiimide that has desired properties in a film formed from the composition.

SUMMARY OF THE INVENTION

The present invention relates to a composition comprising a carbodiimide and a polymer; wherein the carbodiimide comprises a reaction product of
a) at least one of an aliphatic $C_4$ to $C_{20}$ polyisocyanate and an araliphatic $C_4$ to $C_{20}$ polyisocyanate,
b) at least one of a hydroxy carboxylic acid and a hydroxy carboxylic salt,
c) optionally, a further compound carrying groups able to react with isocyanate groups in an addition reaction,
d) optionally, at least one other isocyanate, and the carbodiimide units being derived essentially exclusively from the isocyanate groups of component a), and the polymer comprises a reaction product of an ethylenically unsaturated carboxylic acid and at least one of a $C_1$ to $C_{20}$ alkyl (meth)acrylate, a vinyl ester of a carboxylic acid containing up to 20 carbon atoms, a vinyl aromatic compound having up to 20 carbon atoms, an ethylenically unsaturated nitrile, a vinyl halide, an aliphatic hydrocarbon having 2 to 8 carbon atoms and 1 or 2 double bonds, and a free-radically polymerizable monomer.

Also, the present invention relates to a method of applying the composition to at least one of on and in a substrate.

BRIEF DESCRIPTION OF THE DRAWINGS

FIGS. 3a and 3b are graphs of DMA data of the compositional ladder study of EH01 and EH03 with Latex 4.

FIG. 1d is a graph of storage modulus behavior for different samples from Example Set 2.

DETAILED DESCRIPTION

Figure 1:
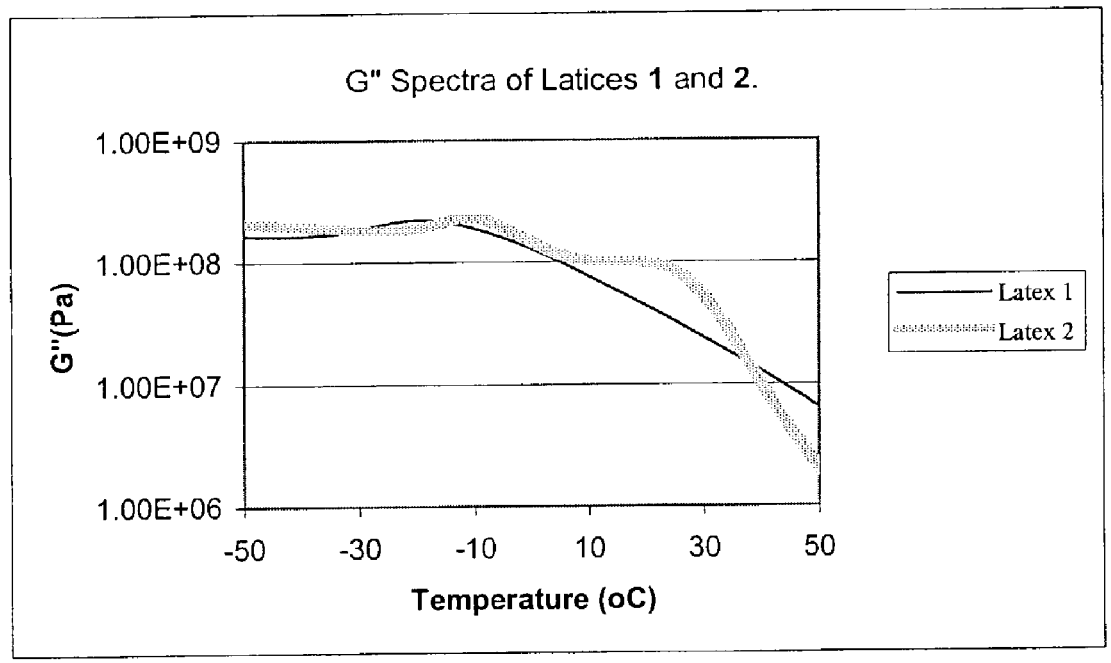
FIG. 1 is a graph of the Dynamic Mechanical Analysis (DMA) of Latexes 1 and 2.
Figure 2A:
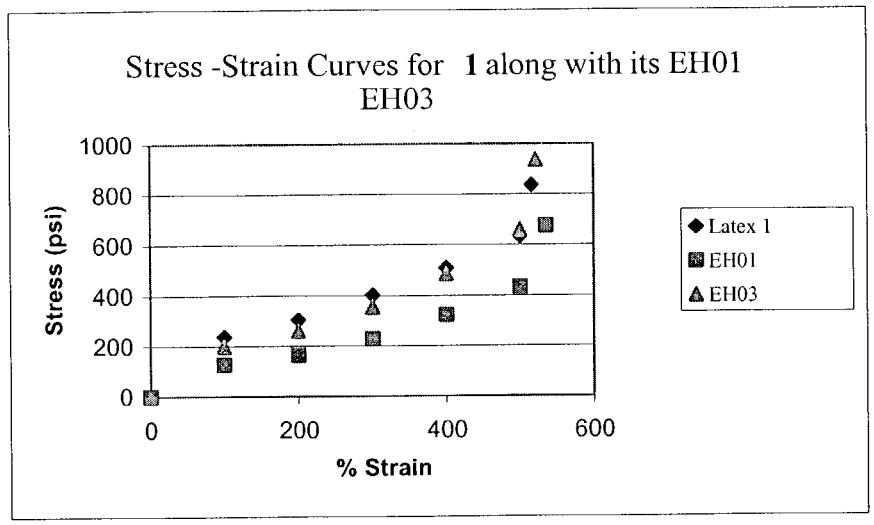
FIGS. 2a to 2f are graphs of stress-strain curves of Latexes 1-6 along with their respective blends with ELASTOSTAB® H01 (EH01) and ELASTOSTAB® H03 (EH03) carbodiimide.
Figure 2B:
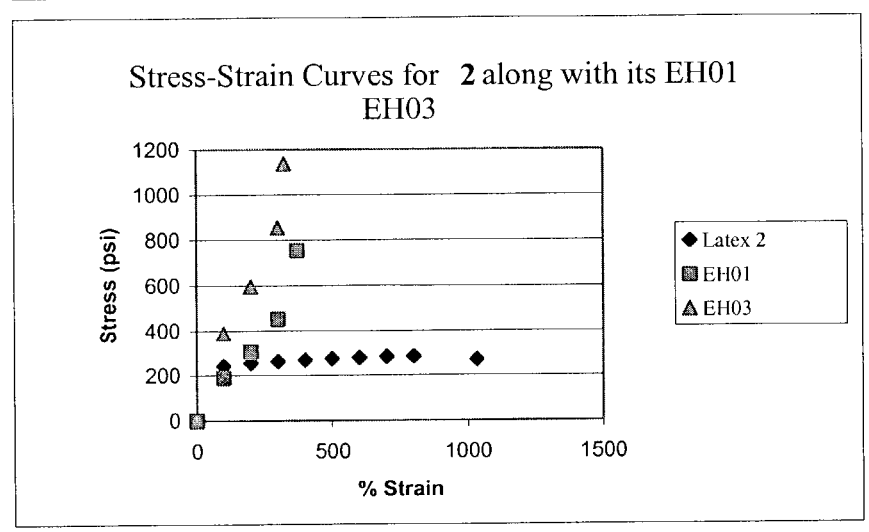
Figure 2C:
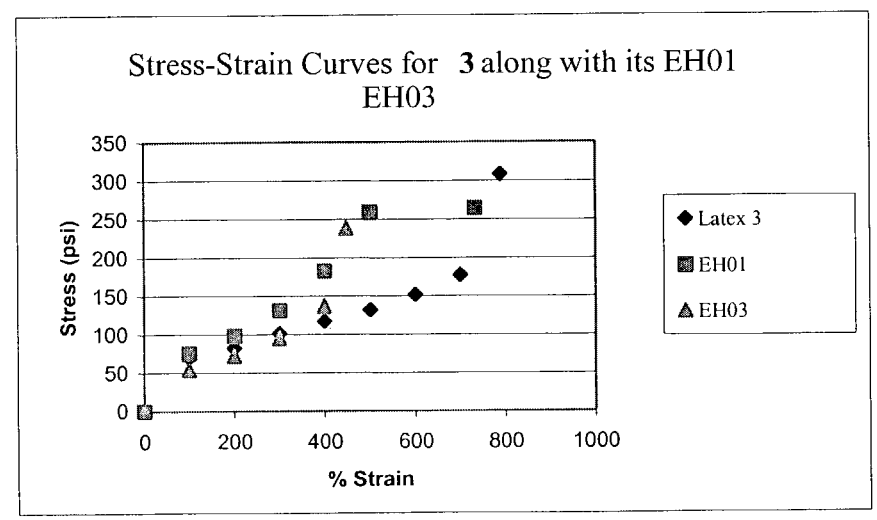
Figure 2D:
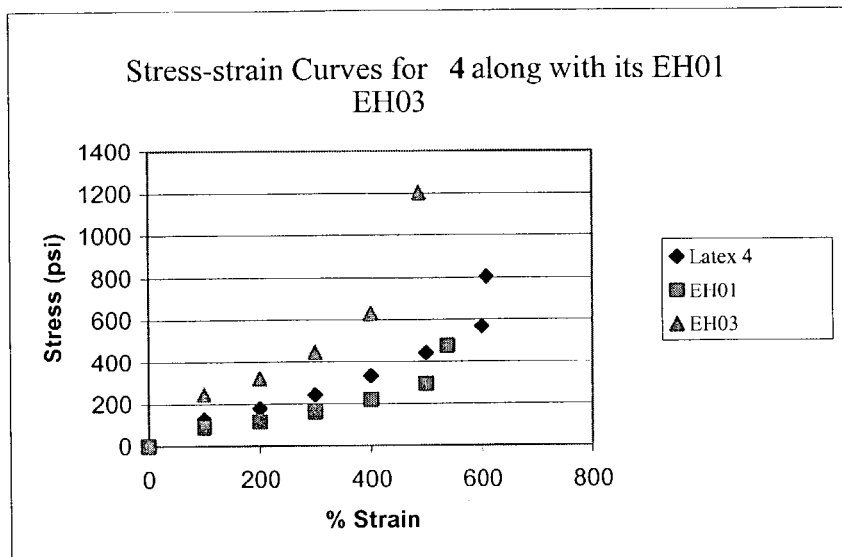
Figure 2E:
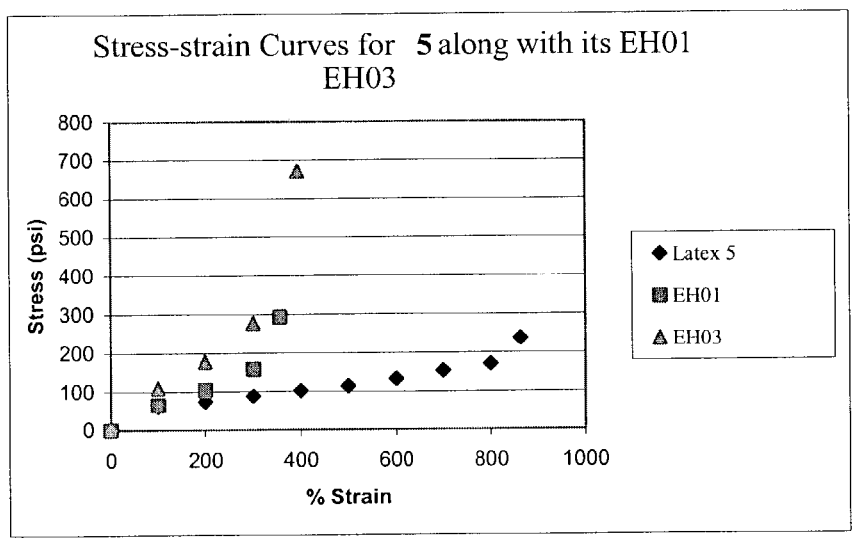
Figure 2F:
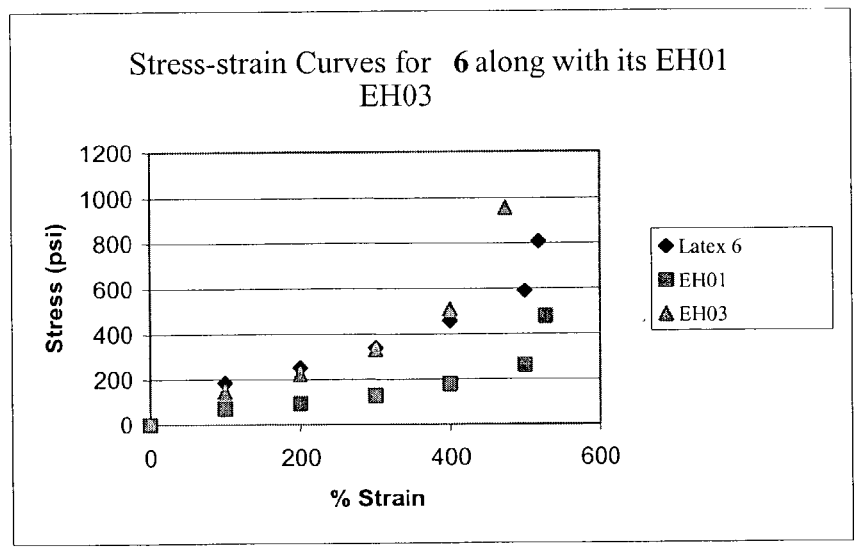
Figure 4A:
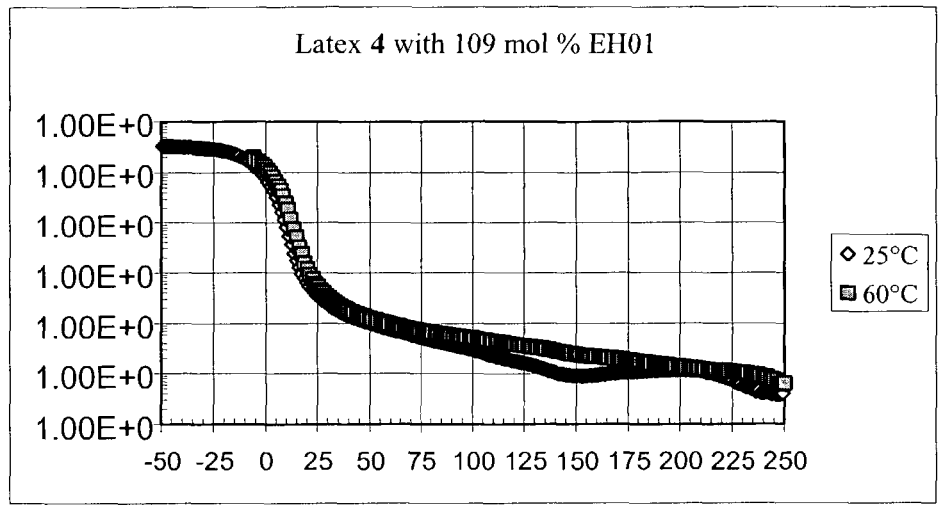
FIGS. 4a to 4f are graphs of DMA analyses of Latex 4 with blends of EH01 and EH03 at different levels cured at 25° C. and at 60° C.
Figure 4B:
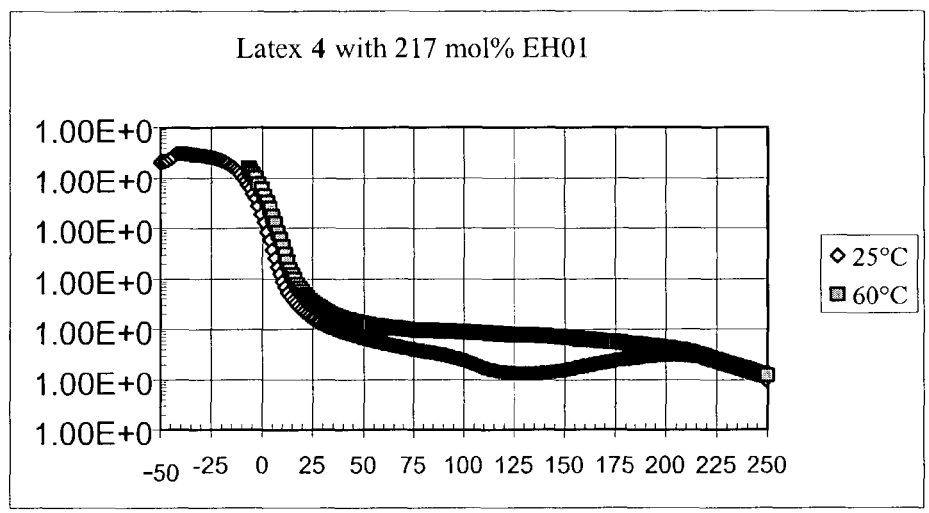
Figure 4C:
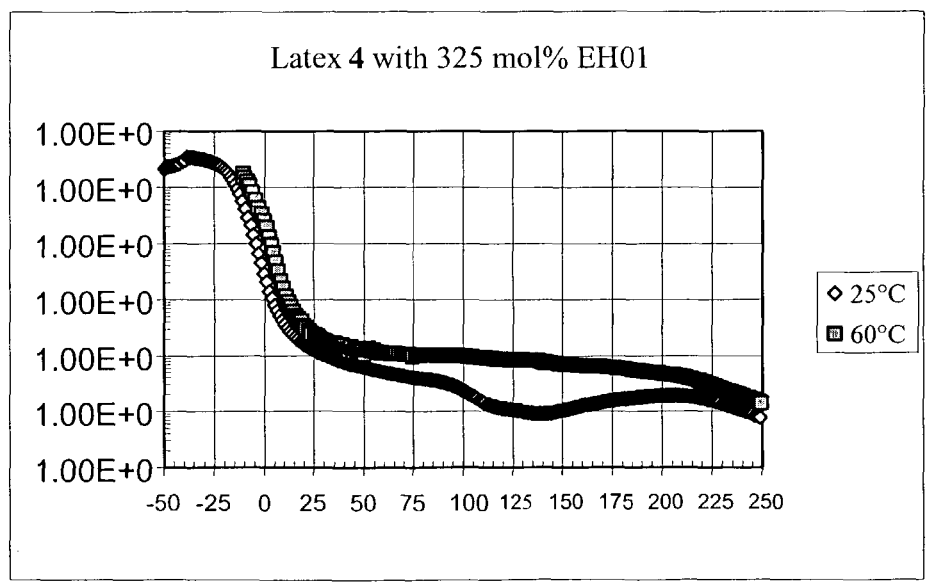
Figure 4D:
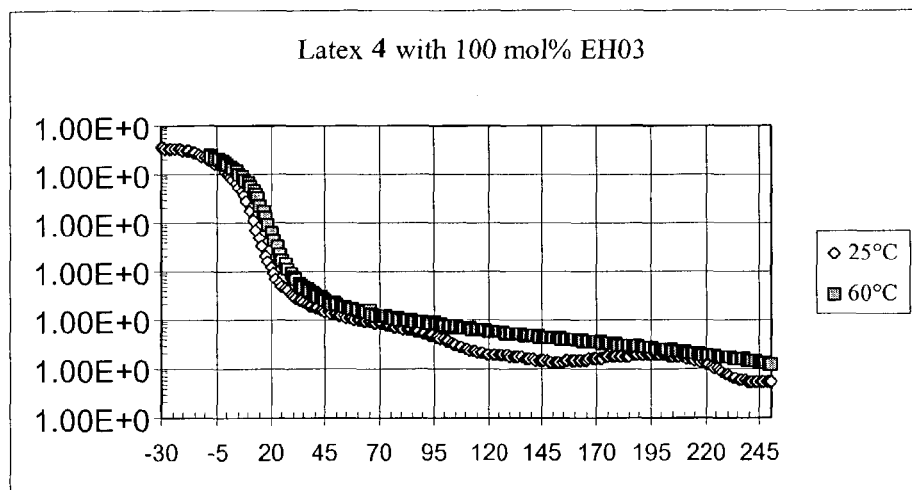
Figure 4E:
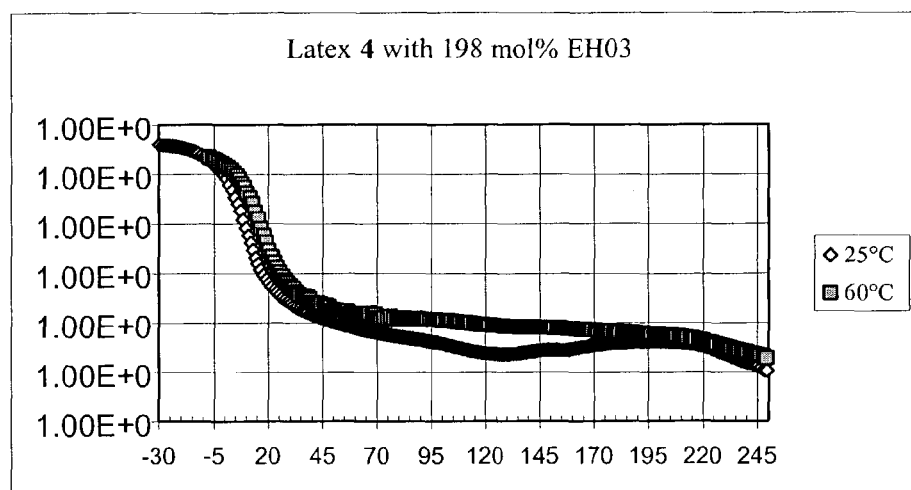
Figure 4F:
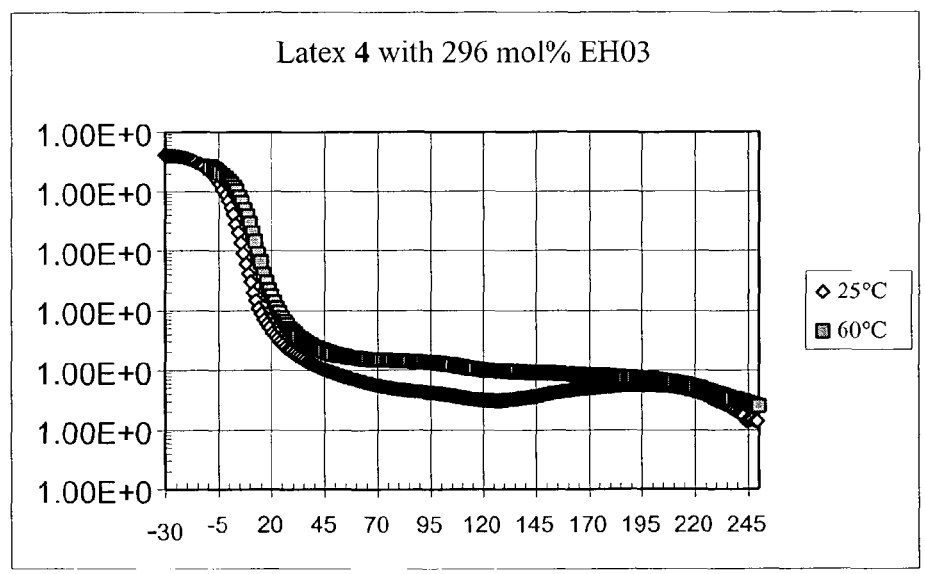
Figure 5A:
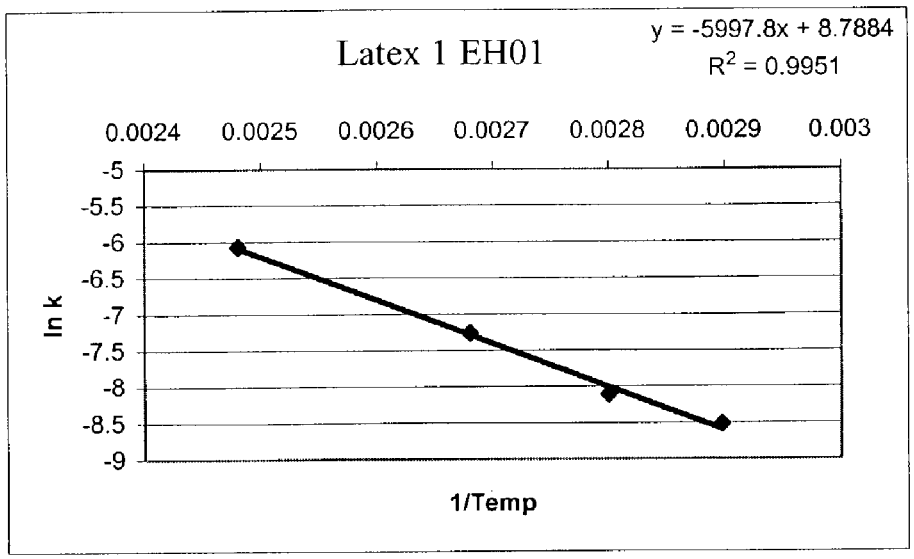
FIGS. 5a to 5f are Arrhenius Plots of heat cured blends of EH01 and EH03 with Latexes 1, 2, and 4.
Figure 5B:
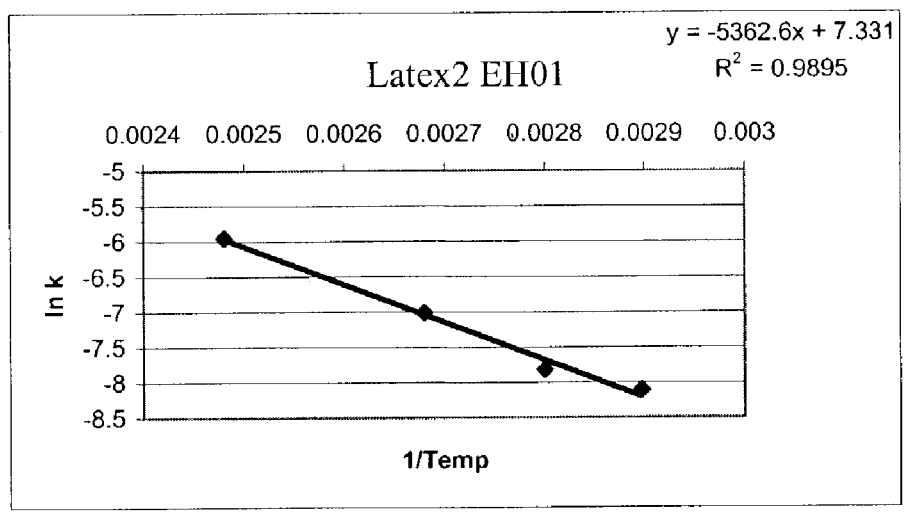
Figure 5C:
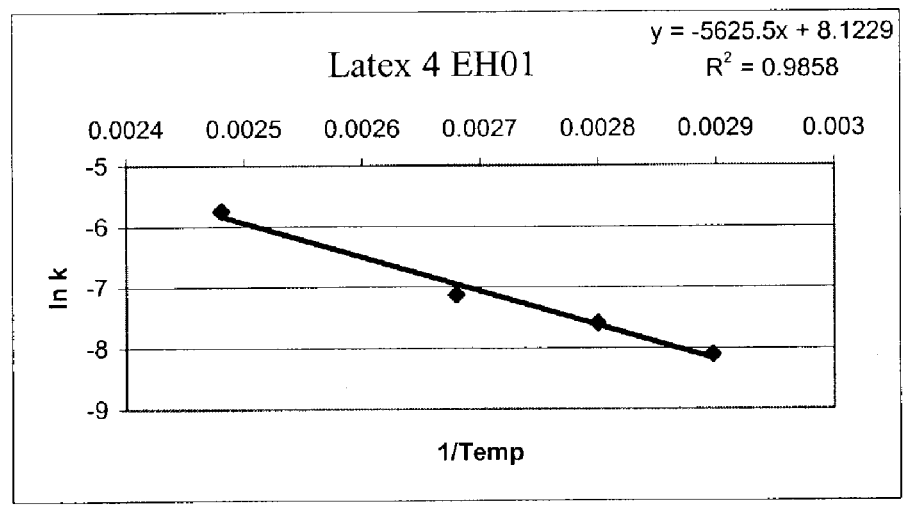
Figure 5D:
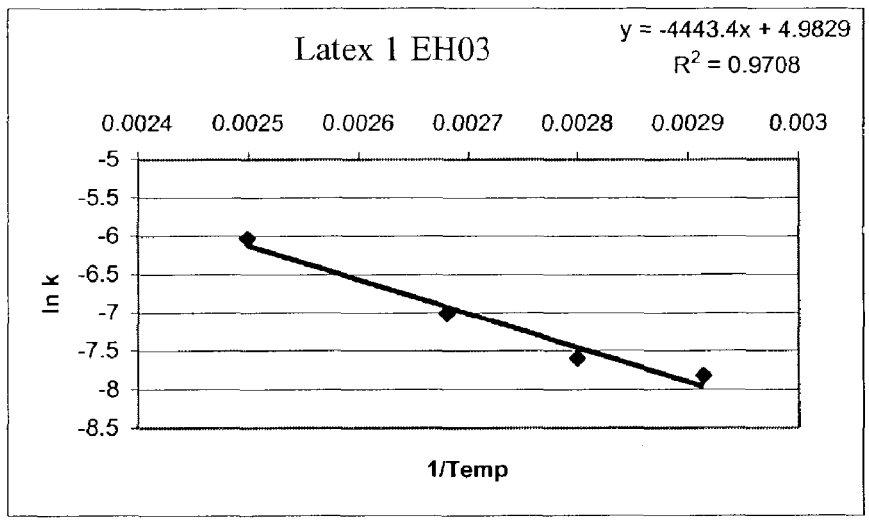
Figure 5E:
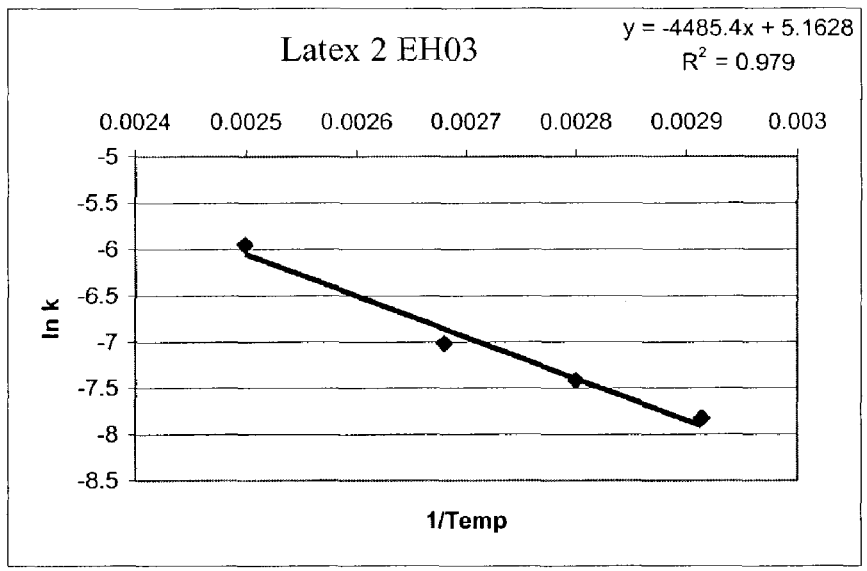
Figure 5F:
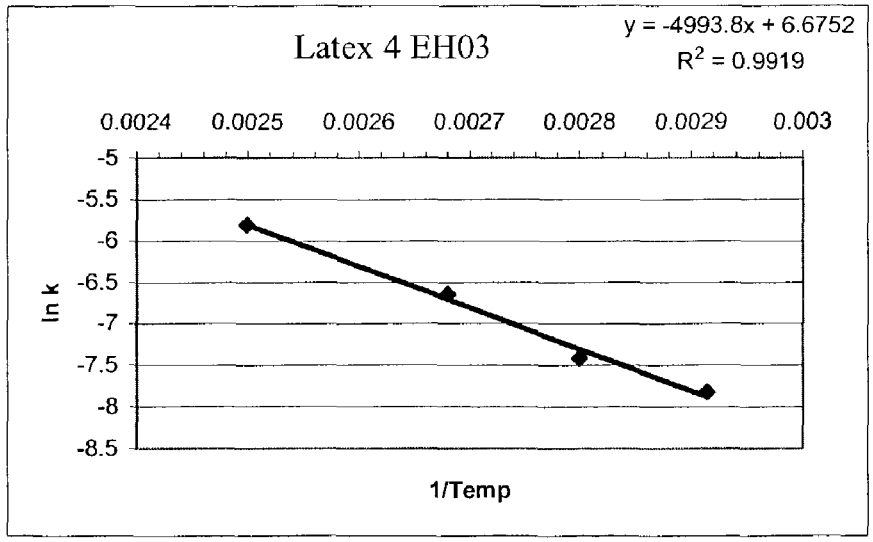

As used throughout, ranges are used as a shorthand for describing each and every value that is within the range. Any value within the range can be selected as the terminus of the range.

The invention relates to compounds having carbodiimide units and carboxyl or carboxylate groups (compounds V), derived from aliphatic or araliphatic $C_4$ to $C_{20}$ polyisocyanates (component a)

hydroxy carboxylic acids or hydroxy carboxylic salts (component b) and if desired, further compounds, carrying groups able to react with isocyanate groups in an addition reaction (component c)

if desired, other isocyanates (component d), the carbodiimide units being derived essentially exclusively from the isocyanate groups of component a).

The compounds (V) contain preferably from 200 to 2000 mmol/kg, with particular preference from 500 to 1800 mmol/kg, of carboxyl or carboxylate groups, based on the weight of the carbodiimides.

The carbodiimide group content is generally from 0.05 to 8, preferably from 0.10 to 5, mol/kg, based on the weight of the carbodiimides.

The carbodiimide units in the carbodiimides of the invention are essentially each formed by the coming together of any two NCO groups of component (a) with elimination of carbon dioxide to form one carbodiimide unit.

The compounds (V) preferably contain at least one carbodiimide unit, more preferably more than one carbodiimide unit; with particular preference, the average degree of condensation (number average), i.e., the average number of carbodiimide units in the carbodiimides of the invention, is from 1 to 20, in particular from 2 to 15.

Suitable monomers (a) are the aliphatic or araliphatic isocyanates having 4 to 20 carbon atoms that are commonly used in polyurethane chemistry.

Mention may be made in particular of diisocyanates $X(NCO)_2$, where X is an aliphatic hydrocarbon radical having 4 to 12 carbon atoms, a cycloaliphatic hydrocarbon radical having 6 to 15 carbon atoms, or an araliphatic hydrocarbon radical having 7 to 15 carbon atoms. Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl)propane, trimethylhexane diisocyanate, 1,4-diisocyanatobenzene, 1,3-bis(1-methyl-1-isocyanatoethyl)benzene (TMXDI), the isomers of bis(4-isocyanatocyclohexyl)methane (HMDI), such as the trans/trans, the cis/cis and the cis/trans isomers, and mixtures of these compounds.

The carbodiimides of the invention therefore preferably contain units of the formula I

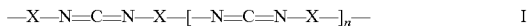

where X is as defined above, and n is an integer from 0 to 10, preferably from 0 to 5. With particular preference, X is derived from TMXDI or hexamethylene diisocyanate.

Suitable hydroxy carboxylic acids are, for example, those specified in Beyer, Lehrbuch der Organischen Chemie, 19$^{th}$ edition on p. 262 ff.

Although acids with aromatically attached hydroxyl groups are also suitable, acids with aliphatically attached hydroxyl groups are preferred. Particular preference is given to hydroxy carboxylic acids having a hydroxyl group in the beta position, such as beta-hydroxypropionic acid or, with particular preference, hydroxypivalic acid, or alpha,alpha-hydroxymethylalkanoic acids such as dimethylolpropionic acid, for example. Also, dimethylolbutyic acid can be used.

Where the hydroxy carboxylic acids are used in the form of their salts, particularly suitable salts are alkali metal, alkaline earth metal, or ammonium salts.

Preferred compounds (V) are those of the formula II

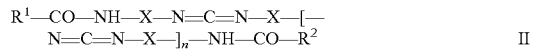

where n and X are as defined for formula I and $R^1$ and $R^2$ are radicals derived from component (b) by abstraction therefrom of a hydrogen atom attached to a hydroxyl group.

In addition to the structural units derived from components (a) and (b), the compounds (V) may, if desired, further comprise other structural units, which are derived from components (c) and (d) and comprise primarily urethane or urea units. These are formed by reacting the isocyanate groups of component (d) with the isocyanate-reactive groups of component (c) or with the hydroxyl groups of component (b) or by reacting the isocyanate-reactive groups of component (c) with the isocyanate groups of component (a). Therefore, the structural units of the formula I are interrupted or terminated by the structural units derived from components (c) and (d) or are located between a structural unit formed from components (a) and (b). Components (c) and (d) therefore serve primarily to regulate the molecular weight, since components (c) and (d) act primarily as the chain extender or chain terminator.

Components (c) carry groups which are able to react with isocyanate groups in an addition reaction. It is possible, for example, to use common substances which by virtue of their reaction with isocyanates produce urethane or urea groups. It is possible, for example, to use aromatic, aliphatic or araliphatic compounds having 1 to 20 carbon atoms, containing hydroxyl and/or amino groups as isocyanate-reactive groups. Preferred compounds having at least two isocyanate-reactive groups are organic compounds having at least two hydroxyl groups, having at least two amino groups, and/or at least one hydroxyl group and at least one amino group. Examples of those which it is possible to use are the following: aromatic, araliphatic and/or aliphatic polyols having 2 to 20 carbon atoms, preferably those having primary hydroxyl groups. Examples that may be mentioned include the following: 1,2-ethanediol, 1,3-propanediol, 1,2-propanediol, 1,4-, 2,4- and/or 2,3-butanediol, 1,5-pentanediol, 1,6-hexanediol, 1,7-heptanediol, 1,8-octanediol, 1,10-decanediol, neopentyl glycol, 2-methyl-1,3-propanediol, 2- and 3-methyl-1,5-pentanediol, polyethylene glycols, polypropylene glycols, preferably having two hydroxyl groups, the isomers of bis(hydroxy-methyl- or -ethyl)benzene, hydroxyalkyl ethers of dihydroxybenzenes, trimethylolpropane, glyceryl, pentaerythritol, or sugars having, for example, 4, 5 or 6 hydroxyl groups.

If isocyanate-reactive compounds which have ethylene oxide units are used, the fraction of ethylene oxide units in the carbodiimides of the invention should be preferably from 1 to 15% by weight, based on the weight of the carbodiimides. Preferably, no such compounds are used.

Amines to be used are amines having at least two primary and/or secondary amino groups. Examples that may be mentioned include the following: amines of the molecular weight range from 32 to 500 g/mol, preferably from 60 to 300 g/mol, which have at least two primary, at least two secondary, or at least both one primary and one secondary amino group. Examples of these are diamines such as diaminoethane, diaminopropane, diaminobutane, diaminopentane, diaminohexane, piperazine, 2,5-dimethylpiperazine, 1-amino-3,3,5-trimethyl-5-aminomethylcyclohexane, (isophoronediamine, IPDA), 4,4'-diaminodicyclohexylmethane, 1,4-diaminocyclohexane, aminoethylethanolamine, hydrazine, hydrazine hydrate, or triamines such as diethylenetriamine or 1,8-diamino-4-aminomethyloctane.

It is also possible to use amines derived from the above-mentioned amines by the substitution of one or more primary amino groups with further substituents, such as alkyl groups, for example, to give secondary amino groups. It is further also possible to use compounds having both at least one hydroxyl group and at least one amino group, examples being ethanolamine, propanolamine, isopropanolamine, aminoethylethanolamine, or N-alkyl amines derived therefrom.

Preference is given to the use of linear alcohols, amines or amino alcohols, particular preference to those having an even number of carbon atoms. Also preferred are alcohols, amines or amino alcohols containing cyclic structural elements.

If desired, it may be judicious, in addition to the above-described, isocyanate-reactive compounds having at least two functional groups, to use monofunctional compounds as well, in order to regulate the molecular weight of the carbodiimides of the invention, especially if the diisocyanates are reacted to the carbodiimides in a first step and then the isocyanato-containing carbodiimides are reacted with the isocyanate-reactive compounds. Monofunctional, isocyanate-reactive compounds which can be used are, for example, amines and, preferably, alcohols. Suitable amines, e.g., primary or preferably secondary amines, advantageously possess 1 to 12 carbon atoms, preferably 2 to 8 carbon atoms. Examples that may be mentioned include methyl-, ethyl-, propyl-, butyl-, pentyl-, hexyl-, 2-ethylhexyl-, octyl-, decyl-, diethyl-, dipropyl-, dibutyl-, methylbutyl-, ethylbutyl- and ethylhexylamine and also cyclohexylamine and benzylamine. To satisfy the isocyanate groups it is preferred, however, to use alcohols, e.g., primary or secondary alcohols of from 1 to 18 carbon atoms, preferably from 2 to 8 carbon atoms. Examples of primary or secondary alcohols that may be mentioned include the following: methanol, ethanol, n-propanol, isopropanol, n-butanol, sec-butanol, n-pentanol, technical-grade pentanol mixtures, n-hexanol, technical-grade hexanol mixtures, 2-ethylhexanol, octanol, 2-ethyloctanol, decanol and dodecanol, and also cyclohexanol and benzyl alcohol.

Component (b) is preferably used with monofunctional compounds, with particular preference monohydroxyls.

In general, the molecular weight of components (c) is less than 400; in particular, the carbodiimides of the invention are free from units derived from macropolyols such as polyether polyols or polyester polyols having a molecular weight of more than 400.

Suitable components (d) are primarily aromatic isocyanates, e.g., 1,4-diisocyanatobenzene, 2,4-diisocyanatotoluene, 2,6-diisocyanatotoluene, 4,4'-diisocyanatodiphenylmethane or 2,4'-diisocyanatodiphenylmethane.

In general, the proportion of components (c) and (d), based on the proportion of all components (a) to (d) used to prepare the compounds V is not more than from 0 to 40% by weight, preferably from 0 to 30% by weight.

The carbodiimides of the invention are prepared essentially by two reaction steps, by
 I. preparing carbodiimides having terminal isocyanate groups, by carbodiumidizing some of the isocyanate groups of component (a), and
 II. reacting the compounds prepared in step I, having terminal isocyanate groups, with component (b) and, if desired, components (c) and (d).

In step I, carbodiimide structures are produced by conventional reaction of the isocyanate groups with one another, with elimination of carbon dioxide, in the presence of customary catalysts known for this reaction. In step II, isocyanate groups are reacted with isocyanate-reactive compounds in a conventional manner to produce urethane and/or urea structures.

The molar ratio of the NCO groups of the isocyanato-containing carbodiimide to the sum of the isocyanate-reactive groups of component (c) and the hydroxyl groups of component (b) is usually from 10:1 to 0.2:1, preferably from 5:1 to 0.5:1.

Alternatively, the carbodiimides of the invention may be obtained by reacting component (a) first with components (b) and, if desired, (c), the ratio of isocyanate groups used to the sum of the isocyanate-reactive groups of component (c) and the hydroxyl groups of component (b) being at least 2:1, and subsequently reacting the isocyanato-containing reaction product to carbodiimides, in the presence of catalysts and with release of carbon dioxide. In accordance with this process variant, up to 50% by weight, preferably up to 23% by weight, of the isocyanate groups of component (a) are first reacted with the isocyanate-reactive compounds and then some or all of the free isocyanate groups are reacted to carbodiimide groups in the presence of catalysts, with release of carbon dioxide.

The reactions may preferably be conducted in the presence of a solvent. Suitable solvents are in particular those compounds which readily dissolve the product of the reaction of step I and are also miscible with water, examples being methanol, ethanol, n- and/or isopropanol, propanone, tetrahydrofuran, dioxane, N-methylpyrrolidone, dimethylformamide, dimethylacetamide, and/or propylene carbonate. Preference is given to the use of solvents having a boiling point at $10^{13}$ mbar of less than 100° C.

The process step wherein the carbodiimide groups are formed may be conducted at elevated temperatures, e.g., at temperatures from 50 to 200° C., preferably from 150 to 185° C., judiciously in the presence of catalysts. Processes suitable for this purpose are described, for example, in GB-A-1 083 410, DE-B 1 130 594 (GB-A-851 936), and DE-A-11 56 401 (U.S. Pat. No. 3,502,722). Compounds which have proven excellent as catalysts are, for example, phosphorus compounds, selected preferably from the group consisting of phospholenes, phospholene oxides, phospholidines, and phospholine oxides. The polycarbodiimide formation is normally ended when the reaction mixture has the desired NCO group content. To accomplish this ending, the catalysts may be distilled off under reduced pressure or deactivated by adding a deactivator, such as phosphorus trichloride, for example. The preparation of the polycarbodiimides may also be conducted in the absence or presence of solvents which are inert under the reaction conditions.

The temperature during the step in which predominantly urethane and urea groups are formed is usually from 10 to 100° C.

If component (a) is reacted first to an isocyanato-containing carbodiimide (step I) and then the compound (V), the intermediate formed in step I preferably has an NCO content of from 1 to 18% by weight.

Through a suitable choice of the reaction conditions, such as, for example, the reaction temperature, the type and amount of catalyst, and the reaction time, the skilled worker is able to adjust the degree of condensation in the usual manner. The course of the reaction may most easily be monitored by determining the NCO content. Other parameters as well, such as, for example, viscosity increase, deepening of color, or $CO_2$ evolution, can be drawn upon for monitoring the progress of, and controlling, the reaction.

The compound (V) of the invention is suitable in particular for increasing the molecular weight of polymers (P) present in the form of an aqueous dispersion.

Suitable polymers (P) are virtually all film-forming polymers.

The polymers (P) preferably carry carboxyl groups, generally in amounts of from 0.01 to 2 mol/kg.

Mixtures of compounds (V) and aqueous dispersions comprising polymer (P) contain compounds (V) and polymer (P) preferably in a weight ratio of from 0.005:1 to 1:1.

The mixing operation is not critical and may be performed, for example, by stirring compound (V) into the aqueous dispersions comprising polymer (P). Mixing may be carried out at any desired point in time prior to their application.

Suitable polymers (P) are, for example, water-dispersible polyurethanes (polymers PII). Polyurethanes of this kind and the dispersions comprising them are common knowledge (cf. Ullmann's Encyclopedia of Industrial Chemistry, 5$^{th}$ Edition, Volume A 21, pages 677 f).

Preferably, dispersions of this kind are composed of

IIa) diisocyanates having 4 to 30 carbon atoms,

IIb) diols of which

IIb1) from 10 to 100 mol %, based on the overall amount of the diols (IIb), have a molecular weight of from 500 to 5000, and IIb2) from 0 to 90 mol %, based on the overall amount of the diols, have a molecular weight of from 60 to 500 g/mol, IIc) monomers other than the monomers (IIa) and (IIb), which have at least one isocyanate group or at least one isocyanate-reactive group and also carry at least one hydrophilic group or one potentially hydrophilic group, which makes the polyurethanes dispersible in water, IId) if desired, further, polyfunctional compounds which are different from the monomers (IIa) to (IIc) and have reactive groups which are alcoholic hydroxyl groups, primary or secondary amino groups, or isocyanate groups, and IIe) if desired, monofunctional compounds which are different from the monomers (IIa) to (IId) and have a reactive group which is an alcoholic hydroxyl group, a primary or secondary amino group, or an isocyanate group.

Suitable monomers (IIa) are the aliphatic or aromatic diisocyanates commonly used in polyurethane chemistry. Preference is given to the monomers (IIa) or mixtures thereof which are mentioned also as monomers (IIa) in DE-A-195 21 500.

Suitable monomers (IIb) and (IId) are preferably those specified in DE-A-195 21 500 as monomers (IIb) and (IId).

Monomers II are, for example, polyester diols or polyether diols.

The monomers IIb2 comprise, for example, aliphatic diols having 2 to 12 carbon atoms, e.g., 1,4-butanediol or 1,6-hexanediol.

Examples of suitable monomers (IId) are aliphatic amines having 2 to 12 carbon atoms and 2 to 4 groups selected from the group consisting of primary and secondary amino groups. Examples are ethylenediamine, isophoronediamine, and diethylenetriamine.

In order to render the polyurethanes dispersible in water they are synthesized not only from components (IIa), (IIb) and (IId) but also from monomers (IIc) which are different from components (IIa), (IIb) and (IId) and which carry at least one isocyanate group or at least one isocyanate-reactive group and, in addition, at least one hydrophilic group or a group which can be converted to a hydrophilic group. In the text below, the term hydrophilic groups or potentially hydrophilic groups is shortened to (potentially) hydrophilic groups.

The (potentially) hydrophilic groups react with isocyanates much more slowly than do the functional groups of the monomers used to synthesize the polymer main chain.

Preferred monomers (IIc) are likewise those designated as monomers (IIc) in DE-A-195 21 500.

The proportion of components having (potentially) hydrophilic groups among the overall amount of components (IIa), (IIb), (IIc), (IId) and (IIe) is generally such that the molar amount of the (potentially) hydrophilic groups, based on the amount by weight of all monomers (a) to (e), is from 80 to 1200, preferably from 100 to 1000, and with particular preference from 150 to 800, mmol/kg.

The (potentially) hydrophilic groups can be nonionic groups, e.g., polyethylene oxide groups, or, preferably, (potentially) ionic hydrophilic groups, e.g., carboxylate groups or sulfonate groups. It is preferred to work without effective amounts of nonionic groups.

The amount of nonionic hydrophilic groups, if such are incorporated, is generally up to 5, preferably up to 3, with particular preference up to 1% by weight, based on the amount by weight of all monomers (IIa) to (IIe).

Monomers (IIe), which are used as well if desired, are monoisocyanates, monoalcohols, and mono-primary and mono-secondary amines. In general, their proportion is not more than 10 mol %, based on the overall molar amount of the monomers. These monofunctional compounds usually carry other functional groups, such as carbonyl groups, and serve to introduce functional groups into the polyurethane which allow the polyurethane to be dispersed and/or crosslinked or to undergo further polymer-analogous reaction.

Within the field of polyurethane chemistry it is generally known how the molecular weight of the polyurethanes can be adjusted by choosing the proportions of the co-reactive monomers and by the arithmetic mean of the number of reactive functional groups per molecule.

Components (IIa) to (IIe) and their respective molar amounts are normally chosen so that the ratio A:B, where A) is the molar amount of isocyanate groups, and B) is the sum of the molar amount of the hydroxyl groups and the molar amount of the functional groups which are able to react with isocyanates in an addition reaction, is from 0.5:1 to 2:1, preferably from 0.8:1 to 1.5, with particular preference from 0.9:1 to 1.2:1. With very particular preference, the ratio A:B is as close as possible to 1:1.

Furthermore, the proportion of the monomers (a) is preferably chosen so that the proportion of the monomers (IIa) among the monomers (IIa) to (IIe) is from 20 to 70% by weight.

The monomers (IIa) to (IIe) that are employed carry on average usually from 1.5 to 2.5, preferably from 1.9 to 2.1, with particular preference 2.0, isocyanate groups and/or functional groups which are able to react with isocyanates in an addition reaction.

The various preparation methods of the polymers PII are common knowledge and are described in more detail, for example, in DE-A-198 07 754.

The polymers (P) may further comprise conventional emulsion polymers (polymers PIII).

These are composed in general of

IIIa) from 30 to 99.9% by weight of principal monomers selected from $C_1$ to $C_{20}$ alkyl (meth)acrylates, vinyl esters of carboxylic acids containing up to 20 carbon atoms, vinylaromatic compounds having up to 20 carbon atoms, ethylenically unsaturated nitriles, vinyl halides, and aliphatic hydrocarbons having 2 to 8 carbon atoms and 1 or 2 double bonds, IIIb) from 0 to 20, preferably from 0.01 to 20, % by weight of a carboxylic acid having an olefinic double bond, and IIIc) from 0 to 20% by weight of free-radically polymerizable monomers other than (IIIa) and (IIIb).

Examples that may be mentioned of monomers (IIIa) are (meth)acrylic acid alkyl esters having a $C_1$-$C_{10}$ alkyl radical, such as methyl methacrylate, methyl acrylate, n-butyl acrylate, ethyl acrylate, and 2-ethylhexyl acrylate.

Also suitable, in particular, are mixtures of the (meth) acrylic acid alkyl esters.

Vinyl esters of carboxylic acids having 1 to 20 carbon atoms are, for example, vinyl laurate, vinyl stearate, vinyl propionate, and vinyl acetate.

Suitable vinylaromatic compounds are vinyltoluene, alpha- and p-methylstyrene, alpha-butylstyrene, 4-n-butylstyrene, 4-n-decylstyrene and, preferably, styrene.

Examples of nitriles are acrylonitrile and methacrylonitrile.

The vinyl halides are chloro-, fluoro- or bromo-substituted ethylenically unsaturated compounds, preferably vinyl chloride and vinylidene chloride.

Nonaromatic hydrocarbons having 2 to 8 carbon atoms and one or two olefinic double bonds include butadiene, isoprene, and chloroprene, and also ethylene, propylene, and isobutylene.

The principal monomers (IIIa) are also, preferably, used in a mixture.

Vinylaromatic compounds such as styrene are, for example, frequently used in a mixture with $C_1$-$C_{20}$ alkyl (meth)acrylates, in particular with $C_1$-$C_8$ alkyl (meth)acrylates, or with nonaromatic hydrocarbons such as isoprene or, preferably, butadiene.

Suitable monomers (IIIb) are preferably (meth)acrylic acid or maleic acid.

Examples of suitable monomers (IIIc) include the following: esters of acrylic and methacrylic acid with alcohols having 1 to 20 carbon atoms, containing as well as the oxygen atom in the alcohol group at least one further heteroatom and/or an aliphatic or aromatic ring, such as 2-ethoxyethyl acrylate, 2-butoxyethyl(meth)acrylate, dimethylaminoethyl (meth)acrylate, diethylaminoethyl (meth)acrylate, (meth) acrylic aryl, alkaryl or cycloalkyl esters, such as cyclohexyl (meth)acrylate, phenylethyl (meth)acrylate, phenylpropyl (meth)acrylate, or acrylic esters of heterocyclic alcohols, such as furfuryl (meth)acrylate.

Also suitable as monomer (IIIc) are monomers having amino groups or amide groups, such as (meth)acrylamide, and derivatives thereof substituted on the nitrogen by $C_1$-$C_4$ alkyl.

Of particular importance as monomers (IIIc) are hydroxyfunctional monomers, e.g., (meth)acrylic acid $C_1$-$C_{15}$ alkyl esters substituted by one or two hydroxyl groups. Of particular importance as hydroxy-functional comonomers are (meth)acrylic acid $C_2$-$C_8$ hydroxyalkyl esters, such as n-hydroxyethyl, n-hydroxypropyl or n-hydroxybutyl (meth)acrylate.

The polymer (PII) is prepared by free-radical polymerization. Appropriate methods of polymerization, such as bulk, solution, suspension, or emulsion polymerization, are known to the skilled worker.

The copolymer is preferably prepared by solution polymerization with subsequent dispersion in water or, with particular preference, by emulsion polymerization.

In the case of emulsion polymerization the comonomers can be polymerized as usual in the presence of a water-soluble initiator and an emulsifier at preferably from 30 to 95° C.

Examples of suitable initiators are sodium, potassium and ammonium persulfate, tert-butyl hydroperoxides, water-soluble azo compounds, or redox initiators.

Examples of emulsifiers used are alkali metal salts of relatively long-chain fatty acids, alkyl sulfates, alkyl sulfonates, alkylated arylsulfonates or alkylated biphenyl ether sulfonates. Further suitable emulsifiers are reaction products of alkylene oxides, especially ethylene oxide or propylene oxide, with fatty alcohols or fatty acids or with phenols, or alkylphenols.

In the case of aqueous secondary dispersions, the copolymer is first prepared by solution polymerization in an organic solvent and is then dispersed in water with the addition of salt formers, e.g., ammonia, to carboxyl-containing copolymers, without the use of an emulsifier or dispersing auxiliary. The organic solvent may be removed by distillation. The preparation of aqueous secondary dispersions is known to the skilled worker and is described, for example, in DE-A-37 20 860.

To adjust the molecular weight it is possible to use regulators during the polymerization. Suitable examples are —SH-containing compounds such as mercaptoethanol, mercaptopropanol, thiophenol, thioglycerol, ethyl thioglycolate, methyl thioglycolate, and tert-dodecyl mercaptan; they can be used additionally, for example, in amounts of from 0 to 0.5% by weight, based on the copolymer.

The nature and amount of the comonomers are preferably chosen such that the resulting copolymer has a glass transition temperature of from −60 to +140° C., preferably from −60 to +100° C. The glass transition temperature of the copolymer is determined by means of differential thermal analysis or differential scanning calorimetry in accordance with ASTM 3418/82.

The number-average molecular weight, $M_n$, is preferably from $10^3$ to $5\times10^6$, with particular preference from $10^5$ to $2\times10^6$ g/mol (as determined by gel permeation chromatography using polystyrene as standard).

The polymers (P) may further comprise (polymers PIV) a water-dispersible polyester which carries carboxyl groups.

The water-dispersible polyesters which carry carboxyl groups (polymer IV) are known, for example, from Encyclopedia of Polymer Science and Engineering, John Wiley & Sons, Second Edition, Volume 12, pages 300 to 313.

The aqueous dispersions comprising the polymer (P) usually have a solids content of from 10 to 70% by weight.

In a preferred embodiment, carboxyl groups on the polymer (P) react with carbodiimides to form N-acyl urea crosslinks according to the reaction shown below.

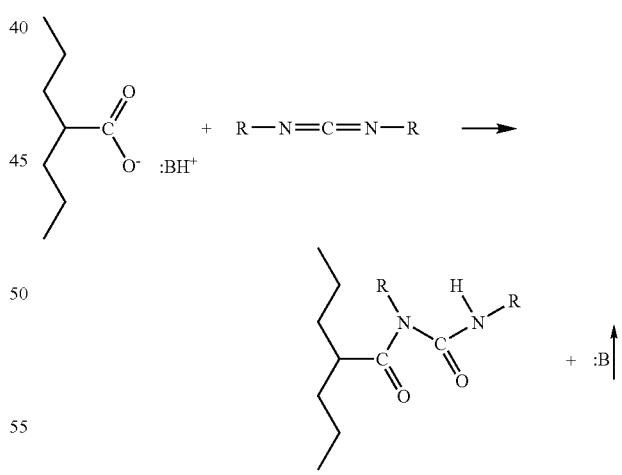

In the above reaction, the carboxylic acid is neutralized with a fugitive base. The neutralization allows for the carbodiimide to be added to the composition to provide a one component composition. Because the carboxylic acid is neutralized, crosslinking reactions are minimized until crosslinking is desired. When the composition is formed into a film, the fugitive base is driven off, either at the use temperature or at an elevated temperature. With the base removed, the carboxyl group reacts with the carbodiimide. Alternatively, the carboxylic acid does not need to be neutralized, but the carboxyl containing latex and the carbodiimide are kept in separate components to prevent premature crosslinking until ready to use.

Fugitive bases that can be used include, but are not limited to, ammonia, ammonium hydroxide, amines, including oligo-amines, ethoxylated amines, and silyl amines.

As used throughout, the amount of carbodiimide used in blends with the polymer is reported in mol % based on the number of carbodiimide groups that can react with carboxyl groups in the polymer. The amount of carbodiimide can be any amount that provides desired results. In a preferred embodiment, the amount of carbodiimide is present in an amount from about 10 to about 500 mol %, and more preferably present in an amount from about 25 to about 250 mol %.

In a preferred embodiment, the carbodiimide has the following structure:

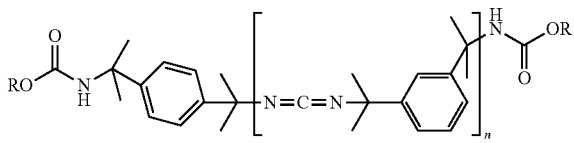

wherein n=1 to 20; R=—$(CH_2CH_2O)_xCH_3$ or R=50% —$(CH_2CH_2O)_yCH_3$/50% —$(CH_2CH_2O)_zCH_3$ wherein x=1 to 20, y=1 to 10, and z=1 to 20.

In other preferred embodiments, the carbodiimide is represented by at least one of the following structures:

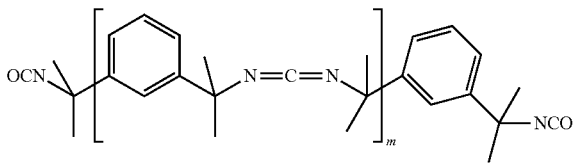

wherein m is from 1 to 20, and preferably m is 4;

carboxyl group in the polymer. The carboxyl group can be placed in the polymer so that a majority or all of the carboxyl group is i) in the core, ii) in the shell, or iii) distributed throughout the polymer. The distribution can be achieved by the time of addition of the carboxyl group.

The carboxyl group can be distributed throughout the polymer by polymerizing a single monomer mixture that contains the carboxyl group containing monomer, or by including the carboxyl group containing monomer in each stage of polymerization. The carboxyl group can be placed in different sections of the polymer by using a multi-stage polymerization process or a gradient feed process. To place a majority or all of the carboxyl group in the core, a carboxyl group containing monomer is included with a first monomer mixture and reacted. One or more subsequent reaction steps with other monomer mixtures can use a lesser amount or none of the carboxyl group containing monomer. Likewise, the carboxyl group containing monomer can be placed in the shell of the polymer by including most or all of the carboxyl group containing monomer in the last stage of polymerization. In a gradient feed process, at least two monomer feeds are supplied to a reactor. At least one of the monomer feeds increases its flow rate during the reaction, and at least one of the monomer feeds decreases its flow rate during the reaction. This changes the composition of the monomers available for reaction throughout the reaction process. The total amount of the carboxyl group can be divided between the different monomer feeds so that the carboxyl group can be distributed differently throughout the reaction product.

Carboxyl group containing monomers can be any ethylenically unsaturated carboxylic acid. Examples of these acids include, but are not limited to, (meth)acrylic acid, maleic acid, fumaric acid, itaconic acid, ethacrylic acid, crotonic acid, citraconic acid, cinnamic acid, phthalic acid, isophthalic acid, terephthalic acid, tetrahydrophthalic acid, hexahydrophthalic acid, tetrabromophthalic acid, trimellitic acid, pyromellitic acid, 1,4,5,6,7,7-hexachloro-5-norbornene-2,3-dicarboxylic acid, succinic acid, 2,6-naphthalenedicarboxylic acid, glutaric acid, sebacic acid, azelaic acid, 1,4-cyclohexanedicarboxylic acid, 1,3-cyclohexanedicarbocylic acid,

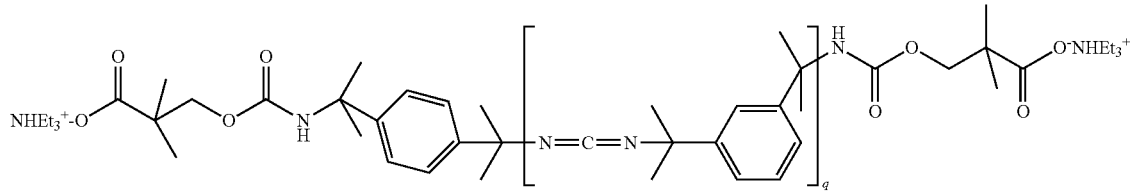

q is from 1 to 20, and preferably q is 4; or

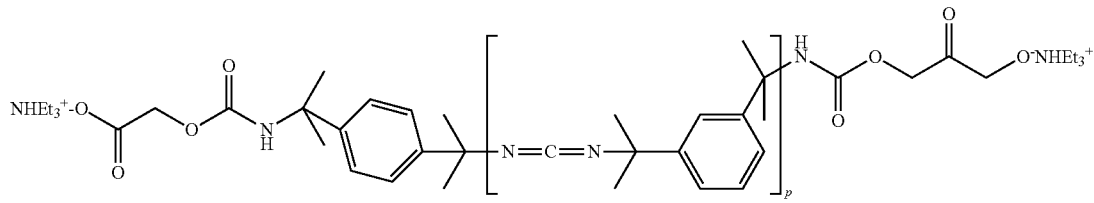

wherein p is from 1 to 20, and preferably p is 4.

The crosslinking of the carboxyl group with the carbodiimide can be changed by changing the distribution of the and combinations thereof. Preferably, the ethylenically unsaturated carboxylic acid is acrylic acid, methacrylic acid, itaconic acid, crotonic acid, or combinations thereof.

Compositions of the present invention that contain a blend of a carboxyl containing polymer and a carbodiimide can provide freeze-thaw stability to the composition. Freeze-thaw stability can be measured by the method described in the Specific Embodiments section below. The number of freeze-thaw cycles that can be obtained for a composition can be controlled by the amount of carbodiimide. The amount of carbodiimide can be any sufficient amount to provide for a desired number of freeze-thaw cycles. In specific examples, 81 mol % or more of carbodiimide can provide for at least four freeze-thaw cycles.

The crosslinking reaction of the carboxyl group containing polymer with the carbodiimide can be initiated by exposure to UV (ultra-violet) radiation. Also, a photoinitiator is not required to initiate UV-induced crosslinking.

Films formed from the composition can have the following properties. Tests for measuring these properties are given below in the Specific Embodiments Section. The film can have a storage modulus G' at 100° C. from about $1 \times 10^3$ to about $1 \times 10^7$ Pa, and preferably from about $1 \times 10^4$ to about $1 \times 10^6$ Pa. The film can have a tensile strength from about $6.89 \times 10^5$ Pa (100 psi) to about $2.07 \times 10^7$ Pa (3000 psi), and preferably from about $1.38 \times 10^6$ Pa (200 psi) to about $1.38 \times 10^7$ Pa (2000 psi). The film can have a % Strain at Break from about 100 to about 2000, and preferably from about 200 to about 1500. The film can have a T2 relaxation time from about 0.5 to about 25 ms, and preferably from about 1 to about 10 ms. The film can have a water absorption of less than about 25%, and preferably less than about 10%. The film can have a water solubles value of less than about 5%, and preferably less than about 2.5%. The film can have a gel content of more than about 5%, and preferably more than about 25%.

The mixtures of the invention comprising compound (V) and polymer (P) may comprise commercially customary auxiliaries and additives such as wetting agents, defoamers, flatting agents, emulsifiers, thickeners and thixotropic agents, and colorants such as dyes and pigments.

They are suitable, for example, for the adhesive bonding or coating of various substrates such as wood, metal, plastic, paper, leather, glass, or textile, for the impregnation of textiles, and for the production of moldings and printing inks.

In these contexts, the dispersions of the invention may be processed by the techniques commonplace in the adhesives, leather or coatings industry, i.e., by spraying, rolling or knife-coating the dispersions onto the substrate and then drying them.

For the case of processing as an adhesive, the coated workpieces are joined to another workpiece, preferably with application of pressure, either before or after the dispersion film has dried.

Particularly strong adhesive bonds are obtained if workpieces that have been provided with a dried adhesive film are heated to a temperature of from about 50 to 100° C. directly before, during, or after joining.

The adhesive bonds produced by these methods are particularly notable for their storage stability and their high thermal stability.

Furthermore, the compounds V may be used to produce adhesive sheets. This is done by blending aqueous dispersions comprising a polymer (PII) or (PIII) with the compound (V). This blend is applied by the customary, abovementioned methods to polymer films, preference being given to corona-treated polyethylene film. The amounts applied are usually from 5 to 6 g/m².

Coated adhesive sheet comprising corona-treated polyethylene film is suitable for sticking to articles of all kinds. If use is made of a sheet of this kind with a mixture of a compound (V) and a polymer (PII) or (PIII) that may be used as a pressure-sensitive adhesive, then the coated sheet is notable in particular for the fact that it can be detached from the substrate without residue along with polymer (PII) or (PIII). The fact that the layer of adhesive formed from polymer (PII) or (PIII) adheres better to the polyethylene film than to the substrate and exhibits high cohesion is something we attribute to the fact that the compound (V) increases the molecular weight of the polymer (PII) or (PIII) and at the same time anchors it to the polyethylene film with the formation of covalent bonds, the carbodiimide groups of the compound (V) probably reacting with those carboxyl groups on the surface of the polyethylene film which come about during the corona treatment.

Adhesive sheets of this kind are therefore particularly suitable for producing labels or for use as protective sheets in order to protect articles, especially those having sensitive surfaces such as coated surfaces or those made of plexiglass, polycarbonate or glass, e.g., screens or windows, against mechanical damage, e.g., scratches, or other environmental influences in the course of storage and transit. They possess the additional advantage that they have a good tack, i.e., the film adheres to the substrate just on contact, without the use of high pressure, e.g., by brushing with the hand or by placing the sheet on the substrate, and can be peeled from the substrate again with moderate force (e.g., using from 1.25 to 2.5 N in the case of an adhesive strip having a width of 25 mm).

Specific Embodiments of the Invention

The invention is further described in the following examples. The examples are merely illustrative and do not in any way limit the scope of the invention as described and claimed.

Example SET 1

Several latexes were prepared and monitored for their ability to crosslink with ELASTOSTAB® H01 and H03 carbodiimide. The latexes were prepared from butyl acrylate (BA), methyl methacrylate, and acrylic acid (AA) or methacrylic acid (MAA). The seed latex used was a proprietary product made by BASF Corp. Four of the latexes have identical compositions (MMA/BA/MAA) and differ only with regard to monomer feed profiles. Thus, the way acid groups were statistically distributed throughout the particle varies. A fifth latex was prepared with AA rather than MAA. A sixth latex was prepared with partially neutralized MAA.

Latex 1: A mixture of 19.14 g of seed and 436.97 g of water were charged into a reaction vessel and mixture was heated to 85° C. An initiator feed, comprised of 4.60 g of sodium persulfate and 87.40 g of water, was charged into the reaction vessel over a period of 3.10 hrs. Two emulsion feeds were fed into the reaction vessel. The first emulsion feed consisted of 244.50 g of water, 30.00 g of TEXAPONG K12 PA15 surfactant, 27.00 g of MAA, 270.00 g of BA, and 243.00 g of MMA. This emulsion was fed over 1.66 hrs. A second emulsion included 244.50 g of water, 30.00 g of TEXAPON® K12 PA15, 270.00 g of BA, and 90.00 g of MMA. This second emulsion was fed over 1.34 hrs. directly after the first emulsion feed. After adding an emulsion flush of 67.50 g of water and cooling to 75° C., the dispersion was post-treated to remove residual monomers. The latex was cooled to room temperature and filtered. The latex was then neutralized with a 29.0% aqueous solution of NH₄OH to a pH of 8.0. Finally, 0.64 g of the biocide KATHON® LX was added to the latex.

Physical Analysis: 44.58% total solids content; final pH=8.0; viscosity=49.6 cps; particle size=149.3 nm.

Latex 2: A mixture of 19.78 g of seed and 436.53 g of water were charged into a reaction vessel and the mixture was heated to 85° C. An initiator feed, comprised of 4.60 g of sodium persulfate and 87.40 g of water, was charged into the reaction vessel over a period of 3.10 hrs. An emulsion feed consisting of 244.50 g of water, 30.00 g of TEXAPON® K12 PA15 surfactant, 27.00 g of MAA, 270.00 g of BA, and 243.00 g of MMA. This emulsion was fed by a ramp feed (initial feed rate: 744.00 g/hr; final feed rate: 0 g/hr.) over 3.00 hrs. A monomer feed, which included 333.00 g MMA, was fed by a ramp feed (initial feed rate: 0.00 g/hr; final feed rate 744.00 g/hr.) over 3.00 hrs. After adding an emulsion flush of 67.50 g of water and cooling to 75° C., the dispersion was post-treated to remove residual monomers. The latex was cooled to room temperature and filtered. The latex was then neutralized with a 29.0% aqueous solution of $NH_4OH$ to a pH of 8.0. Finally, 0.64 g of the biocide KATHON® LX was added to the latex. Physical Analysis: 44.22% total solids content; final pH=8.0; viscosity=44.8 cps; particle size=147.4 nm.

Latex 3: A mixture of 19.14 g of seed and 436.97 g of water were charged into a reaction vessel and the mixture was heated to 85° C. An initiator feed, comprised of 4.60 g of sodium persulfate and 87.40 g of water, was charged into the reaction vessel over a period of 3.10 hrs. One emulsion feed was fed into the reaction vessel. The emulsion feed consisted of 489 g of water, 60.00 g of TEXAPON® K12 PA15 surfactant, 27.00 g of MAA, 540.00 g of BA, and 333.00 g of MMA. This emulsion was fed over 3.00 hrs. After adding an emulsion flush of 67.50 g of water and cooling to 75° C., the dispersion was post-treated to remove residual monomers. The latex was cooled to room temperature and filtered. The latex was cooled to room temperature and filtered. The latex was then neutralized with a 29.0% aqueous solution of $NH_4OH$ to a pH of 8.0. Finally, 0.64 g of the biocide KATHON® LX was added to the latex. Physical Analysis: 44.06% total solids content; final pH=8.0; viscosity=43.2 cps; particle size=151.6 nm.

Latex 4: A mixture of 19.14 g of seed and 436.97 g of water were charged into a reaction vessel and the mixture was heated to 85° C. An initiator feed, comprised of 4.60 g of sodium persulfate and 87.40 g of water, was charged into the reaction vessel over a period of 3.10 hrs. Two emulsion feeds were fed into the reaction vessel. The first emulsion feed consisted of 244.50 g of water, 30.00 g of TEXAPON® K12 PA15 surfactant, 18.00 g of MAA, 270.00 g of BA, and 243.00 g of MMA. This emulsion was fed over 1.66 hrs. A second emulsion included 244.50 g of water, 30.00 g of TEXAPON® K12 PA15 surfactant, 9.00 g of MAA, 270.00 g of BA, and 90.00 g of MMA. This second emulsion was fed over 1.34 hrs. directly after the first emulsion feed. After adding an emulsion flush of 67.50 g of water and cooling to 75° C., the dispersion was post-treated to remove residual monomers. The latex was cooled to room temperature and filtered. The latex was then neutralized with a 29.0% aqueous solution of $NH_4OH$ to a pH of 8.0. Finally, 0.64 g of the biocide KATHON® LX was added to the latex. Physical Analysis: 44.25% total solids content; final pH=8.0; viscosity=42.4 cps; particle size=148.7 nm.

Latex 5: A mixture of 19.14 g of seed and 436.97 g of water were charged into a reaction vessel and the mixture was heated to 85° C. An initiator feed, comprised of 4.60 g of sodium persulfate and 87.40 g of water, was charged into the reaction vessel over a period of 3.10 hrs. One emulsion feed was fed into the reaction vessel. The emulsion feed consisted of 489 g of water, 60.00 g of TEXAPON® K12 PA15 surfactant, 27.00 g of AA, 540.00 g of BA, and 333.00 g of MMA. This emulsion was fed over 3.00 hrs. After adding an emulsion flush of 67.50 g of water and cooling to 75° C., the dispersion was post-treated to remove residual monomers. The latex was cooled to room temperature and filtered. The latex was cooled to room temperature and filtered. The latex was then neutralized with a 29.0% aqueous solution of $NH_4OH$ to a pH of 8.0. Finally, 0.64 g of the biocide KATHON® LX was added to the latex. Physical Analysis: 44.20% total solids content; final pH=8.0; viscosity 43.0 cps; particle size=151.5 nm.

Latex 6: A mixture of 19.14 g of seed and 436.97 g of water were charged into a reaction vessel and the mixture was heated to 85° C. An initiator feed, comprised of 4.60 g of sodium persulfate and 87.40 g of water, was charged into the reaction vessel over a period of 3.10 hrs. Two emulsion feeds were fed into the reaction vessel. The first emulsion feed consisted of 244.50 g of water, 30.00 g of TEXAPON® K12 PA15 surfactant, 18.00 g of MAA, 270.00 g of BA, 1.67 g of NaOH and 243.00 g of MMA. This emulsion was fed over 1.66 hrs. A second emulsion included 244.50 g of water, 30.00 g of TEXAPON® K12 PA15 surfactant, 9.00 g of MAA, 270.00 g of BA, 0.84 g of NaOH, and 90.00 g of MMA. This second emulsion was fed over 1.34 hrs. directly after the first emulsion feed. After adding an emulsion flush of 67.50 g of water and cooling to 75° C., the dispersion was post-treated to remove residual monomers. The latex was cooled to room temperature and filtered. The latex was then neutralized with a 29.0% aqueous solution of $NH_4OH$ to a pH of 8.0. Finally, 0.64 g of the biocide KATHON® LX was added to the latex. Physical Analysis: 43.47% total solids content; final pH=8.0; viscosity=36.0 cps; particle size=151.2 nm.

Latex 7: Latex 6 was repeated, except that ammonium hydroxide was used to buffer the pre-emulsion instead of sodium hydroxide. This allowed more acid groups to be pulled closer to the particle surface, but it did no place more acid groups in the serum. Using a fugitive base made all of the acid groups accessible.

A compositional ladder study was conducted to investigate the effects that varying amounts of ELASTOSTAB® H01 and H03 carbodiimide crosslinking agents had on the physical properties of latex films 1, 2, and 4. Blends were prepared with the assumption that all MAA groups in the latex (0.15 M) were accessible for crosslinking. The amount of ELASTOSTAB® carbodiimide added was with regard to the mole % of the diimide functionality that can react with the MAA.

Each of the latexes mentioned above were prepared a second time, but were not buffered with base in the final stages of the polymerization. These acidified latexes with a pH ca. 2.3 were used in the determination of surface acid groups by potentiometric titration. Before the titration was performed, the latex was first cleaned of any water soluble low molecular weight salts (remnants of surfactant or initiator groups) or oligomers from the latex serum. This procedure was explained in more detail below.

The kinetics of the crosslinking reaction between the carboxylic acid and oligocarbodiimide groups were monitored by following the disappearance of the —N=C=N— group using Fourier Transform Infrared (FTIR). The latex/ELASTOSTAB® carbodiimide blends were applied as films deposited on ZnSe plates and allowed to dry for ca. 10 min. prior to performing the study. The decreasing nature of the intensity of the —N=C=N— band between 2160-2180 cm was integrated and weighted against the integrated intensities of the C—H stretching bands (3050-2800 $cm^{-1}$), which remained constant throughout the course of the crosslinking reaction.

All FTIR measurements were performed on a NICOLET Model 520P Infrared Spectrometer with a resolution of 4.0 $cm^{-1}$.

Dynamic Mechanical Analyses (DMA) were performed on the crosslinked films using a Rheometric Scientific ARES spectrometer, equipped with an 8 mm parallel plate system. Measurements were recorded with a torsional load at a frequency of 1 rad/s and within a temperature range from −25° C. to 250° C. The heating rate for this process was 5.0° C./min. Tensile tests were carried out on an INSTRON 4505 with a 10 kg (22 lb.) Load cell. The tensile tests were performed according to an internal standard procedure. The crosshead speed was set to 20 cm (7.9 inches)/min for the duration of the test.

Particle size measurements were performed on a NICOMP 308 Submicron Particle Sizer. They were determined by dynamic light scattering at an angle of 90° and at 25° C.

Water absorption and solubles tests were performed on films of latexes 1, 2, and 4 and their respective blends with ELASTOSTAB® EH01 and EH03 carbodiimide. The films were allowed to cure for five days at 60° C. Three square specimens of each film were cut out to weights ~1.80 g. The samples were then placed between two stainless steel screens and immersed into water for a period of 24 hours. The samples were subsequently removed from the water, blotted dry with a towel, and weighed. The samples were allowed to then dry under constant temperature (73° C.) and humidity (50% RH) conditions for 72 hours and reweighed.

Serum replacement and titration of acidified latexes 1, 2, and 4.—Each latex was diluted to 0.5% with MILLAPORE® Filter water (conductivity=1.8 μs) to give 500 ml of dispersion. Two aliquots of 100 ml were titrated with a 0.001M NaOH solution to determine the combined amount of acid groups in the latex serum and on the latex particle surface. The remaining 300 ml of the dispersion were placed into a NUCLEOPORE Stirred Cell Membrane Diafiltration System in which the serum of the diluted latex was replaced with MILLAPORE® filtered water. The ultrafiltration membrane used in this process was the BIOMAX® polyethersulfone PBVK membrane from Millipore Corp., which had a normal molecular weight limit (NMWL) selectivity of 500,000 g/mol. Filters with NMWL selectivities of 100,000 and 1,000,000 g/mol have been determined to have corresponding pore sizes of 0.0062 and 0.0132 microns, respectively. The serum exchange rate was 2.5 mL/min and the conductivity of the filtrate during the dialysis was monitored until it reached the value of the MILLAPORE® water itself. Once the conductivity reached the value of the MILLAPORE® purified standard, it was assumed that the serum had been replaced; however, the dialysis was left to run for another 6 hrs after reaching this stage to ensure all low molecular weight acid groups were removed. After the dialysis was complete, two 100 ml aliquots of this dispersion were titrated with a 0.001 M NaOH solution to determine the amount of acid groups on the latex particle surface alone. The 0.001 M NaOH solution used to perform these titrations was calibrated by titrating it against a $1.38 \times 10^{-4}$ M of methacrylic acid.

The reaction profiles of latexes 1-6 along with their resulting physical properties are shown in Table 0.

TABLE 0

| Experimental Latex | 1 | 2 | 3 | 4 | 5 | 6 |
|---|---|---|---|---|---|---|
| Reaction Temperature | 85° C. | 85° C. | 85° C. | 85° C. | 85° C. | 85° C. |
| Emulsion Step #1 | | | | | | |
| Water | 244.5 g | 489.0 g | 489.0 g | 244.5 g | 244.5 g | 244.5 g |
| TEXAPON K12PA15 | 30.0 g | 60.0 g | 60.0 g | 30.0 g | 30.0 g | 30.0 g |
| Methacrylic acid | 27.0 g | 27.0 g | 27.0 g | 18.0 g | 18.0 g | 18.0 g |
| Acrylic acid | | | | | | |
| Butyl Acrylate | 270.0 g | 540.0 g | 540.0 g | 270.0 g | 270.0 g | 270.0 g |
| Methyl Methacrylate | 243.0 g | | 333.0 g | 243.0 g | 243.0 g | 243.0 g |
| NaOH | | | | | | 1.67 g |
| Feed Time | 1.70 hrs | 3.00 hrs | 3.00 hrs | 1.70 hrs | 3.00 hrs | 1.70 hrs |
| Feed Type | Constant | Gradient | Constant | Constant | Constant | Constant |
| Initial Feed Rate | 479 g/hr | 744 g/hr | 483 g/hr | 485 g/hr | 483 g/hr | 486 g/hr |
| Final Feed Rate | 479 g/hr | 0 g/hr | 483 g/hr | 485 g/hr | 483 g/hr | 486 g/hr |
| Emulsion Step #2 | | | | | | |
| Water | 244.5 g | | | 244.5 g | | 244.5 g |
| TEXAPON K12PA15 | 30.0 g | | | 30.0 g | | 30.0 g |
| Methacrylic acid | | | | 9.00 g | | 9.00 g |
| Butyl Acrylate | 270.0 g | | | 270.0 g | | 270.0 g |
| Methyl Methacrylate | 90.0 g | 333.0 g | | 90.0 g | | 90.0 g |
| NaOH | | | | | | 0.84 g |
| Feed Time | 1.30 hrs | 3.00 hrs | | 1.30 hrs | | 1.30 hrs |
| Feed Type | Constant | Gradient | | Constant | | Constant |
| Initial Feed Rate | 488 g/hr | 0 g/hr | | 480 g/hr | | 481 g/hr |
| Final Feed Rate | 488 g/hr | 744 g/hr | | 480 g/hr | | 481 g/hr |
| Physical Properties | | | | | | |
| Theoretical Solids Content | 43.9% | 43.9% | 43.9% | 43.9% | 43.9% | 43.9% |
| Actual Solids Content | 44.6% | 44.2% | 44.1% | 44.2% | 44.2% | 43.5% |
| Final pH (adjusted) | 8.0 | 8.0 | 8.0 | 8.0 | 8.0 | 8.0 |

TABLE 0-continued

| Experimental Latex | 1 | 2 | 3 | 4 | 5 | 6 |
|---|---|---|---|---|---|---|
| Viscosity | 49.6 cps | 44.8 cps | 43.2 cps | 42.4 cps | 43.0 cps | 36.0 cps |
| Particle Size (Vol. Ave.) | 149.3 nm | 147.4 nm | 151.6 nm | 148.7 nm | 151.5 nm | 151.2 nm |
| MFFT | <0° C. | <0° C. | <0° C. | <0° C. | <0° C. | <0° C. |

Each of the latexes exhibits a unique statistical distribution of acid groups throughout their relevant particles despite having practically identical ingredient compositions. By varying the location and density of the acid groups, crosslinking can be maximized, and the resulting mechanical properties of the film can be controlled.

Latexes 1-6 were designed with the intention that the amount of peripheral carboxyl groups would increase with respect to the progression of order with latex 1 having the most hydrophobic exterior and latex 6 having the most hydrophilic exterior. Latex 1 was prepared with a two stage emulsion feed in which the entire amount of MAA (3 pphm) was added during the first stage and consequently no acid was added in the second stage. The second latex, 2, was prepared with separate gradient feeds of MMA and BA/MAA throughout the reaction such that the relative concentration of MMA in the feed increased from 0% to 100% over the course of the reaction while the proportion of BA and MAA decreased from 100% to 0%. For latex 3, the 3 pphm of MAA were added throughout the course of the single stage emulsion feed (3 hrs.). Latex 4 was prepared with a two stage emulsion feed, but differed from 1 in that 2 pphm of MAA were added during the first stage (1.66 hrs) and 1 pphm of MAA was added during the second stage (1.33 hrs) of the polymerization. Latex 5 was prepared analogous to 3 but AA was substituted for MAA as the functional acid. The experimental procedure for latex 6 was similar to latex 4 with the exception that both of the feeds were buffered during the emulsion polymerization. Thus, for the six latexes prepared, the amount of acid groups at the surface of the particle and in the serum for each distinctive latex was expected to follow the trend:

Latex 1<Latex 2<Latex 3<Latex 4<Latex 5<Latex 6.

The loss modulus (G") for latexes 1 and 2 seen in FIG. 1 clearly shows the effect of reaction feed on particle morphology. In latex 1, two distinct phases were observed for the "acid rich" interior and "acid deficient" exterior of the latex particle at temperature values of 39.22 and −6.57° C. respectively. While in latex 2, the partition of these phases was nonexistent due to the nature of the monomer gradient feed during the reaction in which no individual domains form, but rather a continuously changing composition of increasing $T_g$ resulted.

Through the results of the titration with NaOH given in Table 1, we were able to experimentally determine the amount of acid groups in the latex serum, particle-serum interface, and particle interior. In spite of the differences in acid monomer type and feeding profile, there was no great discrepancy between the first five experimental latexes in terms of the amount of acid groups titrated in the serum and particle interface. Even the exchange of acid monomer from MAA to AA showed only a minor alteration of the acid group content at the particle interface. Latex 6, however, which was buffered throughout the two stage reaction run, exhibited an increase in the amount of acid groups on the particle interface by almost 300% relative to latex 4.

This created a scenario in which to evaluate the competition between film formation and crosslinking. By having nearly equal concentrations of acid groups in the serum or particle surface of the different latexes, the influence of acid distribution in the interior of the particle could be explored. The following discussion details how static and dynamic mechanical property measurements were coupled with spectroscopic data and kinetic crosslinking studies to evaluate the nature of the carboxyl distribution in the particle interior of the various latex samples.

TABLE 1

| | 1 | 2 | 3 | 4 | 5 | 6 |
|---|---|---|---|---|---|---|
| Total moles of -COOH in latex sample | 0.15 moles | 0.15 moles | 0.15 moles | 0.15 moles | 0.18 moles | 0.15 moles |
| Mole % of -COOH observed on particle surface and serum | 13.96 ± 0.27 | 13.82 ± 0.39 | 10.77 ± 0.18 | 14.27 ± 0.53 | 11.89 ± 0.33 | 25.10 ± 0.65 |
| Mole % of -COOH on latex particle interface | 6.89 ± 0.33 | 6.85 ± 0.39 | 6.07 ± 0.36 | 7.25 ± 0.29 | 5.67 ± 0.22 | 18.37 ± 1.42 |
| Mole % of -COOH in latex serum | 7.07 ± 0.44 | 6.98 ± 0.54 | 4.69 ± 0.40 | 7.01 ± 0.60 | 6.21 ± 0.43 | 6.73 ± 0.75 |
| Mole % of COOH in particle interior | 86.04 ± 0.27 | 86.17 ± 0.39 | 89.21 ± 1.82 | 85.73 ± 0.53 | 88.11 ± 0.33 | 74.90 ± 0.65 |

Tensile tests were performed to investigate the difference in mechanical properties of experimental latex films 1, 2, and 4 and how varying amounts of ELASTOSTAB® H01 or H03 carbodiimide affected the physical properties of these films. The stress-strain curves for films 1, 2, and 4 along with their EH01 and EH03 blends were shown in FIG. 2. The results of the tensile tests presented in Tables 2 and 3 and observation of the graphs in FIG. 2 suggest latexes 1 and 4 have relatively similar behaviors, although some differences were evident especially when comparing their respective EH01 and EH03 blends. Due to the nature of the process conditions during the emulsion polymerization, the exterior of latex 4 should be more enriched with acid groups than 1. A comparison of the stress-strain curves of the 109 mol % EH01 blends of 4 and 1 indicates that nonuniform and incomplete crosslinking occurred in both cases. Film strength was reduced when EH01 was present. Reduced film strength after a relatively short cure time was expected since the water solubility of EH01 rendered particle-particle welding initially as carbodiimide groups reacted with carboxylic acid groups at the particle interfaces in the early stages of film formation. Further evidence of this behavior was shown by the fact that EH01 appeared to have less of an effect on latex 4 than 1 because of the tendency of EH01 to prematurely crosslink with the prior's more acid-enriched exterior before adequate polymer interdiffusion took place.

In contrast, EH03 increased the film strength of 4, but had only a slight effect on 1. This behavior was attributed to the distinctive solubility of EH03, a portion of which, unlike the EH01, would diffuse into the latex particle prior to film formation. The acid groups of latex 4 were more evenly distributed throughout the particle. In contrast, latex 1 has fewer carboxyl groups toward the exterior. Hence, crosslinking should be more uniform in latex 4, while the crosslinking density should be concentrated toward the particle interior of latex 1 upon diffusion of and reaction with EH03. The gel content reported in Table 6 supports this. In both latexes 1 and 4, the crosslinking appeared to be more uniform with EH03 than the respective EH01 blends.

Latex 2 deviated from the behaviors of 1 and 4 due to the gradient feed of the monomers, MMA and MAA, during the emulsion polymerization. According to the feed profile, the number of MMA units on the polymer backbone should increase as the particle radius increases, while the relative proportion of MAA should decrease. The MMA enriched exterior of the latex particle resulted in relatively less interdiffusion of higher $T_g$ polymer and hence, a plastic film was formed with a lower yield stress and plastic deformation in the stress-strain curve of 2. In contrast, latexes 1 and 4 have exteriors enriched with a soft monomer, BA, which helped promote interparticle diffusion. Amazingly, latex 2 still has an MFFT below 0° C. in spite of the harder particle exterior.

The EH01 and EH03 blends of 2 (109 mol % and 100 mol % respectively) showed an increase in tensile strength and a decrease in elongation. This result was attributed to the "gradient" concentration of carboxyl groups from the center of the latex particle core (high density) to the exterior of the particle (low density). While the amount of acid groups toward the exterior of 2 was enough to cause some crosslinking, there was still enough molecular mobility to promote particle interdiffusion between adjacent exteriors. Since the $T_g$ of the exterior portions of the particle was already very high, however, polymer diffusion was quickly limited as crosslinking proceeded. Interestingly and in contrast to latex 4, in which EH03 exhibited crosslinking while EH01 did not, the combination of either EH03 or EH01 with latex 2 resulted in crosslinking. Indeed, with latex 2, the diffusion of EH03 toward the carboxyl-rich particle interior greatly increased crosslink density resulting in the very brittle tensile behavior depicted in FIG. 2. The higher water solubility of EH01 prevented its early entry into the particle resulting in a somewhat lesser strength crosslinked film. The nonuniform nature of the particle crosslinking coupled with a relatively higher $T_g$ polymer closer to the particle boundary yielded very brittle film behavior.

Both single-stage latexes 3 and 5 produced films of lower strength compared to latexes 1 and 4. The primary reason for the difference (especially in the case of latex 3, which was compositionally identical to latexes 1 and 4) was the fact that latexes 1 and 4 have a higher $T_g$ first phase and a lower $T_g$ second phase. The higher $T_g$ first phase created a stiffer, higher modulus film, while the softer second phase promoted film formation. The single phase Fox $T_g$ of latexes 3 and 5 was about 15° C. lower than the first phase $T_g$ and about 20° C. higher than the second phase $T_g$ of latexes 4 and 1.

Additional evidence was seen in the stress strain curves for EH01 and EH03 blends of latexes 3 and 5. Neither EH01 nor EH03 greatly improved the mechanical properties of Latex 3. However, the EH01 and EH03 blends of latex 5 both showed more extensive crosslinking. Although crosslinking of 5 with EH01 resulted in a strong film, properties were further enhanced with EH03, which was more compatible with the polymer phase due to increased hydrophobicity. The substitution of AA for MAA in latex 5 created higher modulus due to more extensive crosslinking compared to latex 3. Without being limited to theory, the solubility of AA and the kinetics of AA copolymerization were presumed to account for these differences.

Latex 6 had an identical composition and feed profile as 4; however, in latex 6 during both stages of the emulsion polymerization, the acid groups were partially buffered with NaOH. Partial ionization of the acid groups drove them to the particle surface; indeed, 25% of the MAA was found at the particle surface according to titration measurements. The modulus of latex 6 was significantly higher than latex 4. The effect of metal counter ion carboxylates on acrylate copolymer mechanical property improvement is well known. The addition of EH01 and EH03 to latex 6 did not provide results as good as the other latexes due to the number of acid groups that remained ionized by sodium ions following the drying stage. This limited the number of —COOH groups that could participate in the carbodiimide crosslinking reaction. Indeed, EH01 acted more like a diluent since most of the acid groups near the particle surface were ionized metal cations. EH03 had a negligible effect on the tensile strength of 6 again due to the fact that many acid groups remained permanently ionized.

In Table 2 the tensile tests clearly show the EH03 carbodiimide provided advantages over its EH01 counterpart. Again, this was primarily due to the ability of the EH03 derivative to partially diffuse into the latex particle and react with acid groups in the interior of the particle. Overall, the dispersions containing approximately 100 mol % of EH03 with respect to the latex acid content achieved the highest degree of crosslinking and thus the maximum enhancement of physical properties. This trend was evident when observing the compositional ladder study of all three latex blends shown in Table 3, but was especially evident for latexes 2 and 4. The morphology of latex 1 gives rise to fewer acid groups near the surface. Even though EH03 was partially compatible with the polymer phase, the concentration of acid groups only in the "core" of latex 1 resulted in the shell not being crosslinked. At early stages of polymer interdiffusion, little crosslinking occurred and yet high gel content builds in the interior of the particles gave rise to a smaller increase in film strength relative to latex 4. For latexes 2 and 4, a relatively large tensile strength increase was observed even at 33 mol % addition of EH03. In the case of latex 2, the modulus was dramatically enhanced with lower amounts of crosslinking due to the much higher $T_g$ near the extremity of the particle. This led, however, to embrittlement of the film and an overall lower film energy (the area underneath the stress strain curve) compared to latex 4, which exhibited an increase in tensile strength without much decrease in elongation giving rise to overall higher film energy.

Amounts of either EH01 or EH03 exceeding 100 mol % gave a reduction of the polymer's physical properties due to plasticization by ethoxylated groups on the carbodiimide. Latex blends exceeding 100 mol % EH01 or EH03 were prepared to test an unequal reactivity hypothesis that assumed successive carbodiimide groups react more slowly during crosslinking as additions occur along the oligomer chain. Therefore, the calculated stoichiometric values of the carbodiimide would not necessarily be the amounts needed to fully crosslink all the acid groups of the latex particle.

TABLE 2

| Sample | Tensile Strength Pa (x $10^6$) (psi) | % Strain @ break |
|---|---|---|
| Latex 1 | 5.76 ± 0.2806 | 516.283 ± 37.749 |
|  | 835.392 ± 40.701 |  |
| 109% EHO1 | 4.655 ± 0.4717 | 535.984 ± 49.015 |
|  | 675.153 ± 68.413 |  |
| 100% EHO3 | 6.457 ± 0.647 | 522.198 ± 43.442 |
|  | 936.533 ± 93.970 |  |
| Latex 2 | 1.843 ± 0.2514 | 1033.757 ± 240.185 |
|  | 267.304 ± 36.462 |  |
| 109% EHO1 | 5.19 ± 0.1385 | 371.460 ± 19.992 |
|  | 752.768 ± 20.086 |  |
| 100% EHO3 | 7.84 ± 0.433 | 323.898 ± 24.527 |
|  | 1137.082 ± 62.802 |  |
| Latex 4 | 5.534 ± 0.3412 | 608.508 ± 14.424 |
|  | 802.656 ± 49.480 |  |
| 109% EHO1 | 3.284 ± 0.5532 | 538.616 ± 51.603 |
|  | 476.315 ± 80.241 |  |
| 100% EHO3 | 8.278 ± 0.6179 | 487.568 ± 25.264 |
|  | 1200.650 ± 89.615 |  |

TABLE 3

| Sample | Tensile Strength Pa (x $10^6$) (psi) | % Strain at break |
|---|---|---|
| Latex 1 | 5.76 ± 0.2806 | 516.283 ± 37.749 |
|  | 835.392 ± 40.701 |  |
| 33% EHO3 | 6.814 ± 0.1284 | 517.570 ± 17.747 |
|  | 988.225 ± 18.623 |  |
| 100% EHO3 | 6.457 ± 0.6479 | 522.198 ± 43.442 |
|  | 936.533 ± 93.970 |  |
| 131% EHO3 | 6.496 ± 0.3909 | 605.819 ± 31.276 |
|  | 942.226 ± 56.694 |  |
| 198% EHO3 | 4.656 ± 0.3758 | 608.406 ± 15.841 |
|  | 675.328 ± 54.502 |  |
| Latex 2 | 1.843 ± 0.2514 | 1033.757 ± 240.185 |
|  | 267.304 ± 36.462 |  |
| 33% EHO3 | 4.667 ± 0.2943 | 529.354 ± 39.159 |
|  | 676.913 ± 42.688 |  |
| 100% EHO3 | 7.84 ± 0.433 | 323.898 ± 24.527 |
|  | 1137.082 ± 62.802 |  |
| 131% EHO3 | 7.611 ± 0.2687 | 314.673 ± 13.189 |
|  | 1103.949 ± 38.967 |  |
| 198% EHO3 | 6.175 ± 0.3794 | 280.506 ± 10.789 |
|  | 895.626 ± 55.022 |  |
| Latex 4 | 5.534 ± 0.3411 | 608.508 ± 14.424 |
|  | 802.656 ± 49.480 |  |
| 33% EHO3 | 6.548 ± 0.8655 | 554.472 ± 49.746 |
|  | 949.777 ± 125.531 |  |
| 100% EHO3 | 8.278 ± 0.6179 | 487.568 ± 25.264 |
|  | 1200.650 ± 89.615 |  |
| 131% EHO3 | 6.909 ± 0.537 | 536.352 ± 39.260 |
|  | 1002.030 ± 77.885 |  |
| 198% EHO3 | 6.264 ± 0.557 | 513.968 ± 17.197 |
|  | 908.592 ± 80.779 |  |

DMA data of latexes 1, 2, and 4 provided an accurate confirmation of the tensile measurements, which showed the degree of crosslinking increased as the mol % carbodiimide increased up to a stoichiometric level. The relaxation spectra in FIG. 3 show the logarithmic plots of G' as a function of temperature from 50 to 250° C. for the EH01 and EH03 blends of latex 4. Both blends showed the characteristic crosslinking plateau feature in the DMA from 25 to 100° C., which was indicative of carboxylic acid-diimide crosslinking. Within this temperature region, the trend shows that as the amount of diimide was increased over 100 and 109 mol % EH03 and EH01, respectively, the degree of crosslinking diminished. This appeared to be a function of stoichiometry; as more carbodiimide groups were introduced, less carboxylic acid groups react per oligomer. Instead of crosslinking, a simple derivation occurs from acid to an acyl urea/carbodiimide pendant group.

TABLE 4

| | $T_g$ |
|---|---|
| Latex 4 | −24.42° C. |
| 109 mol % EH01 | −2.78° C. |
| 217 mol % EH01 | −11.03° C. |
| 325 mol % EH01 | −17.12° C. |
| 100 mol % EH03 | −5.81° C. |
| 198 mol % EH03 | −5.92° C. |
| 296 mol % EH03 | −7.16° C. |

By looking at Table 4, one can clearly observe the difference in the $T_g$ from the G" data for latex 4 as the EH01 and EH03 supplement was augmented. The EH01 blends in particular showed an interesting trend. With the addition of 109 mol % of EH011, the maximum conversion from acid to acyl urea was attained shown with an increase of the $T_g$ over 20° C. As the amount of EH01 added surpassed 109 mol %, the $T_g$ decreased and approached the $T_g$ value of latex 4 due to plasticization by ethylene oxide units as mentioned before. Unlike the EH01 blends, the $T_g$ of the EH03 blends stayed rather consistent despite the increase in the amount of carbodiimide added. This difference in behavior between the EH01 and EH03 was expected since the EO pendant chain for EH01 was on average longer.

At higher temperature ranges from 150 to 250° C., further crosslinking of unreacted carbodiimide and —COOH occurred during the DMA experiment, especially in blends containing the highest amounts of excess carbodiimide oligomer. Even blends containing less than 100 mol % carbodiimide exhibited additional crosslinking. The behavior observed was a result of the competition between the rates of polymer interdiffusion and crosslinking in which a fraction of carbodiimide functional groups remained unreacted. It would appear that at 25° C., the rate of crosslinking was slow relative to interdiffussion, so that even though there were excess carboxylic acid groups, they did not react during film cure, but rather during the DMA experiment at elevated temperature. Furthermore, such behavior may be evidence of unequal reactivity, i.e., as successive groups on the oligomeric carbodiimide crosslink, the overall rate of the reaction decreased leaving some unreacted diimide groups behind.

To investigate further the competition between film formation and crosslinking, DMA measurements were also made of films that were allowed to cure at higher temperature (5 days; 60° C.) or longer periods of time (90 days; 25° C.). The results of the higher temperature cured films and the results of the film cured over prolonged time can be seen in the graphs of FIG. 4. In both instances, the modulus of the films increased substantially with regard to films cured at ambient temperature during a period of fourteen days. In addition, the differences observed in the DMA measurements of the EH01 and EH03 blends at ambient temperatures were not observed as a film was annealed with time or heat. Table 5 shows the differences of the G' values of latex 4 along with it's EH01 and EH03 blends at different curing conditions. The same degree of crosslinking was achieved for samples measured after a long cure time at 25° C., as for samples more rapidly cured at elevated temperature. This was consistent with the observation that crosslinking was not competitive with interdiffussion at 25° C., but was rapid at higher temperatures (in this case at 60° C.).

TABLE 5

|  | Cured @ 25° C. 14 days | Cured @ 25° C. 90 days | Cured @ 60° C. 5 days |
| --- | --- | --- | --- |
| Latex 4 | $9.64 \times 10^3$ Pa | $3.73 \times 10^4$ Pa |  |
| 109 mol % EH01 | $2.87 \times 10^4$ Pa | $4.85 \times 10^4$ Pa | $5.06 \times 10^5$ Pa |
| 100 mol % EH03 | $3.69 \times 10^4$ Pa | $4.74 \times 10^4$ Pa | $7.85 \times 10^5$ Pa |

T2, gel content and gel swell measurements were performed on the latex film cured at 60° C. for 5 days to compare the extent of crosslinking between the EH01 and EH03 blends of latexes 1, 2, and 4. These measurements can be viewed in Table 6. All data confirm EH03 containing films showed an enhanced degree of crosslinking over the EH01 containing films and correlated with the mechanical data observed in the tensile and DMA measurements. The data were also consistent with the expectation that EH03 was more compatible with the latex particles due to its greater hydrophobicity. The 60° C. curing process makes the crosslinking reaction more competitive with film formation, so that as crosslinking occurs at particle interfaces, interdiffusion slows dramatically due to buildup of molecular weight. Higher crosslink density at particle interfaces resulted from the hydrophilic EH01, while the oligophilic EH03 rendered more uniform crosslinking and therefore higher modulus.

TABLE 6

|  | T2 (ms) | Gel Content % | Gel Swell Index |
| --- | --- | --- | --- |
| Latex 1 | 3.342 | 61.3 | 50.77 |
| 109 mol % EH01 | 3.247 | 80.6 | 8.77 |
| 100 mol % EH03 | 2.917 | 84.7 | 8.51 |
| Latex 2 | 3.014 | 4.1 | 25.09 |
| 109 mol % EH01 | 3.094 | 73.6 | 9.16 |
| 100 mol % EH03 | 2.096 | 78.9 | 6.99 |
| Latex 4 | 3.136 | 58.6 | 43.09 |
| 109 mol % EH01 | 2.993 | 89.7 | 7.29 |
| 100 mol % EH03 | 2.483 | 93.4 | 6.59 |

Water uptake measurements were performed on films that had cured 14 days at 25° C. The water uptake results for latexes 1, 2, and 4 and their respective EH01 and EH03 blends can be observed in Table 7. The water uptake data implied that little crosslinking occurred during film cure under ambient conditions for 14 days. The EH03 blends have similar water absorptions compared to the controls, while the EH01 blends showed higher water absorption than either the standard latex or the EH03 blend. This result can be attributed to the greater solubility of EH01 in water, which makes it more susceptible to water uptake. It was interesting to note that the EH03 blends of latexes 1 and 2 had higher water absorption versus the control than the EH01/latex 4 blend. This again indicates that the acid group enrichment in both phases of latex 4 enhanced crosslinking; whereas, the acid starved extremities of latexes 1 and 2 inhibited crosslinking.

TABLE 7

|  | Water Absorption | Water Solubles |
| --- | --- | --- |
| Latex 1 | 5.81% | 0.29% |
| 109% EH01 | 8.97% | 0.26% |
| 100% EH03 | 7.59% | 0.46% |
| Latex 2 | 5.80% | 0.15% |
| 109% EH01 | 14.60% | 2.18% |
| 100% EH03 | 6.75% | 0.45% |
| Latex 4 | 5.67% | 0.29% |
| 109% EH01 | 9.20% | 0.11% |
| 100% EH03 | 5.50% | 0.19% |

Taken as a whole, the data imply that EH03 provided better properties versus EH01. This was attributed to the solubility differences between the two crosslinkers rather than an absolute difference in chemical reactivity. The kinetics of the crosslinking reaction for the different crosslinkers was studied using IR spectroscopy. From the disappearance of the —N=C=N— band provided by FTIR measurements, it was possible to calculate the rate constants k of the reactions between the EH01 and EH03 diimides separately with the acid groups of latexes 1, 2, and 4 at varying temperatures. From the calculated k values, the activation energies ($E_a$) were obtained by plotting ln k vs $T^{-1}$ for the various blends. Representative Arrhenius plots for the reaction of EH01 or EH03 with each of the three latexes was seen in the graphs in FIG. 5, and the calculated activation energies can be seen in Table 8. The activation energy values shown in the table depend more on the nature of the carbodiimide used than the distribution of acid groups in the latex particle. No difference in reactivity was expected, however, since the reactive portion of each oligomer was identical. Therefore, the data in Table 8 represents apparent activation energies and the values differ because the differences in solubility gave rise to differing proximity of functional groups. Given the slower reactivity of the carbodiimides at room temperature, it was advantageous to design a latex-carbodiimide system that brings reactive groups into close proximity as quickly as possible. In agreement with the data seen thus far with the tensile test and DMA, the EH03 blends were observed to have significantly lower activation energies than their corresponding EH01 blends and therefore were shown to be a more energetically favored oligocarbodiimide for crosslinking.

TABLE 8

|  | ELASTOSTAB ® H01 | ELASTOSTAB ® H03 |
| --- | --- | --- |
| Latex 1 | 49.866 ± 2.477 kJ/mol | 36.942 ± 4.533 kJ/mol |
| Latex 2 | 44.585 ± 3.252 kJ/mol | 37.292 ± 3.858 kJ/mol |
| Latex 4 | 46.770 ± 3.968 kJ/mol | 41.518 ± 2.650 kJ/mol |

Figure 6A:
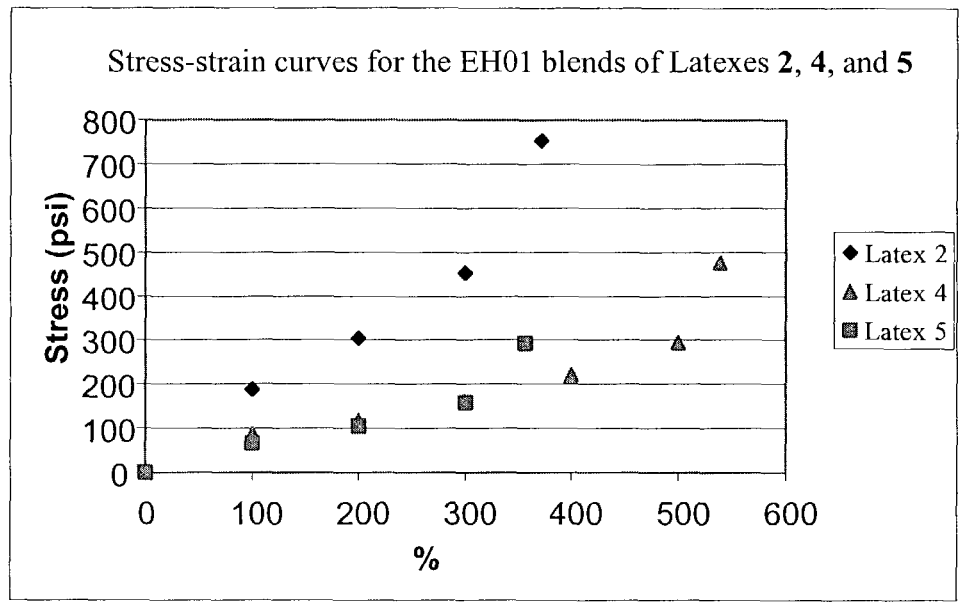
FIGS. 6a and 6b are graphs of stress-strain curves for EH01 and EH03 blends with Latexes 2, 4, and 5.
Figure 6B:
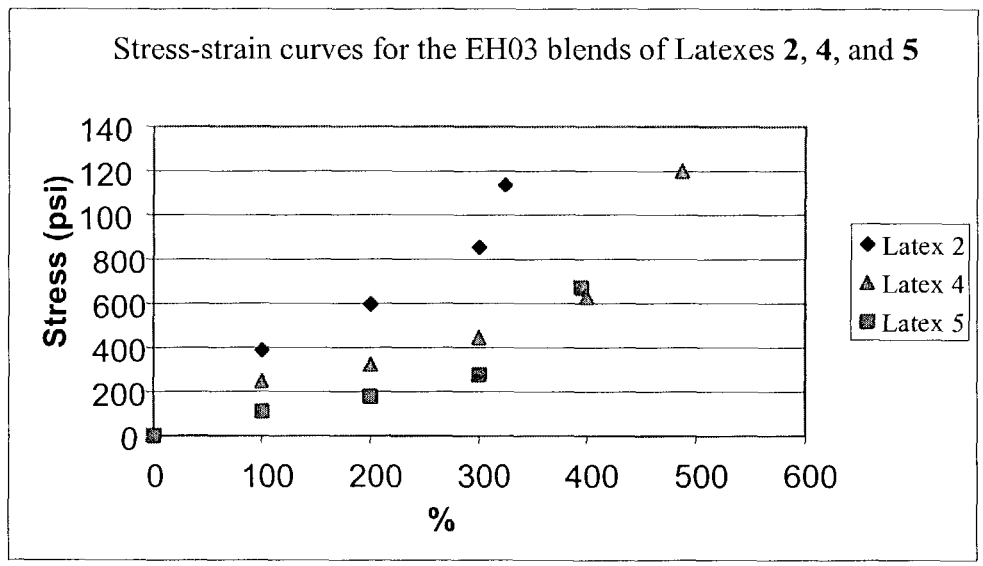

Finally, a comparison was made between the tensile test data of latexes 1-6 to determine which latex/carbodiimide combination gave the best performance. The tensile test measurements for latexes 3, 5, and 6 were given in Table 9 and can be compared to those of 1, 2, and 4 in Table 2. Of the latexes examined in this study, 2, 4, and 5 showed the most favorable response toward crosslinking with the oligocarbodiimides. The stress-strain curves of the EH01 and EH03 blends of latexes 2, 4, and 5 are shown in FIG. 6. By observing the modulus of the curves, it can be concluded that latex 4 was the toughest film in this study. Latex 2 also had a high modulus, however, this was attenuated by its brittle behavior which was attributed to its highly crosslinked core. Latex 5 showed the least amount of strength of these three due to the fact that AA localizes predominantly on the surface of the latex particle and upon subsequent crosslinking with EH01 and EH03 formed nonuniform welds along the particle exterior.

TABLE 9

| Sample | Tensile Strength Pa (x 10⁶) (psi) | % Strain @ break |
|---|---|---|
| Latex 3 | 2.127 ± 0.1534 (308.492 ± 22.256) | 788.831 ± 69.947 |
| 135% EHO1 | 1.862 ± 0.185 (270.059 ± 26.829) | 744.012 ± 66.583 |
| 131% EHO3 | 1.643 ± 0.1644 (238.325 ± 23.850) | 447.992 ± 35.348 |
| Latex 5 | 1.632 ± 0.1702 (236.748 ± 24.686) | 862.511 ± 205.806 |
| 135% EHO1 | 2.018 ± 0.52 (292.634 ± 75.420) | 356.327 ± 38.752 |
| 131% EHO3 | 4.624 ± 0.3763 (670.690 ± 54.582) | 394.984 ± 32.447 |
| Latex 6 | 5.552 ± 0.0755 (805.266 ± 10.953) | 518.696 ± 9.193 |
| 135% EHO1 | 3.295 ± 0.2992 (477.875 ± 43.4) | 528.071 ± 25.311 |
| 131% EHO3 | 6.589 ± 0.3325 (955.683 ± 48.226) | 474.459 ± 22.272 |

In summary, we have found the ability of the EH01 and EH03 to effectively crosslink both depends on the nature of the carbodiimide itself as well as the composition and process conditions used to synthesize the carboxylated latex. Through the modification of reaction conditions during the emulsion polymerization, the amount of accessible carboxylate groups can be controlled and tailored to the desired specifications. Of the latexes prepared in this study the EH03 blends of 4 yielded the toughest films followed by latexes 2 and 5. This study demonstrated that the combination of proper latex design and choice of crosslinker were useful to improve the physical properties of latex films, which can be further enhanced through crosslinking at elevated temperature or prolonged cure time. Finally, the kinetic study of the thermal curing of these latex blends helped to prove that the reactive affinity of EH01 and EH03 differ mainly as a result of their differing solubility.

Freeze-thaw stability was tested for latexes 1, 2, and 4. Samples were tested without carbodiimide and blends with 109 mol % H01. The freeze-thaw stability was tested using ASTM D2243 by adding 25 ml of sample into a vial. The vial was placed in a freezer at −20° C. for 16 hours. The sample was removed and thawed for 7 hours at room temperature. The sample was observed for visual evidence of coagulation, seeding, or extreme increase in viscosity. All control latexes without carbodiimide failed after the first freeze-thaw cycle. The samples with 109 mol % H01 passed 4 freeze-thaw cycles.

Freeze-thaw stability of low VOC semi-gloss paints made from blends of latex dispersions and carbodiimides were also studied. Table 10 below outlines the paint formulations prepared and indicates which latex or latex-carbodiimide blend was used to make the paint as well as the results of the freeze-thaw resistance testing in each case. Amounts listed are in grams. Relative to control paints made with unmodified latex controls, the carbodiimide-latex blend paints showed enhanced freeze-thaw stability passing 4 freeze-thaw cycles with 135 mol % carbodiimide. At a level of only 33 mol % carbodiimide, moderate freeze-thaw stability was observed. The control paints without carbodiimide failed on the first cycle. The amounts in Table 10 are grams.

TABLE 10

| Paint Number | 1 | 2 | 3 | 4 | 5 | 6 | 7 | 8 | 9 |
|---|---|---|---|---|---|---|---|---|---|
| Latex sample/mole % & type CDI | Latex 1/0 | Latex 1/ 34 EH01 | Latex 1/ 135 EH01 | Latex 1/ 33 EH03 | Latex 1/ 100 EH03 | Latex 2/0 | Latex 2/ 34 EH01 | Latex 2/ 135 EH01 | Latex 2/ 33 EH03 |
|  | 43.6 | 43.5 | 43.2 | 43.5 | 43.2 | 40.9 | 40.8 | 40.8 | 40.8 |
| Water | 40 | 40 | 40 | 40 | 40 | 40 | 40 | 40 | 40 |
| NATROSOL ® 330 Plus thickener | 1 | 1 | 1 | 1 | 1 | 1 | 1 | 1 | 1 |
| PROXEL ® GXL biocide | 3 | 3 | 3 | 3 | 3 | 3 | 3 | 3 | 3 |
| AMP 95 ® wetting agent | 1 | 1 | 1 | 1 | 1 | 1 | 1 | 1 | 1 |
| FOAMASTER ® TCR defoamer | 2.9 | 2.9 | 2.9 | 2.9 | 2.9 | 2.9 | 2.9 | 2.9 | 2.9 |
| BYK ® 155 dispersant | 1 | 1 | 1 | 1 | 1 | 1 | 1 | 1 | 1 |
| POLYGLOSS ® 90 clay | 25 | 25 | 25 | 25 | 25 | 25 | 25 | 25 | 25 |
| Grind 20 minutes @ 3000 rpm then mix in @ 1000 RPM the following: | | | | | | | | | |
| Water | 60 | 60 | 60 | 60 | 60 | 60 | 60 | 60 | 60 |
| Ethylene Glycol | 15 | 15 | 15 | 15 | 15 | 15 | 15 | 15 | 15 |
| AQUAFLOW ® NHS-300 thickener | 15 | 15 | 15 | 15 | 15 | 15 | 15 | 15 | 15 |
| TiPure ® R746 TiO$_2$ | 293 | 293 | 293 | 293 | 293 | 293 | 293 | 293 | 293 |
| AQUAFLOW ® NLS-200-to KU of 105 | 3 | 3 | 3 | 3 | 3 | 3 | 3 | 3 | 3 |
| POLYPHASE ® CST fungicide | 6 | 6 | 6 | 6 | 6 | 6 | 6 | 6 | 6 |
| FOAMASTER ® TCR defoamer | 2.9 | 2.9 | 2.9 | 2.9 | 2.9 | 2.9 | 2.9 | 2.9 | 2.9 |
| BYK ® 155 dispersant | 7 | 7 | 7 | 7 | 7 | 7 | 7 | 7 | 7 |
| Mix 5 minutes at <1000 RPM | | | | | | | | | |
| TEXANOL ® solvent | 5 | 5 | 5 | 5 | 5 | 5 | 5 | 5 | 5 |
| Latex Dispersion | 500.2 | 501.5 | 504.6 | 501.5 | 504.6 | 533.4 | 533.8 | 534.7 | 533.8 |
| Water | 59.8 | 58.5 | 55.4 | 58.5 | 55.4 | 26.6 | 26.2 | 25.3 | 26.2 |
| AQUAFLOW ® NHS-300 thickener | 12.0 | 12.0 | 12.0 | 12.0 | 12.0 | 12.0 | 12.0 | 12.0 | 12.0 |
| Mix 5 minutes | | | | | | | | | |
| AQUAFLOW ® NLS-200 to adjust KU | | | | | | | | | |
| TOTAL | 1052.8 | 1052.8 | 1052.8 | 1052.8 | 1052.8 | 1052.8 | 1052.8 | 1052.8 | 1052.8 |

TABLE 10-continued

| Freeze Thaw Stability P/F | | | | | | | | | |
|---|---|---|---|---|---|---|---|---|---|
| 1st cycle | | F | P | P | F | P | F | P | P | P |
| 2nd cycle | | F | P | P | F | P | F | F | P | F |
| 3rd cycle | | F | F | P | F | P | F | F | P | F |
| 4th cycle | | F | F | P | F | P | F | F | P | F |

| | Paint Number | 10 | 11 | 12 | 13 | 14 | 15 |
|---|---|---|---|---|---|---|---|
| | Latex sample/mole % & type CDI | Latex 2/ 131 EH03 40.8 | Latex 4/0 43.7 | Latex 4/ 34 EH01 43.6 | Latex 4/ 135 EH01 43.3 | Latex 4/ 33 EH03 43.6 | Latex 4/ 131 EH03 43.3 |
| | Water | 40 | 40 | 40 | 40 | 40 | 40 |
| | NATROSOL ® 300 Plus thickener | 1 | 1 | 1 | 1 | 1 | 1 |
| | PROXEL ® GXL biocide | 3 | 3 | 3 | 3 | 3 | 3 |
| | AMP 95 ® wetting agent | 1 | 1 | 1 | 1 | 1 | 1 |
| | FOAMASTER ® TCR defoamer | 2.9 | 2.9 | 2.9 | 2.9 | 2.9 | 2.9 |
| | BYK ® 155 dispersant | 1 | 1 | 1 | 1 | 1 | 1 |
| | POLYGLOSS ® 90 clay | 25 | 25 | 25 | 25 | 25 | 25 |
| | Grind 20 minutes @ 3000 rpm then mix in @ 1000 RPM the following: | | | | | | |
| | Water | 60 | 60 | 60 | 60 | 60 | 60 |
| | Ethylene Glycol | 15 | 15 | 15 | 15 | 15 | 15 |
| | AQUAFLOW ® NHS-300 thickener | 15 | 15 | 15 | 15 | 15 | 15 |
| | TiPure ® R746 TiO$_2$ | 293 | 293 | 293 | 293 | 293 | 293 |
| | AQUAFLOW ® NLS-200-to KU of 105 | 3 | 3 | 3 | 3 | 3 | 3 |
| | POLYPHASE ® CST fungicide | 6 | 6 | 6 | 6 | 6 | 6 |
| | FOAMASTER ® TCR defoamer | 2.9 | 2.9 | 2.9 | 2.9 | 2.9 | 2.9 |
| | BYK ® 155 dispersant | 7 | 7 | 7 | 7 | 7 | 7 |
| | Mix 5 minutes at <1000 RPM | | | | | | |
| | TEXANOL ® solvent | 5 | 5 | 5 | 5 | 5 | 5 |
| | Latex Dispersion | 534.6 | 499.0 | 500.2 | 503.6 | 500.1 | 503.5 |
| | Water | 25.4 | 61.0 | 59.8 | 56.4 | 59.9 | 56.5 |
| | AQUAFLOW ® NHS-300 thickener | 12.0 | 12.0 | 12.0 | 12.0 | 12.0 | 12.0 |
| | Mix 5 minutes | | | | | | |
| | AQUAFLOW ® NLS-200 to adjust KU | | | | | | |
| | TOTAL | 1052.8 | 1052.8 | 1052.8 | 1052.8 | 1052.8 | 1052.8 |
| | Freeze Thaw Stability P/F | | | | | | |
| | 1st cycle | P | F | F | P | F | P |
| | 2nd cycle | P | F | F | P | F | P |
| | 3rd cycle | P | F | F | P | F | P |
| | 4th cycle | P | F | F | P | F | P |

Paint compositions were prepared from Latexes 4 and 7 with and without EH01 and EH03. The compositions are shown in Table 11 below. Properties of the paint compositions were tested. The tests conducted and the results of the tests are shown in Table 12 below.

TABLE 11

| Mass in grams | Latex 4 | Latex 4 w/ 100 mol % EH01 | Latex 4 w/ 100 mol % EH03 | Latex 7 | Latex 7 w/ 100 mol % EH01 | Latex 7 w/ 100 mol % EH03 |
|---|---|---|---|---|---|---|
| Water | 40 | 40 | 40 | 40 | 40 | 40 |
| NATROSOL ® 330 plus thickener | 1 | 1 | 1 | 1 | 1 | 1 |
| PROXEL ® GXL biocide | 3 | 3 | 3 | 3 | 3 | 3 |
| AMP ® 95 wetting agent | 1 | 1 | 1 | 1 | 1 | 1 |
| FOAMASTER ® TCR defoamer | 2.9 | 2.9 | 2.9 | 2.9 | 2.9 | 2.9 |
| TAMOL ® 731 dispersant | 1 | 1 | 1 | 1 | 1 | 1 |
| POLYGLOSS ® 90 clay | 25 | 25 | 25 | 25 | 25 | 25 |
| Grind 20 minutes @2000 rpm then mix in @ 1000 rpm the following: | | | | | | |
| Water | 60 | 60 | 60 | 60 | 60 | 60 |
| Ethylene Glycol | 15 | 15 | 15 | 15 | 15 | 15 |
| AQUAFLOW ® NHS-300 thickener | 15 | 15 | 15 | 15 | 15 | 15 |
| TIPURE ® R746 TiO$_2$ | 293 | 293 | 293 | 293 | 293 | 293 |
| AQUAFLOW ® NLS-200 thickener | 3 | 3 | 3 | 3 | 3 | 3 |
| FOAMASTER ® TCR thickener | 2.9 | 2.9 | 2.9 | 2.9 | 2.9 | 2.9 |
| TAMOL ® 731 dispersant | 7 | 7 | 7 | 7 | 7 | 7 |

TABLE 11-continued

| Mass in grams | Latex 4 | Latex 4 w/ 100 mol % EH01 | Latex 4 w/ 100 mol % EH03 | Latex 7 | Latex 7 w/ 100 mol % EH01 | Latex 7 w/ 100 mol % EH03 |
|---|---|---|---|---|---|---|
| Mix 5 minutes at < 1000 rpm | | | | | | |
| Dispersion | 499 | 503.6 | 503.5 | 492.4 | 497.5 | 497.1 |
| Water | 72 | 67.4 | 67.5 | 78.6 | 73.5 | 73.9 |
| AQUAFLOW ® NHS-300 thickener | 12 | 12 | 12 | 12 | 12 | 12 |
| Mix 5 minutes | | | | | | |
| Total | 1052.8 | 1052.8 | 1052.8 | 1052.8 | 1052.8 | 1052.8 |

TABLE 12

| | | Latex 4 | Latex 4 w/ 100 mol % EH01 | Latex 4 w/ 100 mol % EH03 | Latex 7 | Latex 7 w/ 100 mol % EH01 | Latex 7 w/ 100 mol % EH03 |
|---|---|---|---|---|---|---|---|
| Initial Stormer Viscosity | KU | 85 | 92 | 90 | 86 | 97 | 112 |
| Stormer Viscosity 24 h | KU | 86 | 88 | 90 | 91 | 100 | 117 |
| ICI Viscosity | poise | 1.14 | 1.46 | 1.25 | 1.00 | 1.49 | 1.98 |
| Heat Stability | KU | 101 | 103 | 99 | 87 | 91 | 102 |
| Stormer Visc. 2 wk./50° C. | Delta KU | 15 | 15 | 9 | −4 | −9 | −15 |
| Freeze Thaw Stability | P/F | | | | | | |
| | 1$^{st}$ cycle | F | P | P | P | P | P |
| | 5$^{th}$ cycle | F | P | P | P | P | P |
| Gloss on paper after 24 h dry | 20° C. | 10.6 | 17.8 | 8.7 | 7.7 | 17.6 | 16.1 |
| Gloss on paper after 24 h dry | 60° C. | 51.3 | 60.3 | 46.3 | 43.4 | 56.4 | 54.5 |
| Scrub Resistance (7 day dry) | 1 | 432 | 320 | 430 | 404 | 705 | 726 |
| | 2 | 428 | 305 | 434 | 425 | 714 | 756. |
| | average | 430 | 312.5 | 432 | 414.5 | 709.5 | 741 |
| Mechanical Properties after 14 day cure of 20 mil films | | | | | | | |
| Stress @ max load × 10$^6$ Pa | | 2.5 | 2.96 | 3.4 | 4.2 | 4.77 | 5.41 |
| (psi) | | (362.8) | (428.6) | (494.9) | (611.4) | (692.4) | (784.5) |
| % Elongation @ break | | 518.8 | 439.1 | 341.5 | 366.1 | 593.8 | 521.6 |
| Chemical Resistance after 7 day cure | 5 = poor | | | | | | |
| 5% NaOH | | 2 | 3 | 3 | 2 | 1 | 2 |
| 5% Sulfuric Acid | | 2 | 3 | 3 | 1 | 1 | 1 |
| Acetone | | 2 | 3 | 2 | 5 | 2 | 2 |
| MEK | | 4 | 5 | 5 | 5 | 5 | 5 |

In Table 11, the pigment/volume (PVC) content was 2.35%, and the volatile organic content (VOC) was ≦50 g/l. Table 12 shows that Latex 7 that was crosslinked with EH01 or EH03 gave improved results for several application properties. Scrub resistance, tensile strength, elongation, and chemical resistance were improved without a loss in gloss. Latex 7 that was crosslinked with EH03 gave better results than Latex 7 crosslinked with EH01. By using a fugitive base, all of the acid groups were accessible. Because crosslinking is not competitive with film formation at room temperature, significant particle-particle interdiffusion occurred. The carboxyl rich interfaces crosslinked after sufficient interdiffusion occurred.

A kinetic study of the UV-induced crosslinking chemistry of the oligocarbodiimides was conducted using a UV tunnel set at various intensities and speeds and an IR spectrometer that was used to follow the extent of reaction under different conditions. UV-initiated crosslinking proceeded rapidly and thoroughly in the absence of photoinitiator.

135 and 131 mol % blends of either EH01 or EH03 respectively with latexes 1, 2, or 4 were prepared. Films of these blends were cast onto ZnSe crystals, which provided an ideal substrate for UV crosslinking experiments because they are transparent to wavelengths in both the UV spectral region as well as the infra-red spectral region. Once cast, films were allowed to dry for 10 minutes.

An IR spectrum was made of each nascent film. Each film was then subjected to UV irradiation using a UV tunnel kept at ambient temperature. After each pass through the tunnel under specified intensity and speed, an IR spectrum was taken to monitor the extent of reaction. The loss in intensity of the band associated with the carbodiimide (2160-2180 cm$^{-1}$) was followed by taking the area under the band and normalizing it to the area underneath the band attributed to —C—H (3050-2800 cm$^{-1}$), which was assumed to remain constant.

Figure 7A:
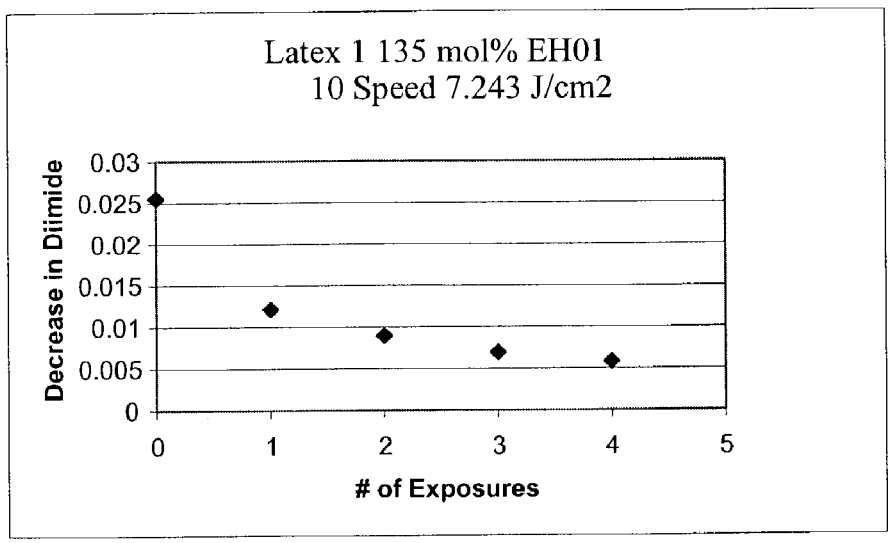
FIGS. 7a to 7r are graphs of UV induced reactivity of EH01 and EH03 blends with latexes 1, 2, and 4.
Figure 7B:
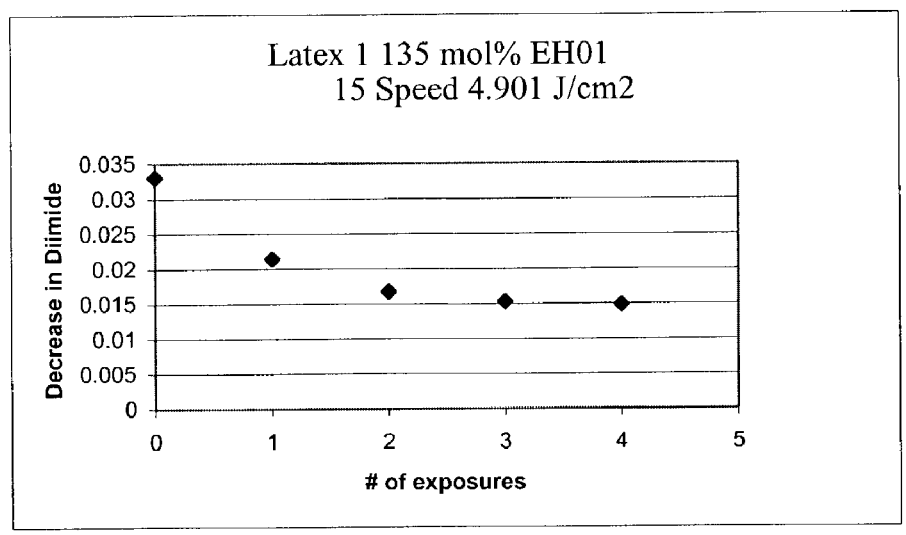
Figure 7C:
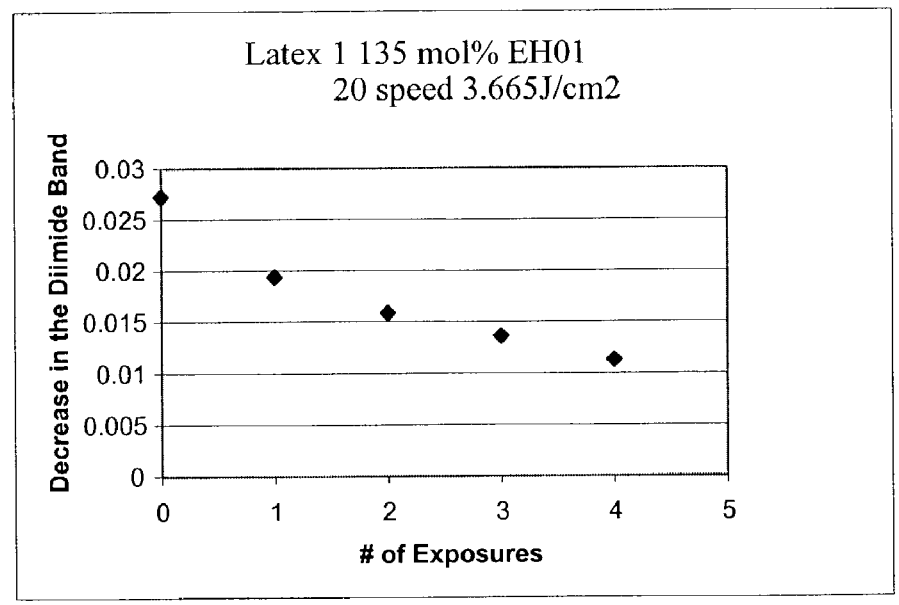
Figure 7D:
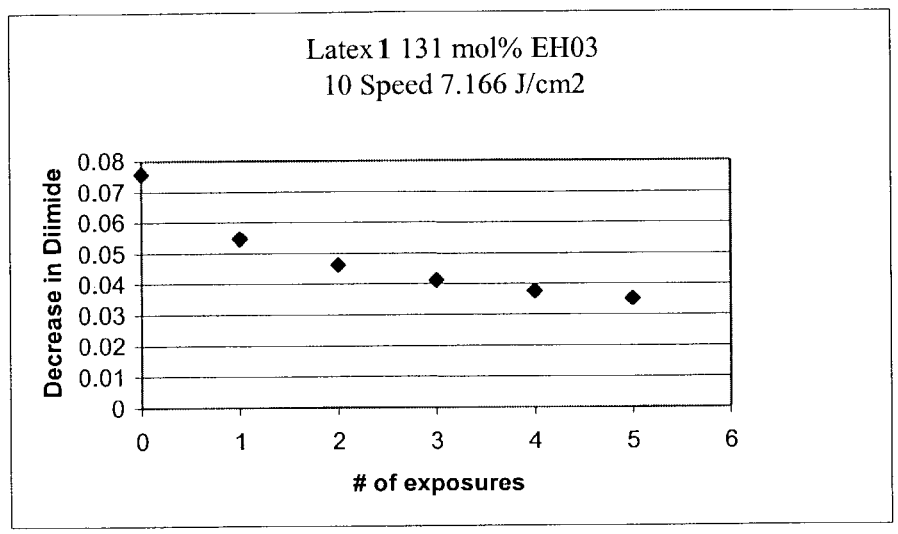
Figure 7E:
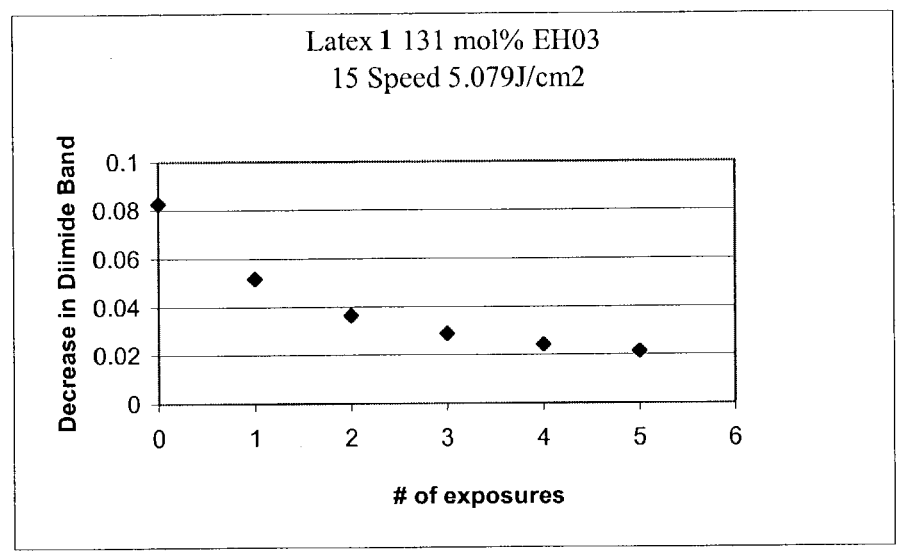
Figure 7F:
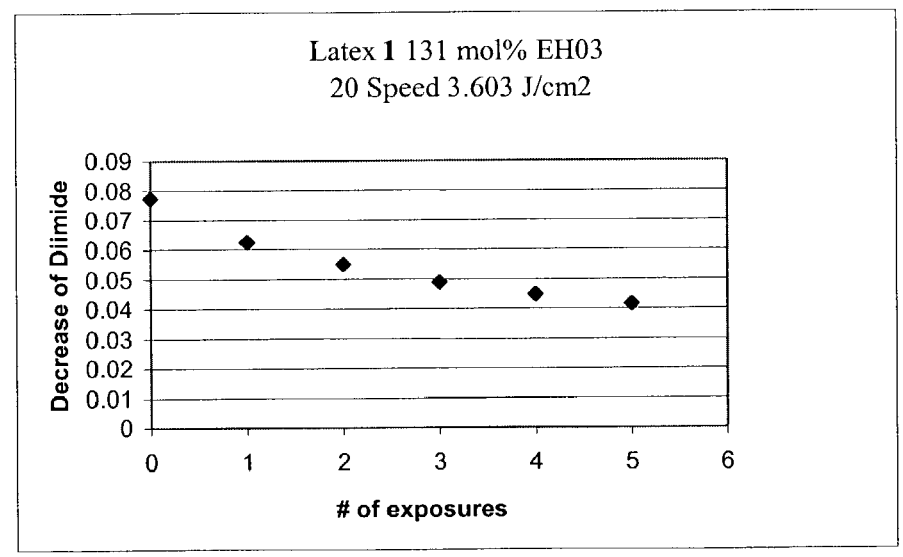
Figure 7G:
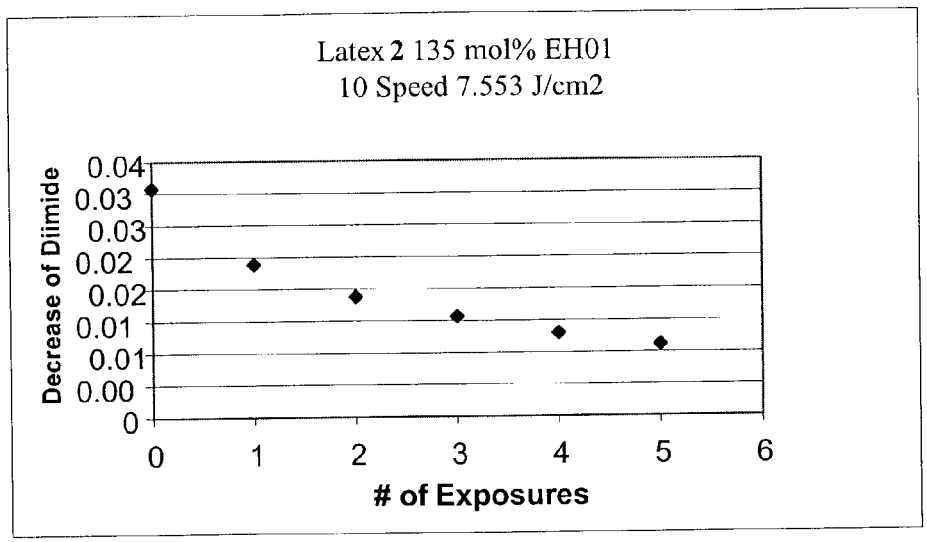
Figure 7H:
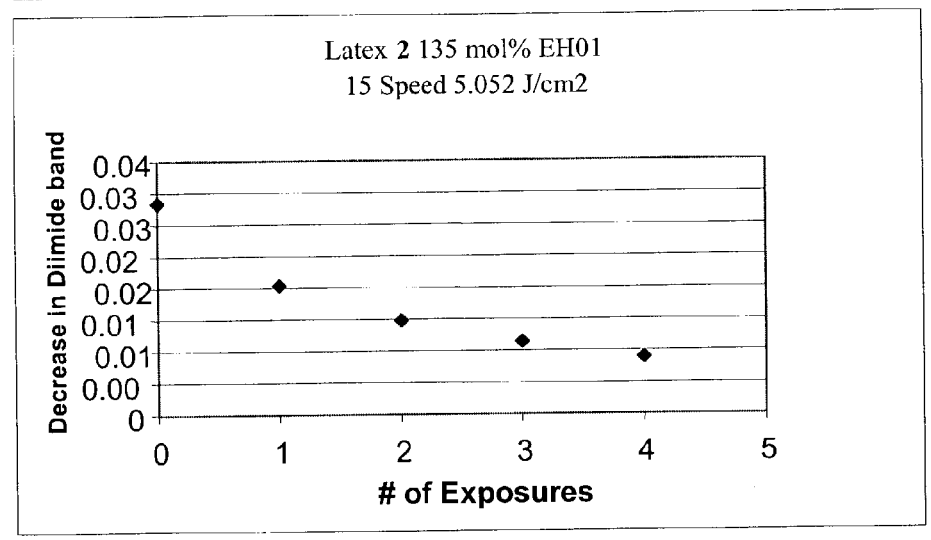
Figure 7I:
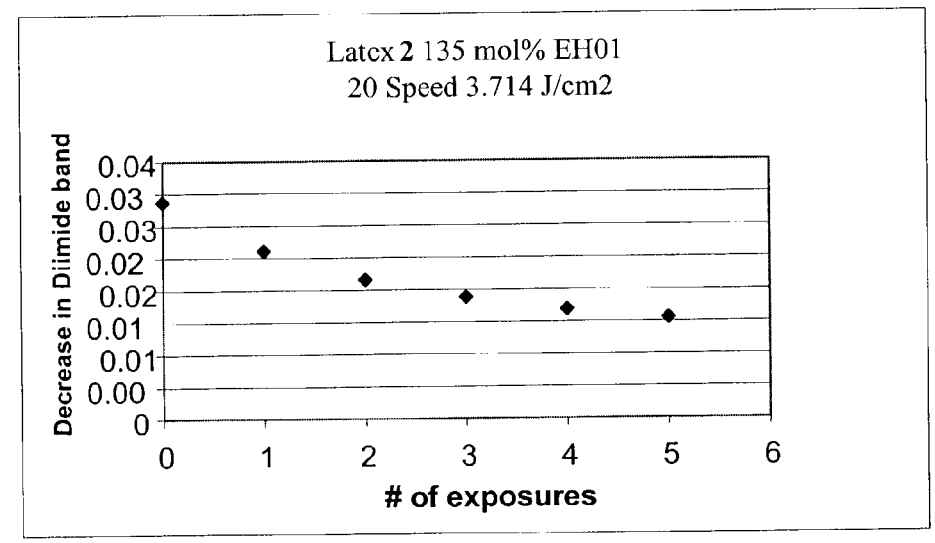
Figure 7J:
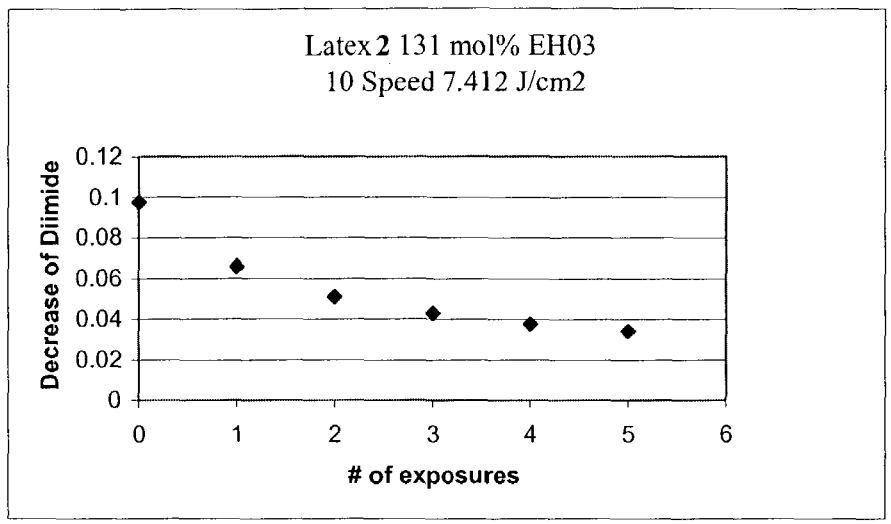
Figure 7K:
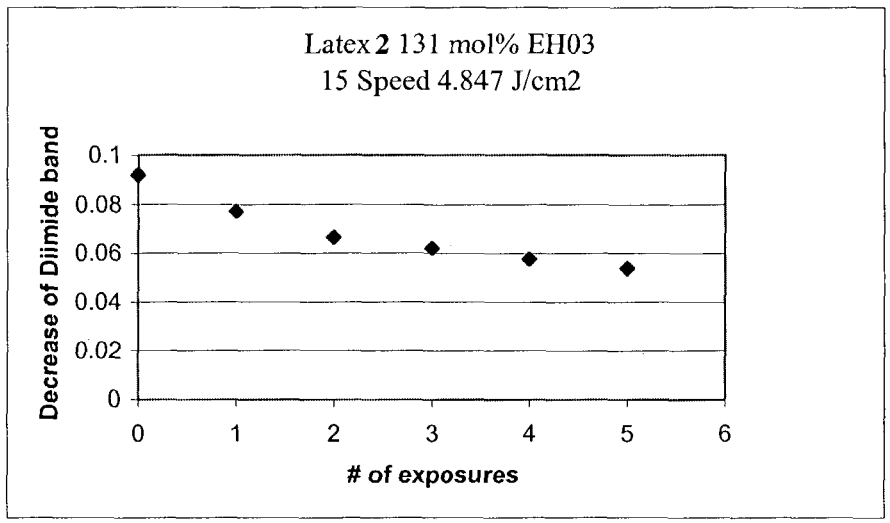
Figure 7L:
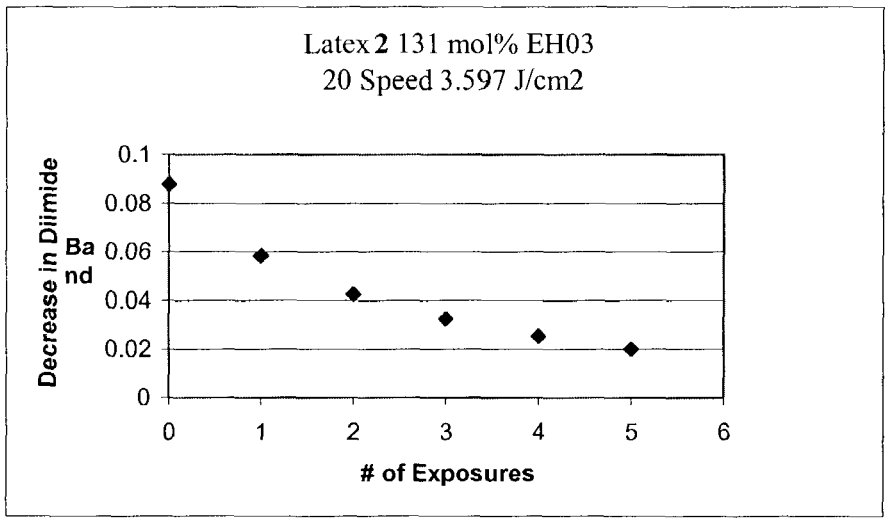
Figure 7M:
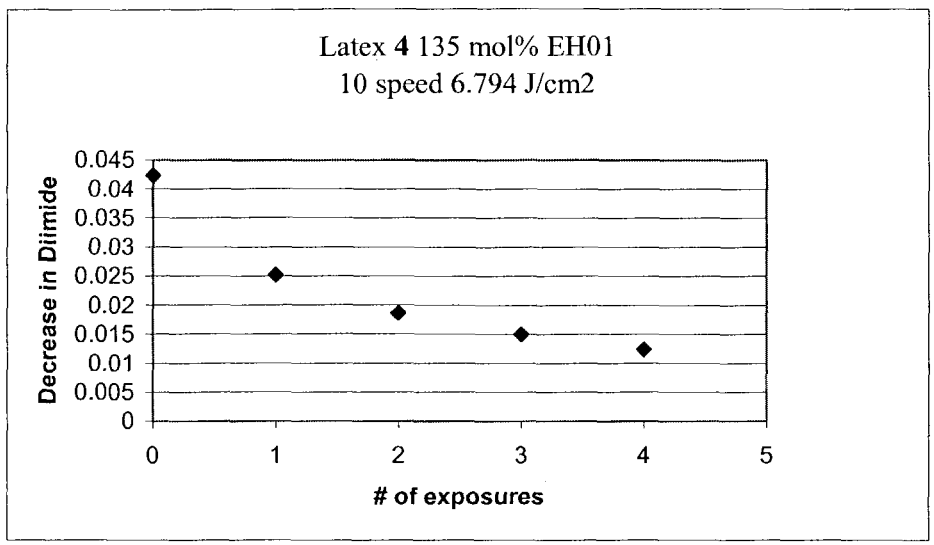
Figure 7N:
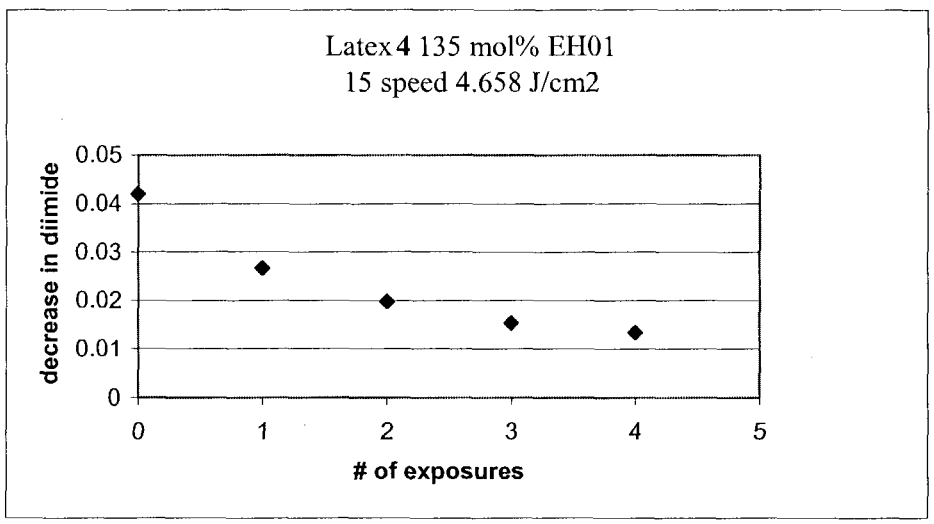
Figure 7O:
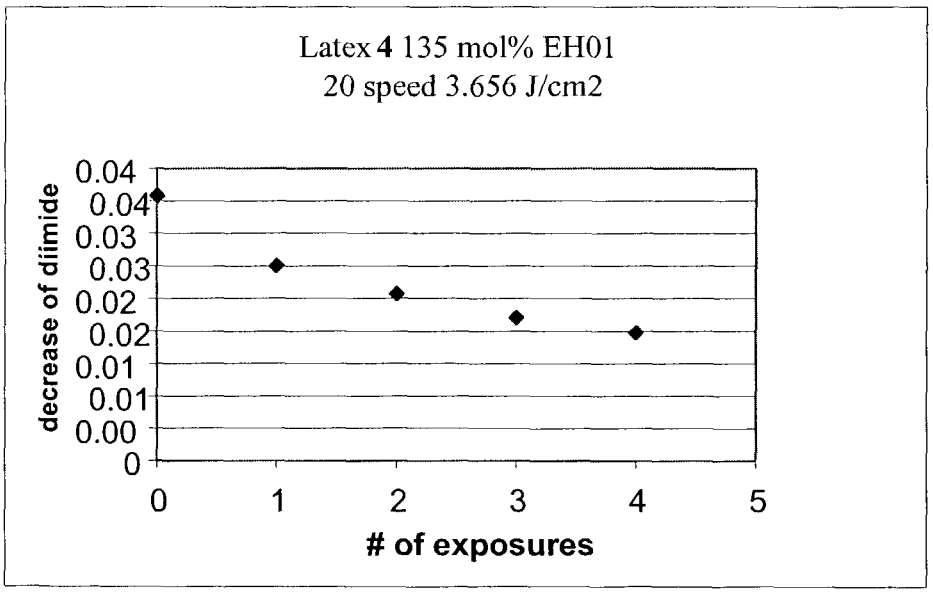
Figure 7P:
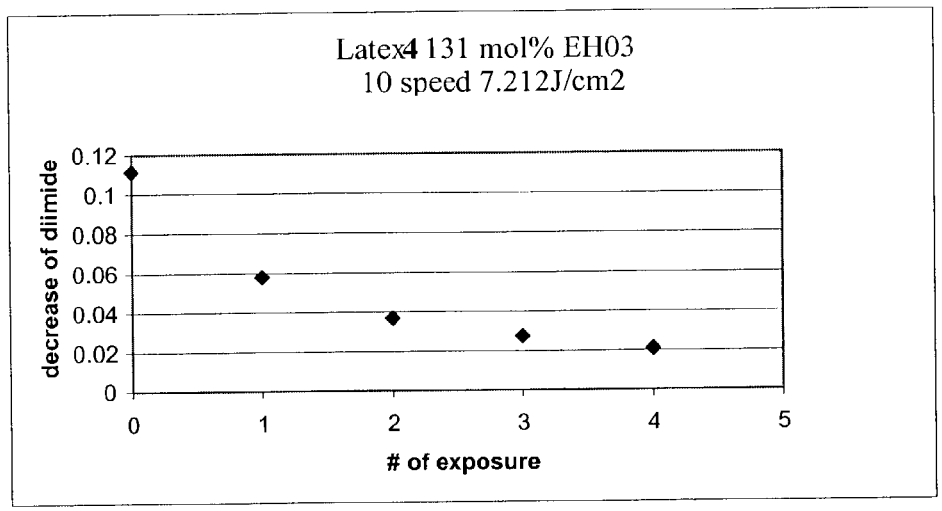
Figure 7Q:
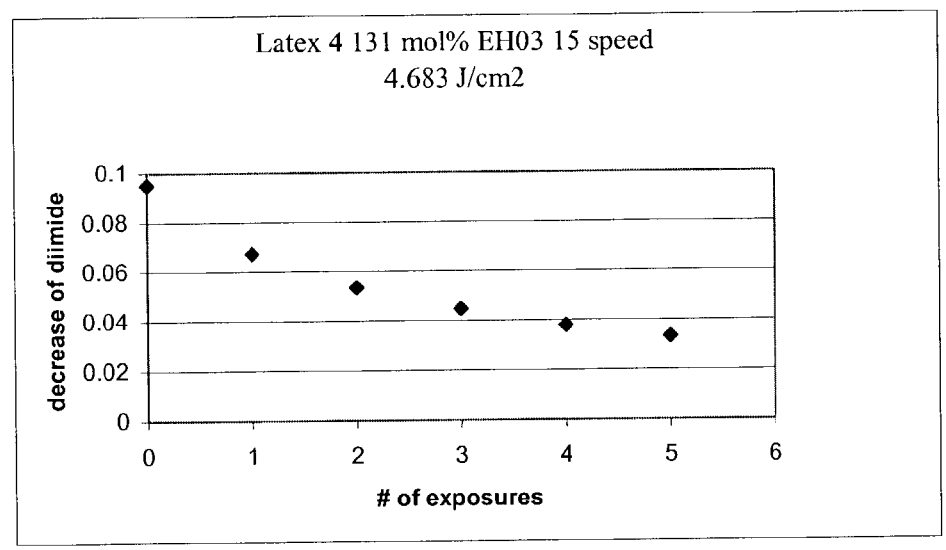
Figure 7R:
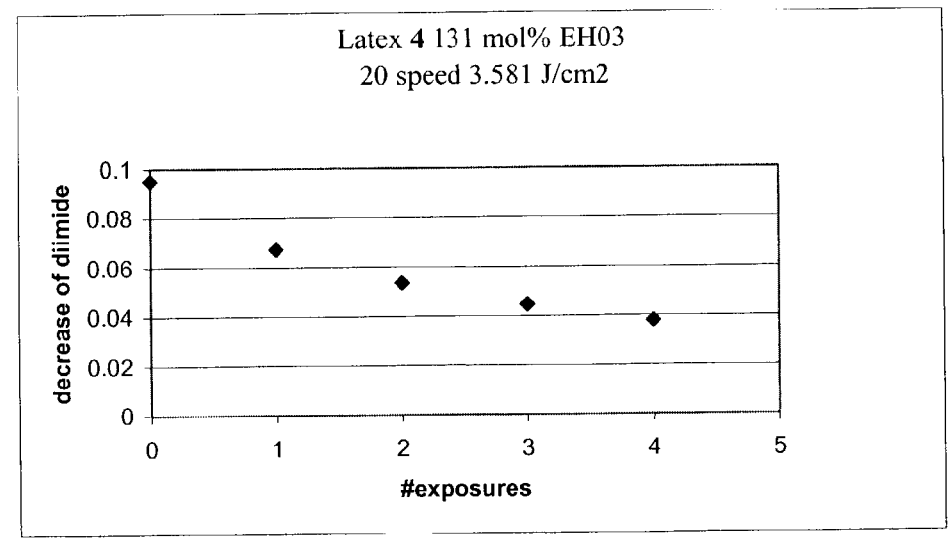

The conditions and the results of these experiments can be observed in the FIGS. 7a to 7r. For each latex/carbodiimide blend under any given set of UV-curing conditions, a loss in intensity of the carbodiimide band was observed indicating rapid reaction under the conditions used. Thus, the carbodiimide chemistry is not only suitable for crosslinking under ambient or higher temperatures, but is also very amenable to UV-crosslinking at room temperature or above.

Example SET 2

A series of water-soluble or water-dispersible oligo-carbodiimides were obtained. All of these compounds are hydrophilized derivatives of ELASTOSTAB® H02, a NCO-terminated tetramethyl xylene diisocyanate oligocarbodiimide obtained from Elastogran Lemförde GmbH. We compared the cross-linking of three different carbodiimide (CDI) derivatives with model latexes bearing different common vinylic acids such as acrylic acid (AA), methacrylic acid (MAA), and itaconic acid (IA). The obtained polymer films were characterized in terms of mechanical properties, T2 analysis and gel-content.

Three CDI-derivatives were tested, which were the nonionically stabilized compound ELASTOSTAB® H03 carbodiimide, an ionic urethane obtained from H02 and hydroxypivalic acid/triethylamine (HPS), and finally an ionic urethane obtained from H02 and hydroxyacetic acid/triethylamine (GLS).

The NCN-derivatives were dispersed in water and added to the latex dispersions. The specifications of the derivatives are given in Table 13.

TABLE 13

Specifications of the applied CDI-derivatives.

|     | SC [%] | NCN content kg/kg (solid) | NCN content mole/kg (solid) |
|-----|--------|---------------------------|-----------------------------|
| HPS | 23     | 10                        | 2.5                         |
| H03 | 10     | 10                        | 2.5                         |
| GLS | 9.7    | 11.2                      | 2.8                         |

In order to get a rough picture of the particle size of the aggregates in water, the particle size was determined by dynamic light scattering. The results are given in Table 14. It appeared that the HPS derivative tended to form more extended aggregates than H03 or the GLS derivative.

TABLE 14

Particle sizes of CDI dispersions in water.

|     | conc. [%] | D [nm] | Polydisp. |
|-----|-----------|--------|-----------|
| H03 | 0.5       | 25.3   | 0.217     |
|     | 1         | 23.8   | 0.293     |
| HPS | 0.01      | 181.5  | 0.317     |
|     | 0.1       | 182.4  | 0.334     |
| GLS | 1         | 18.5   | 0.434     |
|     | 2         | 17.5   | 0.435     |

Six model latex dispersions were prepared for a study. The base recipe is a BAIMMA=80/20 copolymer dispersion having a particle size of 250 nm, with 0.16 pphm of a proprietary seed from BASF AG, and being stabilized by 2 pphm DISPONIL® surfactant. Solid content was 55%. The recipes differed in the type and the amount of the vinylic acid that was copolymerized (see Table 15). The emulsion feed was partially neutralized by ammonia to a pH from about 3 to about 5, which is about 0.1 to 0.3 mole fraction based on total —COOH.

TABLE 15

Type and amount of acid in the dispersion recipe.

|     | Acid conc.        | COOH/100 g polymer | pphm |
|-----|-------------------|--------------------|------|
| 13A | AA; M = 72.06 g/mol   | 15 mM          | 1.08 |
| 13B | AA; M = 72.06 g/mol   | 30 mM          | 2.16 |
| 14A | MAA; M = 86.09 g/mol  | 15 mM          | 1.29 |
| 14B | MAA; M = 86.09 g/mol  | 30 mM          | 2.58 |
| 15A | IA; M = 130.10 g/mol  | 15 mM          | 0.98 |
| 15B | IA; M = 130.10 g/mol  | 30 mM          | 1.96 |

The polymers were analyzed to see how the acidic water-phase polymers affected the cross-linking with CDIs. The serum was separated from the dispersion by preparative ultracentrifuge and analyzed by aqueous-phase GPC. The results are presented in Table 16.

TABLE 16

Type and amount of acid in the dispersion recipe.

|     | acid | pphm | Soluble polymers In serum [% wt] | Mn | Mw | Mn/Mw |
|-----|------|------|----------------------------------|------|------|-------|
| 13A | AA   | 1.08 | 2.2                              | 1090 | 1470 | 1.3   |
| 13B | AA   | 2.16 | 4.1                              | 1890 | 3320 | 1.8   |
| 14A | MAA  | 1.29 | 2.5                              | 1030 | 1360 | 1.3   |
| 14B | MAA  | 2.58 | 3.7                              | 1590 | 2600 | 1.6   |
| 15A | IA   | 0.98 | 2.9                              | 790  | 920  | 1.2   |
| 15B | IA   | 1.96 | 4.6                              | 810  | 950  | 1.2   |

Surprisingly, the amount and the molecular weight of the water-phase polymers produced by acrylic acid and methacrylic acid did not differ significantly. The reason for this must be sought in the pre-neutralization of the emulsion feed making MAA more water-soluble. As expected, the amount of water-phase polymers induced by copolymerization with IA was higher than that of AA and MAA. The lower molecular weight of the water-phase IA copolymers is somewhat striking and stays unexplained.

The CDI derivatives were added to the dispersions in increasing molar ratios ranging from [COOH]:[NCN]=6:1, 2:1, 1:1 for the low amount of acid (15 mM [COOH]/100 g polymer) and [COOH]:[NCN]=12:1, 4:1, 2:1 for the high amount of acid (30 mM [COOH]/100 g polymer). Prior to the addition of the CDI, the dispersion was set to pH=7 by appropriate amounts of ammonia. The resulting film properties such as the gel content, T2-value, and storage modulus, G', at 100° C. are summarized in Table 17.

TABLE 17

| mixture | dispersion | CDI | [COOH]:[NCN] | Gel content [%] | T2 [ms] | DMA G' @100° C. [Pa] |
|---------|------------|-----|--------------|-----------------|---------|----------------------|
|         | 15 mM AA   |     |              |                 |         |                      |
| 13A     |            | /   |              | 65.6            | 5.57    | 26028                |
| 13-1    |            | H03 | 6:1          | 68.4            | 5.11    | 32562                |
| 13-2    |            | H03 | 2:1          | 74.1            | 3.82    |                      |
| 13-3    |            | H03 | 1:1          | 77.6            | 2.96    | 75583                |
| 13-4    |            | HPS | 6:1          | 56.5            | 5.19    | 27600                |
| 13-5    |            | HPS | 2:1          | 59.8            | 4.72    |                      |
| 13-6    |            | HPS | 1:1          | 58.3            | 3.87    | 31201                |

TABLE 17-continued

| mixture | dispersion | CDI | [COOH]:[NCN] | Gel content [%] | T2 [ms] | DMA G' @100° C. [Pa] |
|---|---|---|---|---|---|---|
| 20-1 | | GLS | 6:1 | 61.2 | 5.76 | 26838 |
| 20-2 | | GLS | 2:1 | 57.8 | 5.01 | 34660 |
| 20-3 | | GLS | 1:1 | 56.3 | 4.34 | 39604 |
| | 30 mM AA | | | | | |
| 13B | | / | | 68.0 | 5.33 | 35595 |
| 13-7 | | H03 | 12:1 | 72.7 | 5.03 | 41835 |
| 13-8 | | H03 | 4:1 | 82.6 | 3.54 | |
| 13-9 | | H03 | 2:1 | 81.6 | 2.40 | 92191 |
| 13-10 | | HPS | 12:1 | 67.1 | 4.91 | 32241 |
| 13-11 | | HPS | 4:1 | 68.6 | 4.53 | |
| 13-12 | | HPS | 2:1 | 67.8 | 3.39 | 37511 |
| 20-4 | | GLS | 12:1 | 69.9 | 5.21 | 46561 |
| 20-5 | | GLS | 4:1 | 68.0 | 4.65 | 47697 |
| 20-6 | | GLS | 2:1 | 64.4 | 4.02 | 53600 |
| | 15 mM MAA | | | | | |
| 14A | | / | | 61.0 | 5.57 | 30024 |
| 14-1 | | H03 | 6:1 | 55.5 | 5.54 | |
| 14-2 | | H03 | 2:1 | 59.1 | 5.09 | |
| 14-3 | | H03 | 1:1 | 61.9 | 5.81 | |
| 14-4 | | HPS | 6:1 | 53.7 | 5.23 | |
| 14-5 | | HPS | 2:1 | 57.1 | 4.98 | |
| 14-6 | | HPS | 1:1 | 56.1 | 4.80 | |
| | 30 mM MAA | | | | | |
| 14B | | / | | 66.8 | 4.67 | 45747 |
| 14-7 | | H03 | 12:1 | 68.9 | 4.71 | 46169 |
| 14-8 | | H03 | 4:1 | 74.2 | 4.65 | |
| 14-9 | | H03 | 2:1 | 67.2 | 4.54 | 40315 |
| 14-10 | | HPS | 12:1 | 63.4 | 4.58 | 43002 |
| 14-11 | | HPS | 4:1 | 63.5 | 4.46 | |
| 14-12 | | HPS | 2:1 | 61.7 | 4.33 | 42621 |
| | 15 mM IA | | | | | |
| 15A | | / | | 73.2 | 5.68 | 29523 |
| 15-1 | | H03 | 6:1 | 80.4 | 5.57 | |
| 15-2 | | H03 | 2:1 | 58.3 | 5.57 | |
| 15-3 | | H03 | 1:1 | 59.3 | 5.68 | |
| 15-4 | | HPS | 6:1 | 88.3 | 5.51 | |
| 15-5 | | HPS | 2:1 | 84.9 | 5.00 | |
| 15-6 | | HPS | 1:1 | 64.2 | 4.94 | |
| | 30 mM IA | | | | | |
| 15B | | / | | 81.6 | 5.35 | 37931 |
| 15-7 | | H03 | 12:1 | 64.2 | 5.45 | 34028 |
| 15-8 | | H03 | 4:1 | 58.0 | 5.22 | |
| 15-9 | | H03 | 2:1 | 57.0 | 5.14 | 35217 |
| 15-10 | | HPS | 12:1 | 72.8 | 5.30 | 34580 |
| 15-11 | | HPS | 4:1 | 74.4 | 4.93 | |
| 15-12 | | HPS | 2:1 | 63.2 | 4.56 | 33612 |

Figure 8A:
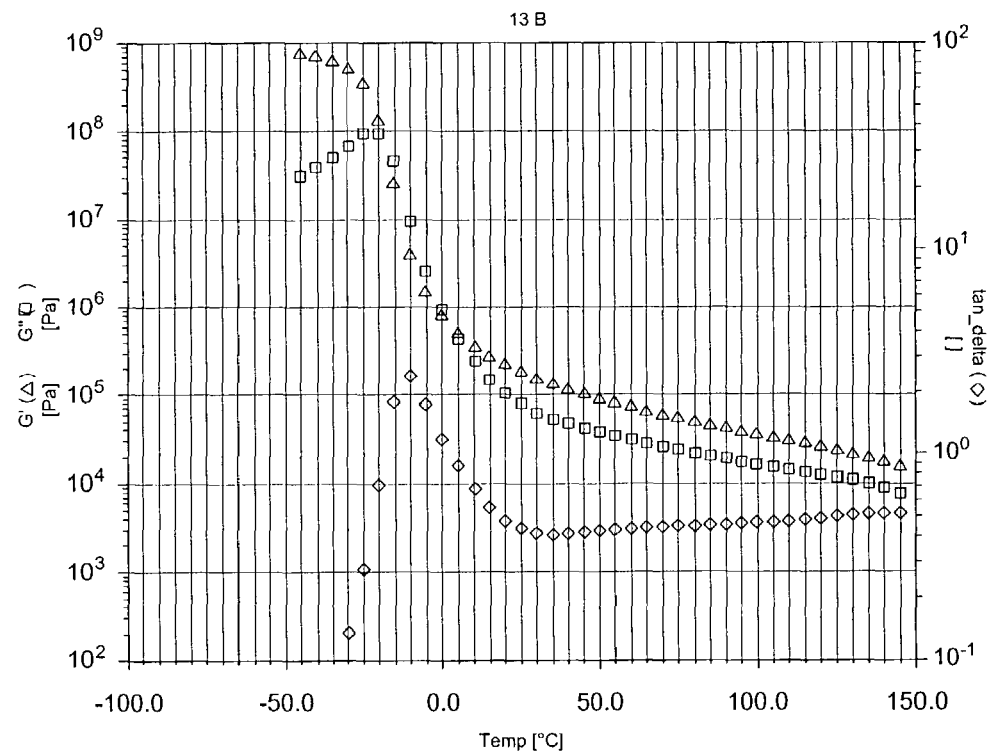
FIGS. 8a to 8d show DMA analysis for four samples from Example Set 2.
Figure 8B:
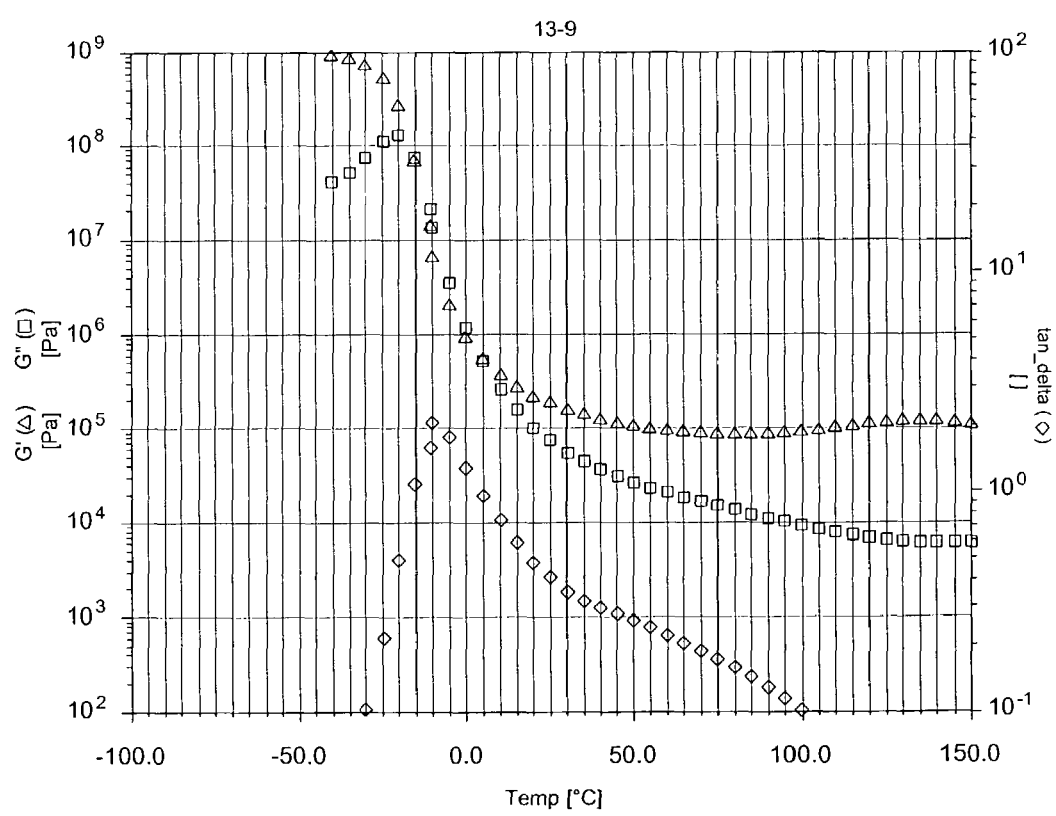
Figure 8C:
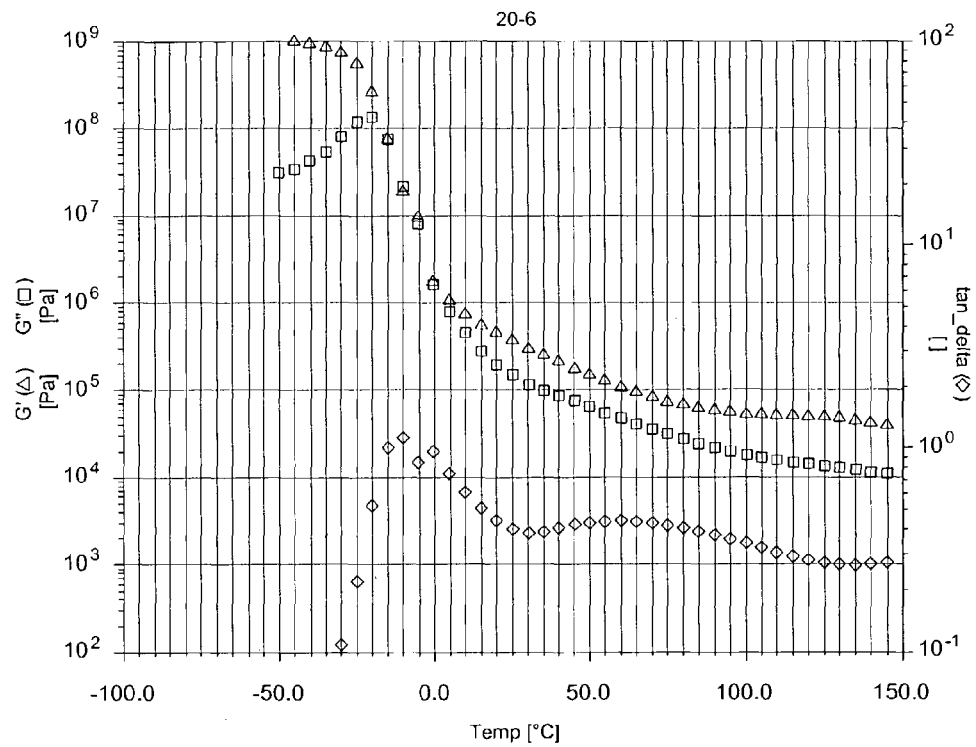
Figure 8D:
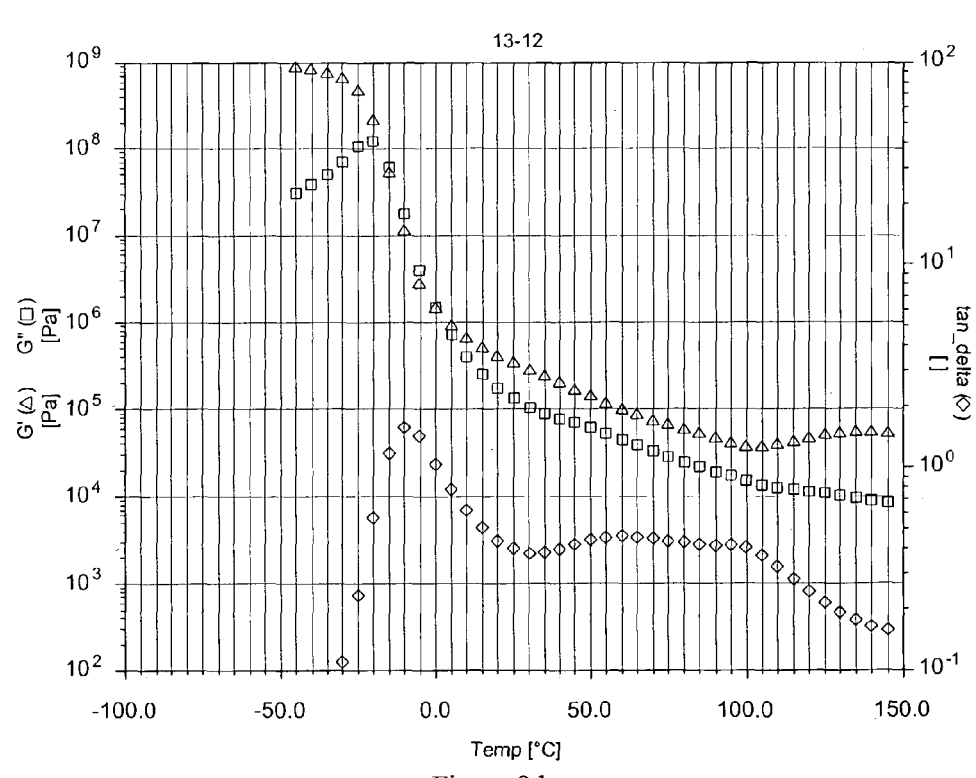

In a first set of experiments, the effect of the type of CDI was studied. FIGS. 8a to 8d show the DMA analysis for four representative samples based on the same dispersion. The original polymer film (2.16 pphm AA, FIG. 8a) is compared to those of mixtures with CDIs. In all the cases, the molar ratio [COOH]:[NCN] equaled 2:1. FIG. 8a exhibits the typical behavior of a non-cross-linked film where the storage modulus decreases with increasing temperature. The addition of the CDI, H03, induced a strong cross-linking of the bulk material characterized by an elevated storage modulus of about G'=100000 Pa at temperatures above 50° C. A similar effect was observed for the CDI derivative GLS. Finally, the derivative HPS led to a peculiar pattern which was characterized by a loss of G' below 100° C. and a slight increase above 100° C. It was theorized that this film was phase-separated in a sense that the crosslinker was trapped in the intersticial regions between the particles and should become more mobile upon heating resulting in an enhanced crosslinking of the bulk after tempering. In fact, annealing at 150° C. for 1 h turned out to be sufficient to homogenize the film. The slight of G' at higher temperatures then disappears.

Figure 9:
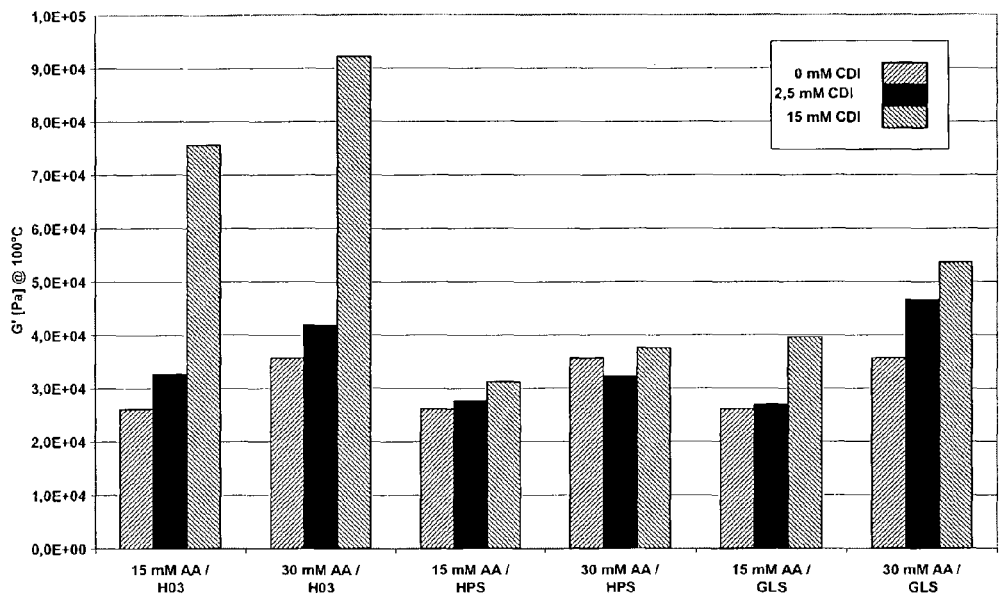
FIG. 9 is a graph of the storage modulus G' at 100° C. for different mixtures from Example Set 2 based on acrylic acid containing latex dispersions.
Figure 10:
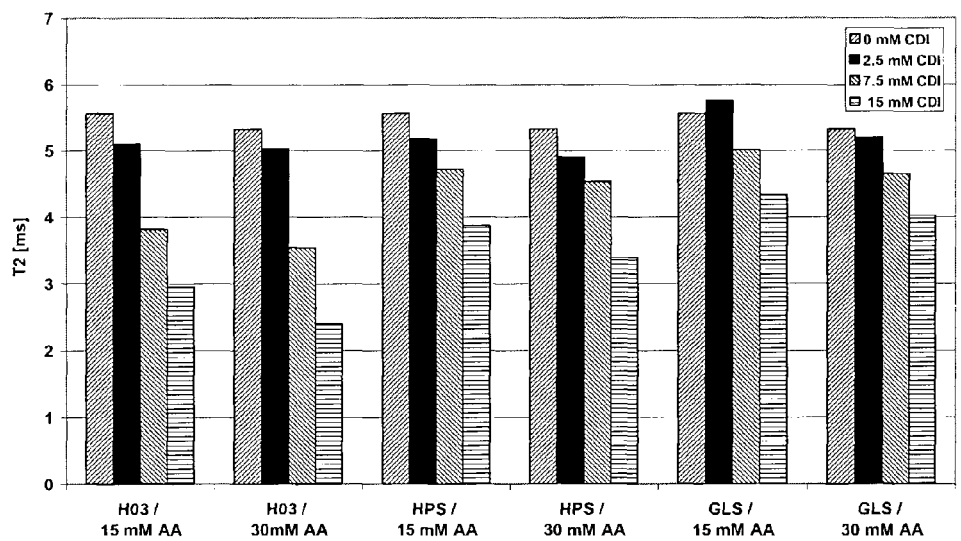
FIG. 10 is a graph of the T2 relaxation values for different mixtures from Example Set 2 based on acrylic acid containing latex dispersions.

From the DMA analysis, the efficiency of cross-linking of the CDI derivatives can be ranked in the following order: H03>GLS>HPS. In fact, this general trend was verified by further samples where the amount of acid and CDI were varied. FIG. 9 provides an overview on the results of the dynamical mechanical properties characterized by the storage modulus at 100° C. Supporting information comes from the measurement of the T2-relaxation times (FIG. 10), which are a measure of the molecular mobility of the polymer chains. The decrease in T2 values was most significant for the cross-linked polymer film containing H03; whereas, other CDI derivatives changed the T2 value only slightly. Finally, the determination of the gel-content corroborated the hypothesis that H03 is by far the most efficient cross-linker under the present circumstances (see Table 17). Note that for a constant level of CDI, the cross-linking density can be increased by an increased amount of acid (see FIG. 9 and Table 17).

From these results, it can be concluded that the —NCN— groups of the H03 derivative were more accessible for thorough cross-linking of the bulk polymer than those of the ionic derivatives HPS and GLS. One theory for this fact could be that the ionic derivatives tended to be phase-separated in the interstices between the particles; whereas, the non-ionic derivative could be more compatible. As discussed above, the DMA-analysis of the HPS-films seemed to suggest such a phase-separation.

Figure 11A:
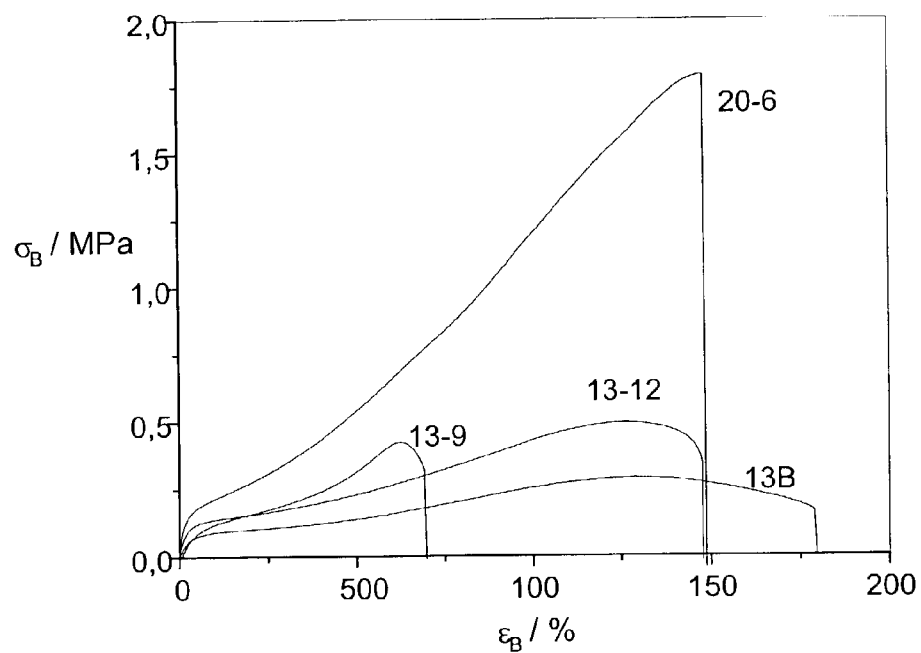
FIGS. 11a to 11c are graphs of stress-strain behavior for different samples from Example Set 2.
Figure 11B:
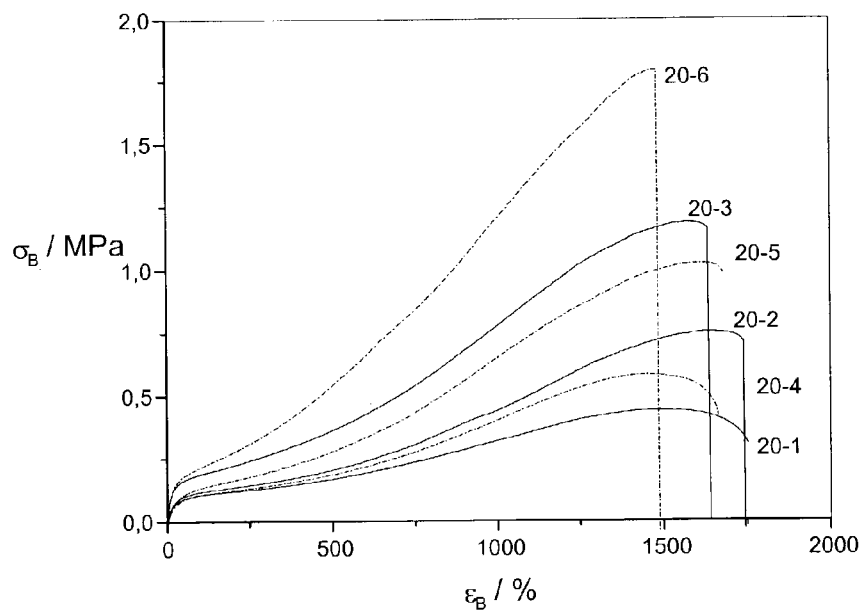
Figure 11C:
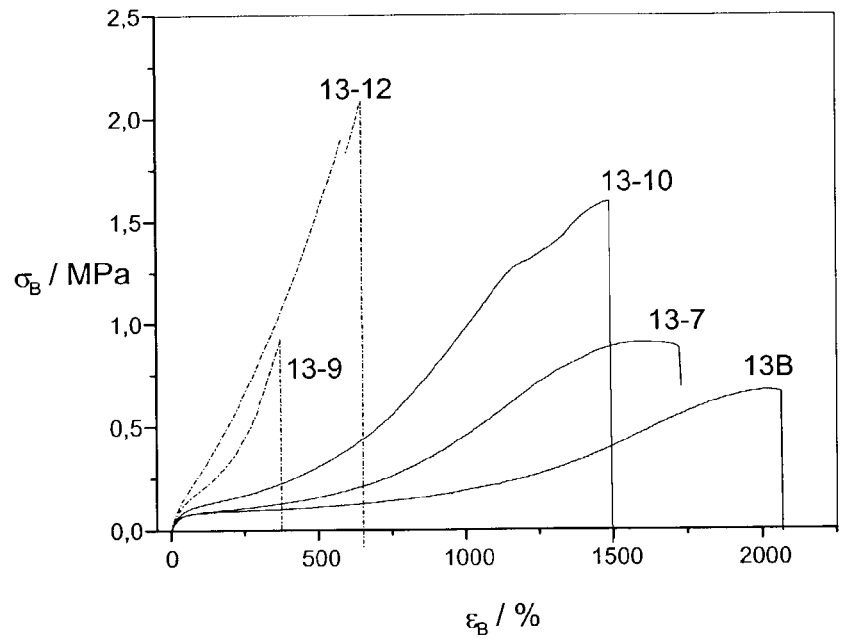

Complementary information on the mechanical strength of the films is provided by the stress-strain measurements characterizing the non-linear response and failure of the polymer films (FIG. 11a to 11c). The pattern of the bare dispersion corresponds to a typical polymer-film above the glass transition temperature. Cross-linking induced by H03 reduced the maximal elongation without increasing the maximal strain. This behavior can be interpreted in the light of the DMA measurements where a strong cross-linking of the bulk polymer was observed. Due to a substantial intra-particular and little inter-particular cross-linking, the polymer film become very brittle.

Figure 11D:
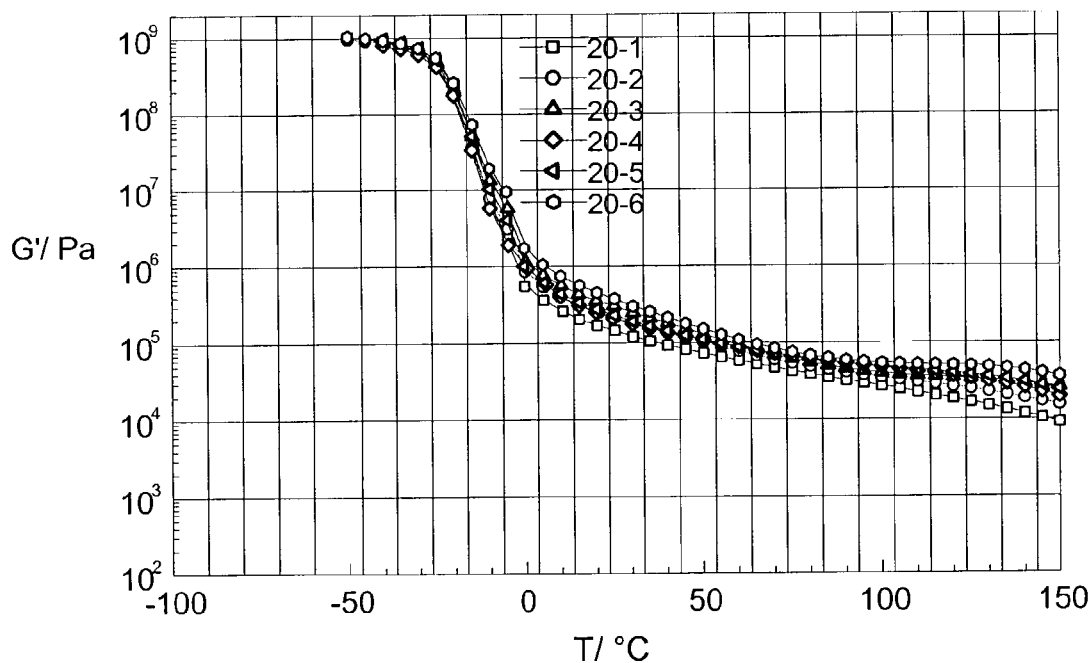

The HPS derivative hardly influenced the mechanical behavior. A slight reduction of the maximal elongation and a slight increase in the maximal strain suggests a small amount of inter-particular cross-linking. Quite surprising is the significant effect of the GLS derivative. Here, an enormous increase in the toughness can be achieved and the film exhibits a remarkable elasticity. This result in combination with the previously observed increased storage modulus (see above) implies a balanced combination of intra- and inter-particular cross-linking is present. As expected, the strength of the films (FIG. 11b) and the intra-particular cross-linking (FIG. 11d) can be tuned by the concentration of acid or CDI. While HPS seems to fail at room temperature, it can affect reasonable inter-particular crosslinking after annealing at 150° C. for one hour (see FIG. 11c). The maximal force at break can then become seven times as high compared to X-linking at room temperature. To a lesser extent, the same was true for the H03 derivative. Annealing at 150° C. enhanced the polymer inter-diffusion and triggered the cross-linking of HPS either chemically or simply by allowing more spatial proximity between —COOH and NCN— moieties. To a lesser extent, the same was true for the H03 derivative.

TABLE 18

Stress-strain behavior of polymer films.

| sample | CDI | $\sigma_B$ [MPa] | $\epsilon_B$ [%] | toughness [MPa] |
|---|---|---|---|---|
| 13B | / | 0.16 ± 0.01 | 1743 ± 170 | 3.5 ± 0.4 |
| 13-9 | 15 mM H03 | 0.3 ± 0.4 | 663 ± 33 | 1.4 ± 0.07 |
| 13-12 | 15 mM HPS | 0.3 ± 0.05 | 1620 ± 90 | 5.1 ± 0.3 |
| 20-6 | 15 mM GLS | 1.8 ± 0.03 | 1510 ± 70 | 13.1 ± 1.1 |

Figure 12:
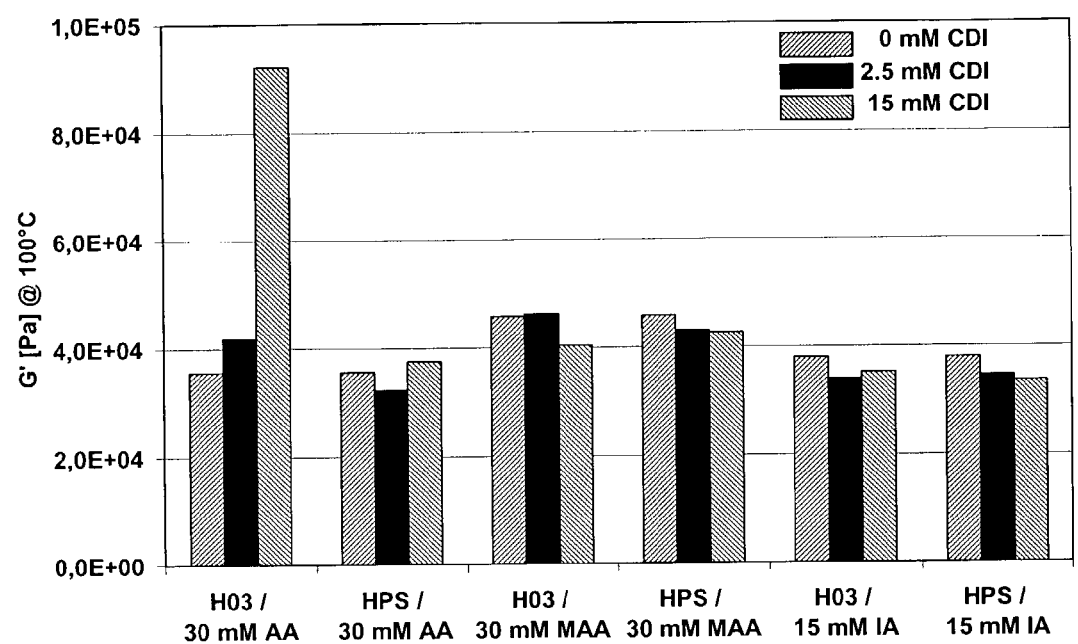
FIG. 12 is a graph of the storage modulus G' at 100° C. for different mixtures from Example Set 2 as a function of the vinylic acid.

In a next step, the effect of different vinylic acids was compared. FIG. 12 depicts the results of the dynamic mechanical analysis. Except for the combination H03/AA, none of the other combinations seems to afford any significant effect. Again, T2 values and the amount of gel formed (Table 17) further show that H03/AA provided the highest cross-linking density. The question arises why AA led to a higher degree of cross-linking than MAA; although, the distribution of the acid between water-phase polymers and particle phase should be comparable (see Table 16). One theory could be that the —COOH groups of MAA are more sterically hindered than those of AA, and, consequently, MAA was less reactive.

The situation for itaconic acid was expected to be different. IA will be mainly situated on the particle surface and in the water-phase. An increased amount of small water-phase polymers has also been confirmed by GPC (see Table 16). Note further that the experiment has been laid such that dispersions were compared having an equal concentration of COOH-groups, and, hence, the concentration of IA molecules was only half of the concentration of AA or MAA molecules because of its difunctionality. The spatial distribution of COOH-groups within the film was therefore less broad and offered less opportunities for cross-linking.

The whitening experiments have been carried out as follows: a latex film (60 μm) was cast on a glass plate, and the dry film was immersed in water. The time till occurrence of whitening within the film was measured.

It appeared that cross-linking by H03 accelerated the whitening of the film most probably due to the strong inter-particular network which impeded a proper film formation (see above). HPS did not show a pronounced effect, neither retardation nor acceleration of the whitening process. Finally, the GLS derivative retarded the whitening significantly. This is in line with the observed good film properties as evidenced by the stress-strain measurements.

The shelf-life of the mixtures were probed by the change in the turbidity (LD value) of the dispersion after defined intervals of storage at room temperature and at 50° C. in an oven. The mixtures with the highest amount of acid and CDI were considered. For none of these samples, a significant drop in the LD value could be detected (see Table 19). In order to check the efficiency of CDI after storage, the T2 measurements of a cast film were repeated.

TABLE 19

Shelf-life of the mixtures probed by the change in turbidity over time.

| | LD | LD | LD | T2 [ms] | T2 [ms] | FG |
|---|---|---|---|---|---|---|
| Time of storage Temp. 50° C. | 0 | 14 days | 42 days | 0 | 42 days | |
| 13B | 61 | 62 | 61 | 5.33 | 5.30 | 56.9 |
| 13-9 | 61 | 62 | 62 | 2.40 | 3.13 | 55.6 |
| 13-12 | 61 | 61 | 61 | 3.39 | 4.44 | 52.3 |
| Temp. RT | | | | | | |
| 13-9 | | | 61 | | | 55.6 |
| 13-12 | | 60 | | | | 52.3 |
| Temp. 50° C. | | | | | | |
| 14B | 61 | 61 | 61 | 4.67 | 4.86 | 55.6 |
| 14-9 | 61 | 62 | 62 | 4.54 | 4.81 | 54.4 |
| 14-12 | 61 | 62 | 63 | 4.33 | 4.43 | 51.3 |
| Temp. RT | | | | | | |
| 14-9 | | 62 | | | | 54.4 |
| 14-12 | | | 62 | | | 51.3 |
| Temp. 50° C. | | | | | | |
| 15B | 61 | 62 | 63 | 5.35 | 5.22 | 54.9 |
| 15-9 | 62 | 62 | 61 | 5.14 | 5.22 | 53.8 |
| 15-12 | 61 | 62 | 63 | 4.56 | 4.84 | 50.7 |
| Temp. RT | | | | | | |
| 15-9 | | 62 | | | | 53.8 |
| 15-12 | | 62 | | | | 50.7 |

We found that the non-ionic derivative H03 allowed for a thorough intra-particular cross-linking which yielded high storage moduli but brittle films. In contrast, the ionic derivative GLS afforded little intra-particular cross-linking but substantial inter-particular network-formation. This resulted in highly elastic films with an increased toughness. Comparing acrylic acid, methacrylic acid, and itaconic acid, it turned out that acrylic acid provided the highest degree of cross-linking. In general, we could demonstrate that the level and the topology of cross-linking can be influenced by varying type and amount of the CDI cross-linker. The shelf-life of the mixed dispersion appeared sufficient even after storage for 6 weeks at 50° C.

Preparing the Carboxyl-Carbodiimides:

With Dimethylolpropionic Acid

A solution of 500 g of a NCO-terminated carbodiimide from TMXDI, having an NCO content of 7.8% by weight, in 100 g of acetone was added to a solution of 67 g (0.5 mol) of DMPA and 60.0 g (0.593 mol) of triethylamine (TEA) in 100 g of acetone, with stirring. After 240 minutes of stirring at 60° C., the mixture was diluted with 2000 g of water and the acetone was stripped off under reduced pressure.

This gives a colloidal, aqueous solution of a carbodiimide, having a solids content of 22% and an LT of 100.

With Hydroxypivalic Acid

A solution of 250 g of a NCO-terminated carbodiimide from TMXDI, having an NCO content of 7.8% by weight, in 50 g of acetone was added to a solution of 59 g (0.5 mol) of hydroxypivalic acid and 60.0 g (0.593 mol) of triethylamine (TEA) in 100 g of acetone, with stirring. After 240 minutes of stirring at 60° C., the mixture was diluted with 1200 g of water and the acetone was stripped off under reduced pressure.

This gives a colloidal, aqueous solution of a carbodiimide, having a solids content of 23% and an LT of 100.

Use Examples

Use Example 2.1

Use in Leather Dressing

For testing as a leather dressing, a spray liquor having the following composition was prepared:
45.7 p ASTACIN® Top GA
45.5 p deionized water
0.5 p LEPTON® paste VL
p LEPTON® wax LD6609.
ASTACIN® Top GA is a polyester-polyurethane dispersion having a solids content of 30% by weight.
LEPTON® paste VL is a urethane-based associative thickener.
LEPTON® wax LD 6609 is a silicone-based hand agent.

This liquor was admixed in Use Example A1.1. with 7.8 p, in Use Example A1.2. with 15.5 p, of the solution from Example 1.1.

In the comparative example, C1, no solution was added.

The liquors were sprayed at a rate of 10 g/DIN A4 onto bottomed calf box leather and dried at A) 10 min/8S° C. and B) 12 h/80° C.

The leathers were conditioned for 2 days at 23° C. and 50% relative atmospheric humidity and then subjected to a physical leather test, with the following results:

| Finish batches: | | C1 | A1.1 | A1.2 |
|---|---|---|---|---|
| Veslic wet rub test | | 100× g–d | 300× g | 400× g |
| A) | | 250× s | 400× d–s | 500× d–s |
| B) | | 300× d–s | 900× d–s | 1300× d |
| Flexometer test 50,000 × dry | A) | gray/d* | 0* | 0 |
| Flexometer test 20,000 × wet | A) | gray/g–d* | 0 | 0 |
| Flexometer test 50,000 × dry | B) | g* | 0 | 0 |
| Flexometer test 20,000 × wet | B) | gray/g* | 0 | 0 |

Evaluation: 0 = no damage; g = slight damage;
d = distinct damage; s = severe damage;
* = sticking occurs at site of pressing Evaluation: 0=no damage; g=slight damage; d=distinct damage; s=severe damage; *=sticking occurs at site of pressing Use Example 2.2

Use to Produce Protective Sheets

Preparing a Polymer Dispersion:

| | Initial charge (g) | Monomer emulsion (g) | Initiator (g) | After catalysis |
|---|---|---|---|---|
| Water | 260 | 200 | | 35.10 |
| Emulsifier solution 1 | | 24 | | |
| Emulsifier solution 2 | | 8 | | |
| 2-EHA | | 214.5 | | |
| nBA | | 450.45 | | |
| MMA | | 21.45 | | |
| M-Amol | | 95.33 | | |
| AA | | 14.3 | | |
| NaPS 5% solution in water | | | 71.5 | |
| $NH_3$ 25% solution in water | | | | 13.5 |
| t-BHP 10% solution in water | | | | 21.45 |
| Acetone | | | | 1.36 |
| Na disulfite | | | | 2.15 |

Emulsifier solution 1: 30% strength by weight solution of the sodium salt of a sulfuric monoester mixture of C10-C16 alkyl ethoxylates (average EO degree 30) in water (DISPONIL® FES 77 from Henkel KgaA)

Emulsifier solution 2: 45% strength by weight solution of (dodecyl-sulfonyl-phenoxy)benzenesulfonic acid sodium salt (DOWFAX® 2A1 from Dow Chemicals)

Procedure:

The initial charge was placed in a 2 liter flask with reflux condenser, nitrogen inlet, and metal stirrer. It was brought to 90° C. under nitrogen blanketing. 20% of the initiator solution were added. After 5 minutes, the monomer emulsion was added over the course of 3 hours. At the same time, the remaining initiator solution was added over the course of 3.5 hours. After the end of the initiator feed, polymerization was continued for 30 minutes. The mixture was then cooled to 80° C. and the after-catalyst solution and ammonia were added.

The two t-BHP and acetone/Na disulfite feeds were added in parallel over the course of 1 hour. Subsequently, the dispersion was cooled to room temperature.

The solids content of the dispersion is 51%; the pH is 7. The particle size is 280 nm (as determined by means of a Malvern autosizer).

Application: Protective Sheet

Producing the Protective Sheets

The dispersion was mixed with 1.5% (solids/solids) (A2.1.) or with 3% (solids/solids) (A2.2.) of the solution from Example 1.1. For comparison, a mixture was prepared from the dispersion with 1.5% BASONAT® FDS 3425 (C2).

The mixtures were knife coated at from 5 to 6 g/m² onto a corona-treated polyethylene film and dried at 90° C. for three minutes. The films were lined with silicone paper and stored at room temperature for three days.

Testing for Removal without Residue:

This test consists in evaluating the appearance of the protected surface following the removal of the protective sheet. The surface to which the sheet is stuck is stored for one and four weeks at 50° C. and 80% relative atmospheric humidity. The sheets are then peeled off by hand, slowly in one instance and rapidly in another, and the residue on the surface is assessed visually. In the best case, the surface is free from residues of the adhesive.

Evaluation is made in accordance with the following scale:
no residue
1* negative impression of the protective sheet (shadows at the edge, no shadows otherwise) shadow of the protective sheet
residue perceptible
partial transfer of the adhesive
complete transfer of the adhesive
cohesive fracture.

The peel behavior is assessed in accordance with the following scale:
A slightly tacky
B easy to remove
C difficult to remove.

Tests were carried out on steel, polycarbonate, and plexiglass.

The optimum rating is B 1.

TABLE

Results of the removal test.

| Dispersion | Removal | Plexiglass | | Polycarbonate | | Steel | |
|---|---|---|---|---|---|---|---|
| | | 1 week | 4 weeks | 1 week | 4 weeks | 1 week | 4 weeks |
| Dispersion without crosslinker | slow | B1 | B1 | B1 | B1 | B1* | B2 |
| | rapid | B1 | B1 | B1 | B1 | B3 | B3 |
| Dispersion +1.5% BASONAT ® FDS3425 | slow | B1 | B1 | B1 | B1 | B2 | B2 |
| | rapid | B1 | B1 | B1 | B1 | B2 | B3 |
| Dispersion +1.5% solution 1.1 | slow | B1 | B1 | B1 | B1 | B2 | B1* |
| | rapid | B1 | B1 | B1 | B1 | B2 | B2 |
| Dispersion +3% solution 1.1 | slow | B1 | B1 | B1 | B1 | B1* | B1* |
| | rapid | B1 | B1 | B1 | B1 | B1* | B2 |

Quick Stick, Peel Strength, and Scratch Test on PE Film:

The dispersions were knife-coated at 20 g/m$^2$ onto 25 mm wide sections of PE film and dried at 90° C. for 3 minutes.

The protective sheets obtained in this way were bonded to a steel plate and the "quick stick" and peel strength were tested at 23° C. and 50% relative atmospheric humidity.

The quick stick test is one of the best-known methods of measuring tack (tack is the ability of a pressure-sensitive adhesive to adhere immediately to a surface). In the quick stick method (FINAT method) a test strip is looped, brought into contact with a glass plate, and peeled off again immediately thereafter.

The adhesion of the dispersion to the sheet is tested by means of the scratch test: the more difficult it is to scratch off the film with the finger, the better the adhesion of the dispersion.

Peel rate: 300 mm/min

| | Quick stick N/25 mm | Peel strength in N/25 mm steel | | scratch test |
|---|---|---|---|---|
| | steel | immediate | 24 hours | |
| Dispersion without crosslinker | 3.5 A | 1.8 A | 6.2 A | 3 |
| Dispersion +1.5% BASONAT ® FDS 3425 | 2.4 A | 1.1 A | 4.6 A | 1 |
| Dispersion +1.5% carbodiimide 1.1 | 3.1 A | 1.5 A | 6.5 A | 1-2 |
| Dispersion +3.0% carbodiimide 1.1 | 2.6 A | 1.2 A | 6.3 A | 1 |

Scratch test 1=no scratch removal
2=difficult to remove by scratching
3=easy to remove by scratching Determining the Crosslinking Density by Measuring the Dynamic Shear Modulus of Films:

On films with and without carbodiimide or Basonat®, the storage modulus G' and the loss modulus G" were measured as a function of temperature. The films were thermally conditioned at 90° C. for 10 minutes.

TABLE

Storage moduli at 100° C.

| Sample | G' at 100° C. (×10$^4$ Pa) |
|---|---|
| Dispersion without crosslinker | 4.98 |
| Dispersion + 1.5% BASONAT ® FDS 3425 | 6.46 |

TABLE-continued

Storage moduli at 100° C.

| Sample | G' at 100° C. (×10$^4$ Pa) |
|---|---|
| Dispersion + 1.5% carbodiimide 1.1 | 5.81 |
| Dispersion + 3.0% carbodiimide 1.1 | 7.17 |

The additions increase the storage modulus at high temperatures, which is a measure of the crosslinking density.

Abbreviations
nBA: n-butyl acrylate
MMA: methyl methacrylate
M-Amol: methylolmethacrylamide
AA: acrylic acid
NaPS: sodium peroxodisulfate t-BHP: tert-butyl hydroperoxide
NH₃: ammonia
2-EHA: 2-ethyl hexylacrylate
P.: parts.

The following test methods were used throughout this specification:

| | |
|---|---|
| Tensile Strength and Elongation: | ASTM D2370 |
| Water Absorption and Water Solubles | ASTM D870 |
| Freeze-Thaw Stability | ASTM D2243 |
| Gloss | ASTM D523 |
| Scrub resistance | ASTM D2486 |
| ICI Viscosity | ASTM D4287 |
| Gel Content and Swelling Index | ASTM D2765 using tetrahydrofuran as solvent |
| Chemical and Stain Resistance | DIN68861C |
| Storage Modulus | Dynamic Mechanical Analysis, which can be measured by using ASTM Standards D4065, D4092, D4473, D5023, D5024, D5026, D5418, E1142, E1640, E1867 |

Heat Stability was measured by measuring the viscosity with a STORMER viscometer initially and after 14 days at 50° C. Sample is allowed to equilibrate with ambient temperature overnight before viscosity is measured.

It should be appreciated that the present invention is not limited to the specific embodiments described above, but includes variations, modifications and equivalent embodiments defined by the following claims.

What is claimed is:

1. A curable composition curable thermally and by UV radiation comprising a carbodiimide and a film-forming water-dispersible polymer, wherein the carbodiimide comprises a reaction product of
   a) at least one of an aliphatic $C_4$ to $C_{20}$ polyisocyanate and an araliphatic $C_4$ to $C_{20}$ polyisocyanate,
   b) at least one of a mono-hydroxyl-functional carboxylic acid and a mono-hydroxyl-functional carboxylic salt,
   c) optionally, a further compound carrying groups able to react with isocyanate groups in an addition reaction,
   d) optionally, at least one other isocyanate, and
carbodiimide units in the carbodiimide being derived essentially exclusively from the isocyanate groups of component a), wherein the carbodiimide is represented by the structure

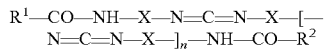

wherein X is at least one of an aliphatic hydrocarbon radical having 4 to 12 carbon atoms, a cycloaliphatic hydrocarbon radical having 6 to 15 carbon atoms, and an araliphatic hydrocarbon radical having 7 to 15 carbon atoms; n is an integer from 0 to 10; and $R^1$ and $R^2$ are radicals derived from component b) by abstraction therefrom of a hydrogen atom attached to a hydroxyl group, wherein the carbodiimide is free from units derived from macropolyols having a molecular weight of more than 400, and
   the water-dispersible film-forming polymer comprises a reaction product of an ethylenically unsaturated carboxylic acid and at least one of a $C_1$ to $C_{20}$ alkyl (meth)acrylate, a vinyl ester of a carboxylic acid containing up to 20 carbon atoms, a vinyl aromatic compound having up to 20 carbon atoms, an ethylenically unsaturated nitrile, a vinyl halide, an aliphatic hydrocarbon having 2 to 8 carbon atoms and 1 or 2 double bonds, and a free-radically polymerizable monomer and the polymer comprises carboxylic acid groups in amounts of from 0.01 to 2 mol/kg and
   wherein, under cure conditions, the carbodiimide undergoes a crosslinking reaction with the carboxylic acid to form acylurea groups.

2. The composition of claim 1, wherein at least a majority of the ethylenically unsaturated carboxylic acid is in a core of the water-dispersible film-forming polymer.

3. The composition of claim 1, wherein at least a majority of the ethylenically unsaturated carboxylic acid is in a shell of the water-dispersible film-forming polymer.

4. The composition of claim 1, wherein the ethylenically unsaturated carboxylic acid is distributed throughout the water-dispersible film-forming polymer.

5. The composition of claim 1, wherein the water-dispersible film-forming polymer is formed from an at least two stage multi-stage reaction, and all of the ethylenically unsaturated carboxylic acid is polymerized in the first stage.

6. The composition of claim 1, wherein the water-dispersible film-forming polymer is formed from an at least two stage multi-stage reaction, and all of the ethylenically unsaturated carboxylic acid is polymerized in the last stage.

7. The composition of claim 1, wherein the water-dispersible film-forming polymer is formed from a gradient feed reaction.

8. The composition of claim 1, wherein the ethylenically unsaturated carboxylic acid is a least one of (meth)acrylic acid, maleic acid, fumaric acid, itaconic acid, ethacrylic acid, crotonic acid, citraconic acid, cinnamic acid, phthalic acid, isophthalic acid, terephthalic acid, tetrahydrophthalic acid, hexahydrophthalic acid, tetrabromophthalic acid, trimellitic acid, pyromellitic acid, 1,4,5,6,7,7-hexachloro-5-norbornene-2,3-dicarboxylic acid, succinic acid, 2,6-naphthalenedicarboxylic acid, glutaric acid, sebacic acid, azelaic acid, 1,4-cyclohexanedicarboxylic acid, and 1,3-cyclohexanedicarboxylic acid.

9. The composition of claim 1, wherein the ethylenically unsaturated carboxylic acid is at least one of acrylic acid, methacrylic acid, crotonic acid, and itaconic acid.

10. The composition of claim 1, wherein the carbodiimide is represented by at least one of the following structures:

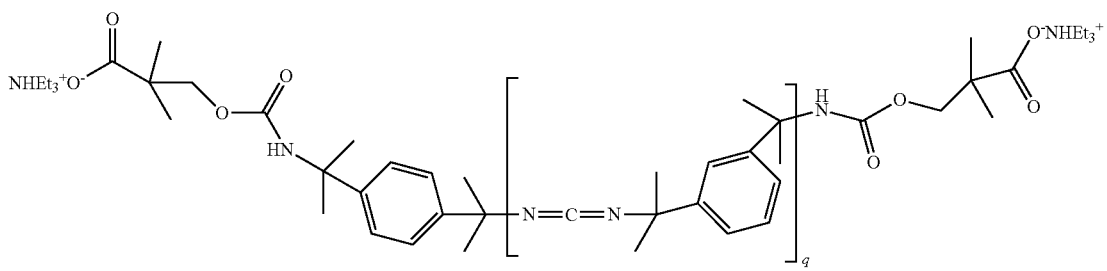

wherein q is from 1 to 20; and

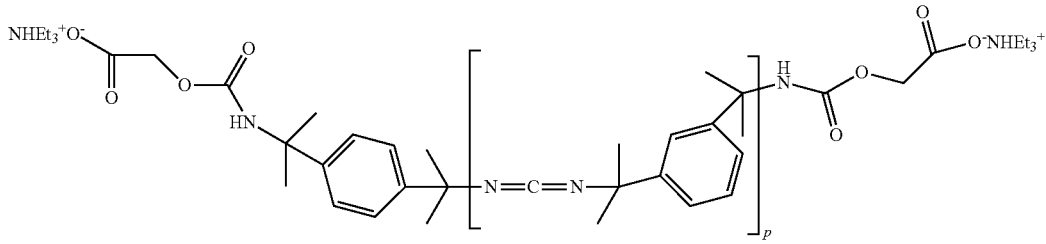

wherein p is from 1 to 20.

11. The composition of claim 1, wherein the carbodiimide is present in an amount from about 10 to about 250 mol % based on the number of carbodiimide groups that can react with carboxylic acid groups.

12. The composition of claim 1, wherein a film formed from the composition has at least one of:
   a. a storage modulus G at 100° C. from about $1 \times 10^3$ to about $1 \times 10^7$ Pa as measured by Dynamic Mechanical Analysis,
   b. a tensile strength from about $6.89 \times 10^5$ Pa (100 psi) to about $2.07 \times 10^7$ Pa (3000 psi) as measured by ASTM D2370,
   c. a % Strain at Break from about 100 to about 2000 as measured by ASTM D2370,
   d. a water absorption of less than 25% as measured by ASTM D870,
   e. a water solubles of less than 5% as measured by ASTM D870, and
   f. a gel content of more than 5%, as measured by ASTM 2765.

13. A method comprising applying the composition of claim 1, to at least one of on and in a substrate.

14. The method of claim 13 further comprising forming a film from the composition on the substrate.

15. The method of claim 14 further comprising curing the film by initiating a reaction between carboxyl groups and carbodiimide groups with UV radiation.

16. The method of claim 13, wherein at least a majority of the ethylenically unsaturated carboxylic acid is in a core of the water-dispersible film-forming polymer.

17. The method of claim 13, wherein at least a majority of the ethylenically unsaturated carboxylic acid is in a shell of the water-dispersible film-forming polymer.

18. The method of claim 13, wherein the ethylenically unsaturated carboxylic acid is distributed throughout the water-dispersible film-forming polymer.

19. The method of claim 13, wherein the water-dispersible film-forming polymer is formed from an at least two stage multi-stage reaction, and all of the ethylenically unsaturated carboxylic acid is polymerized in the first stage.

20. The method of claim 13, wherein the water-dispersible film-forming polymer is formed from an at least two stage multi-stage reaction, and all of the ethylenically unsaturated carboxylic acid is polymerized in the last stage.

21. The method of claim 13, wherein the water-dispersible film-forming polymer is from a gradient feed reaction.

22. The method of claim 13, wherein the ethylenically unsaturated carboxylic acid is at least one of (meth)acrylic acid, maleic acid, fumaric acid, itaconic acid, ethacrylic acid, crotonic acid, citraconic acid, cinnamic acid, phthalic acid, isophthalic acid, terephthalic acid, tetrahydrophthalic acid, hexahydrophthalic acid, tetrabromophthalic acid, trimellitic acid, pyromellitic acid, 1,4,5,6,7,7-hexachloro-5-norbornene-2,3-dicarboxylic acid, succinic acid, 2,6-naphthalenedicarboxylic acid, glutaric acid, sebacic acid, azelaic acid, 1,4-cyclohexanedicarboxylic acid, and 1,3-cyclohexanedicarbocylic acid.

23. The method of claim 13, wherein the ethylenically unsaturated carboxylic acid is at least one of acrylic acid, methacrylic acid, crotonic acid, and itaconic acid.

24. The method of claim 13, wherein the ethylenically unsaturated carboxylic acid is neutralized with a fugitive base.

25. The method of claim 13, wherein the carbodiimide is represented by at least one of the following structures:

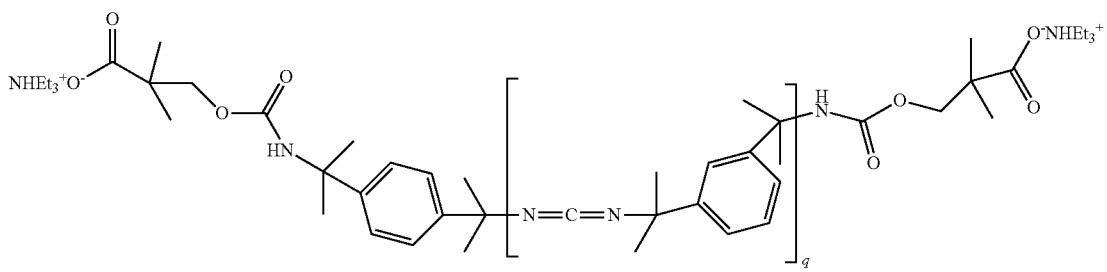

wherein q is from 1 to 20; and

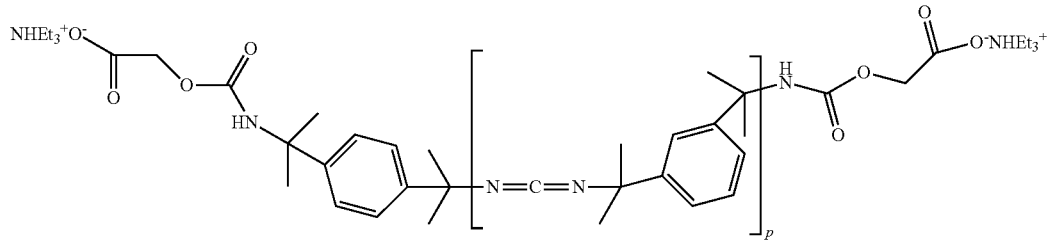

wherein p is from 1 to 20.

26. The method of claim 13, wherein the carbodiimide is present in an amount from about 10 to about 250 mol % based on the number of carbodiimide groups that can react with carboxylic acid groups.

27. The method of claim 13, wherein the film has at least one of:
  a. a storage modulus G at 100° C. from about $1 \times 10^3$ to about $1 \times 10^7$ Pa as measured by Dynamic Mechanical Analysis,
  b. a tensile strength from about $6.89 \times 10^5$ Pa (100 psi) to about $2.07 \times 10^7$ Pa (3000 psi) as measured by ASTM D2370,
  c. a % Strain at Break from about 100 to about 2000 as measured by ASTM D2370,
  d. a water absorption of less than 25% as measured by ASTM D870,
  e. a water solubles of less than 5% as measured by ASTM D870, and
  f. a gel content of more than 5% as measured by ASTM 2765.

28. The composition of claim 1 wherein the composition comprises the carbodiimide and, in addition, water-dispersible film-forming polymer consisting essentially of said polymer.

29. The composition of claim 1 wherein the composition comprises the carbodiimide and, in addition, water-dispersible film-forming polymer consisting essentially of polymer carrying carboxyl groups.

30. The method of claim 13 wherein the composition comprises the carbodiimide and, in addition, water-dispersible film-forming polymer consisting essentially of said polymer.

31. The method of claim 1 wherein the composition comprises the carbodiimide and, in addition, water-dispersible film-forming polymer consisting essentially of polymer carrying carboxyl groups.

32. The composition of claim 1 wherein the carbodiimide comprises at least one carboxylic acid group that has been neutralized with a fugitive base.

33. The method of claim 13, further comprising the steps of inhibiting reaction of carboxylic acid and carbodiimide groups by neutralizing at least one carboxylic acid group with a fugitive base prior to applying the composition of claim 1 on or in the substrate, and curing the applied composition under conditions sufficient to drive off the fugitive base.

34. The composition of claim 1 wherein the carbodiimide contains 500 to 2000 mmole/kg of carboxyl or carboxylate groups and 0.10 to 8 mol/kg of carbodiimide groups.

35. The composition of claim 34 wherein the carbodiimide consists of a reaction product of
  a) at least one of an aliphatic $C_4$ to $C_{20}$ polyisocyanate and an araliphatic $C_4$ to $C_{20}$ polyisocyanate,
  b) at least one of a mono-hydroxyl-functional carboxylic acid and a mono-hydroxyl-functional carboxylic salt, wherein the hydroxyl group is in the best position,
  c) optionally, a further compound carrying groups able to react with isocyanate groups in an addition reaction,
  d) optionally, at least one other isocyanate.

36. The composition of claim 1 wherein the proportion of components (c) and d), based on all components (a) to (d) used to prepare the carbodiimide, is not more than from 0 to 30% by weight.

37. The composition of claim 1 wherein the at least one of a mono-hydroxyl-functional carboxylic acid and a mono-hydroxyl-functional carboxylic salt is a compound having a hydroxyl group in a beta position.

38. The composition of claim 37 wherein the at least one of a mono-hydroxyl-functional carboxylic acid and a mono-hydroxyl-functional carboxylic salt is beta-hydroxy propionic acid, hydroxypivalic acid, alpha, alpha-hydroxymethylalkanoic acid, or a salt thereof.

* * * * *